(12) United States Patent
Gold et al.

(10) Patent No.: US 8,071,737 B2
(45) Date of Patent: Dec. 6, 2011

(54) NUCLEIC ACID LIGAND COMPLEXES

(75) Inventors: Larry Gold, Boulder, CO (US); Paul Schmidt, Niwot, CO (US); Nebojsa Janjic, Boulder, CO (US)

(73) Assignee: Glead Sciences, Inc., Forster City, CA (US)

( * ) Notice: Subject to any disclaimer, the term of this patent is extended or adjusted under 35 U.S.C. 154(b) by 190 days.

(21) Appl. No.: 12/624,314

(22) Filed: Nov. 23, 2009

(65) Prior Publication Data

US 2011/0212030 A1 Sep. 1, 2011

Related U.S. Application Data

(60) Continuation of application No. 10/261,159, filed on Sep. 30, 2002, now abandoned, which is a continuation of application No. 09/569,572, filed on May 10, 2000, now Pat. No. 6,465,188, which is a division of application No. 08/945,604, filed as application No. PCT/US96/06171 on May 2, 1996, now Pat. No. 6,147,204, which is a continuation-in-part of application No. 08/464,443, filed on Jun. 5, 1995, now abandoned, and a continuation-in-part of application No. 08/434,465, filed on May 4, 1995, now Pat. No. 6,011,020.

(51) Int. Cl.
C07H 21/02 (2006.01)
A61B 5/055 (2006.01)

(52) U.S. Cl. ........................ 536/23.1; 424/9.3

(58) Field of Classification Search .................. None
See application file for complete search history.

(56) References Cited

U.S. PATENT DOCUMENTS

| | | |
|---|---|---|
| 4,207,200 A | 6/1980 | Müller et al. |
| 4,766,106 A | 8/1988 | Katre et al. |
| 4,861,597 A | 8/1989 | Kida et al. |
| 4,904,582 A | 2/1990 | Tulles |
| 4,914,210 A | 4/1990 | Levenson et al. |
| 4,962,029 A | 10/1990 | Levenson et al. |
| 5,013,556 A | 5/1991 | Woodle et al. |
| 5,087,617 A | 2/1992 | Smith |
| 5,142,047 A | 8/1992 | Summerton et al. |
| 5,149,794 A | 9/1992 | Yatvin et al. |
| 5,227,170 A | 7/1993 | Sullivan |
| 5,245,022 A | 9/1993 | Weis et al. |
| 5,264,209 A | 11/1993 | Mikayama et al. |
| 5,270,163 A | 12/1993 | Gold et al. |
| 5,276,013 A | 1/1994 | Conrad et al. |
| 5,279,833 A | 1/1994 | Rose |
| 5,320,906 A | 6/1994 | Eley et al. |
| 5,459,015 A | 10/1995 | Janjic et al. |
| 5,470,911 A | 11/1995 | Rhee et al. |
| 5,472,841 A | 12/1995 | Jayasena et al. |
| 5,475,096 A | 12/1995 | Gold et al. |
| 5,476,766 A | 12/1995 | Gold et al. |
| 5,496,938 A | 3/1996 | Gold et al. |
| 5,503,978 A | 4/1996 | Schneider et al. |
| 5,527,894 A | 6/1996 | Gold et al. |
| 5,543,293 A | 8/1996 | Gold et al. |
| 5,554,388 A | 9/1996 | Illum |
| 5,563,255 A | 10/1996 | Monia et al. |
| 5,567,588 A | 10/1996 | Gold et al. |
| 5,567,685 A | 10/1996 | Linden et al. |
| 5,567,690 A | 10/1996 | Inoue et al. |
| 5,580,737 A | 12/1996 | Polisky et al. |
| 5,587,199 A | 12/1996 | Tournier et al. |
| 5,587,468 A | 12/1996 | Allen et al. |
| 5,595,877 A | 1/1997 | Gold et al. |
| 5,603,953 A | 2/1997 | Herbig et al. |
| 5,614,503 A | 3/1997 | Chaudhary et al. |
| 5,631,237 A | 5/1997 | Dzau et al. |
| 5,648,095 A | 7/1997 | Illum et al. |
| 5,683,867 A | 11/1997 | Biesecker et al. |
| 5,705,337 A | 1/1998 | Gold et al. |
| 5,763,595 A | 6/1998 | Gold et al. |
| 5,767,073 A | 6/1998 | Lim et al. |
| 5,801,154 A | 9/1998 | Baracchini et al. |
| 5,824,778 A | 10/1998 | Ishikawa et al. |
| 5,843,473 A | 12/1998 | Woodle et al. |
| 5,925,375 A | 7/1999 | Lenk et al. |
| 5,951,972 A | 9/1999 | Daley et al. |
| 5,962,219 A | 10/1999 | Gold et al. |
| 5,998,142 A | 12/1999 | Gold et al. |
| 6,005,094 A | 12/1999 | Simon et al. |
| 6,011,020 A | 1/2000 | Gold et al. |
| 6,051,698 A | 4/2000 | Janjic et al. |
| 6,083,696 A | 7/2000 | Biesecker et al. |
| 6,147,204 A | 11/2000 | Gold et al. |

(Continued)

FOREIGN PATENT DOCUMENTS

EP 0 292 128 11/1988

(Continued)

OTHER PUBLICATIONS

U.S. Appl. No. 08/464,443, filed Jun. 5, 1995, Gold et al.
Abuchowski et al (1977) J Biol Chem 252(11):3578.
Abuchowski et al (1977) J Biol Chem 252(11):3582.
Abuchowski et al (1979) Can Treat Rep 63(6):1127.
Abuchowski et al (1984) Can Biochem Biophys 7:175.
Agrawal et al. (1995) Biochem. Pharm. 50:571.
Benseler et al. (1993) J Am Chem Soc 115:8483-8484.
Bonora et al. (1990) Nucleic Acids Res 18(11):3155-3159.
Bonora et al. (1993) Nucleic Acids Res 21(5):1213-1217.
de Smidt (1991) Nucleic Acids Research 19:4695-4700.
Drug Delivery System, Nankodo Co., Ltd. Apr. 15, 1986, , First Edition, pp. 137-197.

(Continued)

Primary Examiner — Tracy Vivlemore
(74) Attorney, Agent, or Firm — Swanson & Bratschun, L.L.P.

(57) ABSTRACT

This invention discloses a method for preparing a therapeutic or diagnostic complex comprised of a nucleic acid ligand and a lipophilic compound or non-immunogenic, high molecular weight compound by identifying a nucleic acid ligand by SELEX methodology and associating the nucleic acid ligand with a lipophilic compound or a non-immunogenic, high molecular weight compound. The invention further discloses complexes comprising one or more nucleic acid ligands in association with a lipophilic compound or non-immunogenic, high molecular weight compound.

1 Claim, 34 Drawing Sheets

U.S. PATENT DOCUMENTS

| | | |
|---|---|---|
| 6,168,778 B1 | 1/2001 | Janjic et al. |
| 6,229,002 B1 | 5/2001 | Janjic et al. |
| 6,300,074 B1 | 10/2001 | Gold et al. |
| 6,426,335 B1 | 7/2002 | Janjic et al. |
| 6,465,188 B1 | 10/2002 | Gold et al. |
| 6,465,189 B1 | 10/2002 | Biesecker et al. |
| 2003/0077646 A1 | 4/2003 | Biesecker et al. |
| 2003/0114404 A1 | 6/2003 | Janjic et al. |
| 2003/0125263 A1 | 7/2003 | Gold et al. |
| 2005/0164974 A1 | 7/2005 | Gold et al. |
| 2006/0088877 A1 | 4/2006 | Gold et al. |

FOREIGN PATENT DOCUMENTS

| | | |
|---|---|---|
| EP | 0 438 259 | 7/1991 |
| EP | 0 462 145 | 4/1994 |
| GB | 1 599 454 | 10/1981 |
| GB | 2 183 661 | 6/1987 |
| WO | WO 87/00056 | 1/1987 |
| WO | WO 88/09810 | 12/1988 |
| WO | WO 89/06694 | 7/1989 |
| WO | WO 90/10448 | 9/1990 |
| WO | WO 91/10426 | 7/1991 |
| WO | WO 91/14696 | 10/1991 |
| WO | WO 91/19813 | 12/1991 |
| WO | WO 92/14843 | 9/1992 |
| WO | WO 93/19768 | 10/1993 |
| WO | WO 93/24507 | 12/1993 |
| WO | WO 93/25197 | 12/1993 |
| WO | WO 94/01448 | 1/1994 |
| WO | WO 94/08050 | 4/1994 |
| WO | WO 94/15619 | 7/1994 |
| WO | WO 94/27615 | 12/1994 |
| WO | WO 94/29479 | 12/1994 |
| WO | WO 95/00528 | 1/1995 |
| WO | WO 95/00529 | 1/1995 |
| WO | WO 95/06474 | 3/1995 |
| WO | WO 95/06659 | 3/1995 |
| WO | WO 95/07073 | 3/1995 |
| WO | WO 96/06171 | 2/1996 |
| WO | WO 96/11205 | 4/1996 |
| WO | WO 96/21469 | 7/1996 |
| WO | WO 96/27605 | 9/1996 |

OTHER PUBLICATIONS

Efimov et al. (1993) Nucleic Acids Res 21(23):5337-5344.
Efimov et al. (1994) "Synthesis of polyethylene glycol-oligonucleotide conjugates," Chem. Abstracts Service, Database Accession No. 121:83819.
Ellington & Szostak (1990) Abstract of papers presented at the 1990 meeting on RNA Processing, Cold Spring Harbor Laboratory, Cold Spring Harbor, New York, p. 84.
European Search Report prepared for European Patent Application No. 09014540.0, dated Feb. 19, 2010, 5 pages.
Gabizon et al. (1993) Pharm Res 10(5):703.
Goodson et al. (1990) Bio/Technology 8:343.
Griffin et al. (1993) Blood 81(12):3271-3276.
Harris (1992) Introduction to Biotechnical and Biomedical Applications of Poly(Ethylene Glycol), Biotechnical and Biomedcial Applications. pp. 1-14.
Harris, (1985) Synthesis of polyethylene glycol derivatives, J. Macromol. Sci. Rev. Macromol. Chem. Phys. C25 350-373.
Hershfield et al. (1987) New Eng J Med 316(10):589.
Hershfield et al. (1991) Proc Natl Acad Sci USA 88:7185.
Ijiro et al. (1992) J. Chem Soc. Chem. Commun. "A DNA lipid complex soluble in organic solvents" pp. 1339-1341.
Jablonski et al. (1986) Nucl. Acids Res. 14:6115.
Jaschke et al. (1993) Tetrahedron Letters 34(2):301-304.
Jaschke et al. (1994) Nucl Acids Res. 22(10):1880-1884.
Jaschke et al. (1994) Nucl. Acids Res. 22:4810.
Jones et al. (1994) Bioconjugate Chem. 5:390.
Joyce & Inoue (1989) Nucl. Acids Res. 17:711.
Joyce (1989) Gene 82:83.
Kabanov et al. (1990) FEBS Lets. 259:327.
Kawaguchi et al. (1995) Biol Pharm Bull 18(3):474-476.
Kim et al., (1993) Nature 362:841-844.
Kinzler & Vogelstein (1989) Nucl. Acids Res. 17:3645.
Knauff et al. (1988) J Biol Chem 263(29):15064.
Kramer et al. (1974) J. Mol. Biol. 89:719.
Lasic et al. (1995) Science 267:1275.
Laukkanen et al. (1994) Biochem. 33:11664.
Letsinger et al. (1989) Proc. Natl. Acad. Sci. USA 86:6553.
Levisohn & Spiegelman (1968) Proc. Natl. Acad. Sci. USA 60:866.
Levisohn & Spiegelman (1969) Proc. Natl. Acad. Sci. USA 63:805.
Ma et al. (1993) Biochemistry 32:1751-1758.
Ma et al. (1993) Nucl Acids Res 21(11):2585-2589.
MacKellar et al. (1992) Nucl. Acids Res. 20:3411.
Marcus-Sekura et al. (1987) Nucl. Acids Res. 15:5749.
Maurizot et al. (1991) FEBS Letters 288(1,2):101-104.
Meyers et al. (1991) Clin Pharmacol Ther 49(3):307.
Nucci et al. (1991) Advanced Drug Delivery Reviews 6:133-151.
Oberhauser et al. (1992) Nucl. Acids Res. 20:533.
Oliphant & Struhl (1987) Methods in Enzymology 155:568.
Oliphant & Struhl (1988) Nucl. Acids Res. 16:7673.
Oliphant et al. (1986) Gene 44:177.
Oliphant et al. (1989) Mol. Cell. Biol. 9:2944.
Robertson & Joyce (1990) Nature 344:467.
Saison-Behmoaras et al. (1991) EMBO J. 10:1111.
Savoca et al. (1979) Biochim Biophys Acta 578:47.
Sekiguchi et al. (1988) Biomat Art Cells Art Org 16(1-3):113.
Senior et al. (1991) Biochim. et Biophys. 1062:77.
Shea et al. (1990) Nucl. Acids Res. 18:3777.
Shih et al. (1992) Eeur J. Immunol 22:727.
Stewart (1992) Human Gene Therapy "Gene transfer in vivo with DNA-liposomes complexes: safety and acute toxicity in mice" 3:267-275.
Stull et al. (1995) Pharmaceutical Res 12(4):465-483.
Tanaka et al. (1991) Cancer Res 51:3710.
Thiesen & Bach (1990) Nucl. Acids Res. 18:3203.
Thompson et al. (1993) Nucl Acids Res 21(24): 5600-5603.
Uhlmann et al. (1990) Chem. Reviews 90:544.
van der Krol et al. (1988) Biotechniques 6:958.
Veronese et al. (1983) J Pharm Pharmacol 35:757.
Visco et al. (1987) II Farmaco Ed Sc 42(8):549.
Wang et al. (1995) Proc. Natl. Acad. Sci. USA 92:3318.
Zalipsky et al. (1995) Adv Drug Delivery Review 16:157-182.
Zhang et al. (1995) Biochem. Pharm. 49:929.
Zhang et al. (1995) Biochem. Pharm. 50:545.

NX-229
SEQ ID NO: 6

Ligand = 5'-CAGTCCGTGGTAGGGCAGGTTGGGGTGACTTCGTGGAsAs-3'
(Thrombin ligand)

s = Phosphorothioate =

225T3
SEQ ID NO: 10

Structure = Ligand

Ligand component =5'-GCGGGGCTACGTACCGGGGCTTTGTAAAACCCCGC-3'
(bFGF ligand)

225T3N
SEQ ID NO: 11

Structure = Ligand

Ligand component = 5' - GCGGGGCTACGTACCGGGGCTTTGTAAAACCCCGC-3'
(bFGF ligand)

T-P4
SEQ ID NO: 12

Structure =

Ligand component =

5'-CAGTCCGTGGTAGGGCAGGTTGGGGTGACTTCGTGGA-3'
(Thrombin ligand)

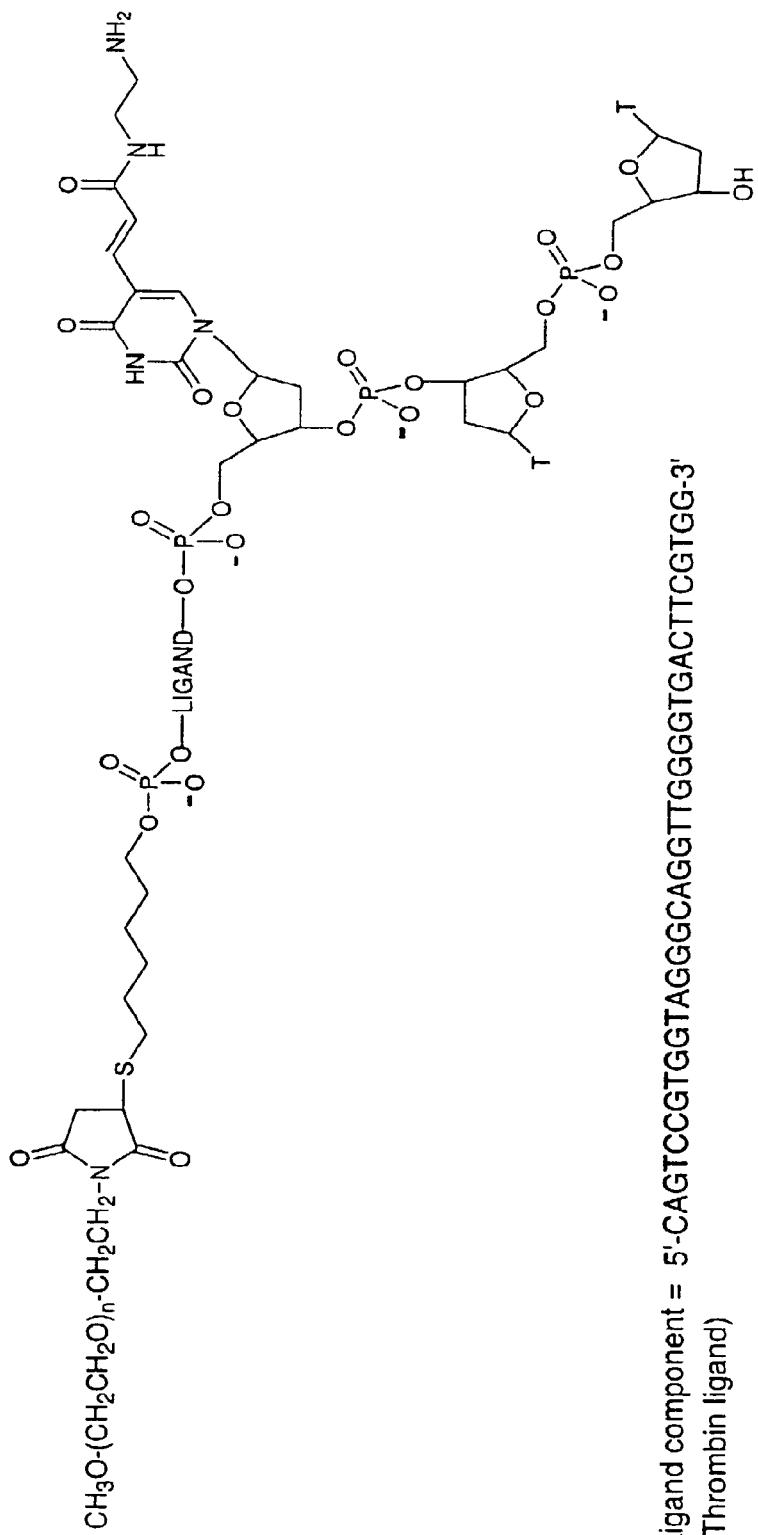

225T3N-PEG-3400
SEQ ID NO: 14

Structure =

Ligand component =

5'-GCGGGGCTACGTACCGGGGCTTTGTAAAACCCCGC-3'
(bFGF ligand)

NX-268
SEQ ID NO: 16

Structure =

Ligand component =
5'-TsTsTsTsmAaCaCaCaUrGrAaUmAmGrGaUmGrGaUmAmGrAaCmGaCaCmGmGmGmGaUmGTsTsTsTsT-3'
(VEGF ligand)

NX 191
SEQ ID NO: 17

Ligand =

5'-TsTsTsmAmCmCmCmUmGmAmUmGmGmAmCmGmCmGmGmGmUmGTsTsTsTsT-3'

(derived from VEGF ligand)

FIGURE 1L

NX-278
SEQ ID NO: 19

Structure =

Ligand component =
5'-TsTsTsTsmAaCaCaUrGaUmAmGrAaUmGrGaUmAmGrAaCmGaCaCmGmGmGmGaUmGTsTsTsTsTsT-3'
(VEGF ligand)

JW-986
SEQ ID NO: 20

Structure =

Ligand component =
5'-mUmUmUmAmCmCmCmUmGmAmAmUmGmUmAmAmCmGmCmCmGmGmGmUmG-3'
(derived from VEGF ligand)

NX-213
SEQ ID NO: 21

Ligand =
5'-TsTsTsTsmAaCaCaUrGaUmAmGrAaCmGaCaCmGmGmGmGaUmGTsTsTsTsT-3'

FIGURE 1P

NX-244
SEQ ID NO: 22

Structure = FLUORESCEIN—[linker structure]—O-P(=O)(O⁻)-O-LIGAND

Ligand component =
5'-TsTsTsTsmAaCaCaUrGaUmAmGrAaCmGaCaCmGmGmGmGaUmGTsTsTsTsT-3'
(VEGF ligand)

FIGURE 1Q

JW-1130
SEQ ID NO: 23

Ligand component =

5'-mUmUmUmAfCfCfUmGfUmAmGmAfUmGfCfCmGmGmGfUmG-3'
(derived from VEGF ligand)

JW-1336-20K PEG
SEQ ID NO: 25

Structure =

Ligand component =
5'-mUmUmUAfCfCfUGAfUmGGfUmAmGAfCmGfCfCmGmGmGmGfUmG-3'
(derived from VEGF ligand)

JW-1379
SEQ ID NO: 26

Structure =

Ligand component =
5'-mUmUmUmUAfCfCfUGAfUGGfUAGAfCGfCfCGGGfUG-3'
(derived from VEGF ligand)

JW-1380
SEQ ID NO: 27

Structure =

Ligand component =
5'-mUmUmUmUACCCfUGAfUGGfUAGAfCGfCfCGGGfUGT-3'
(derived from VEGF ligand)

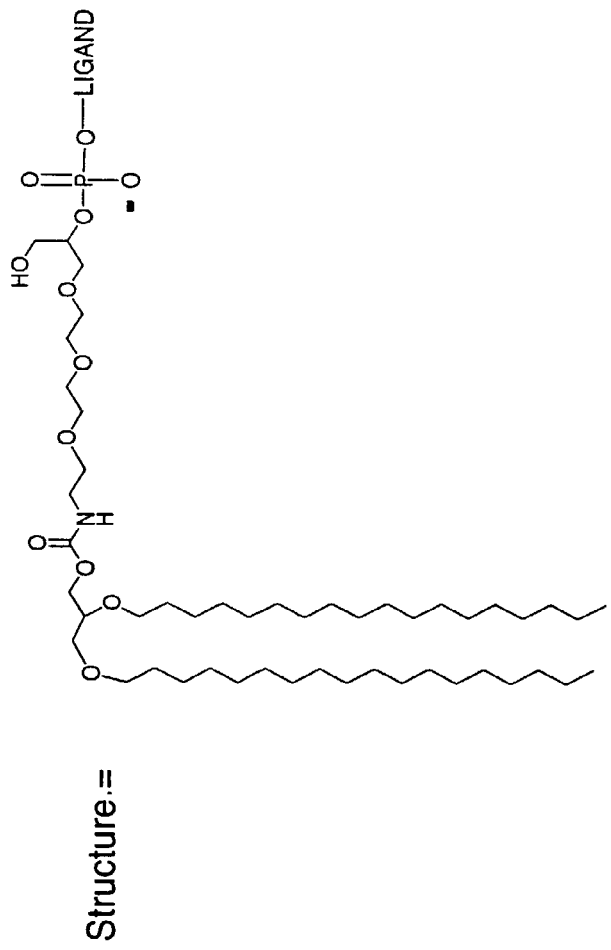
scNX-278
SEQ ID NO: 28
Structure:=
Ligand component =
5'-TsTsTsTs mGaUaC mGmGaU mAaCrG mGrAmG aUmGrG rAaCaC mGaUaC mAaCmG TsTsTs JW-986-PEG- (10,000, 20,000 or 40,000)

SEQ ID NO: 29

Structure =

Ligand component =
5'-mUmUmUmUAfCfCfCfUGAfUmGGfUmAmGAfCmGfCfCmGmGmGmGfUmG-3'
(derived from VEGF ligand)

JW-1336
SEQ ID NO: 30

Structure =

Ligand component =
5'-mUmUmUmUAfCfCfCfUGAfUmAmGAfCmGfCfCmGmGmGmGfUmG-3'

SEQUENCE LISTING (1) GENERAL INFORMATION:

(iii) NUMBER OF SEQUENCES: 30

(2) INFORMATION FOR SEQ ID NO: 1:

(i) SEQUENCE CHARACTERISTICS:
      (A) LENGTH: 23
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO: 1:

TTTTTTTTGT CAGGCACCAT CCC                                   23

(2) INFORMATION FOR SEQ ID NO: 2:

(i) SEQUENCE CHARACTERISTICS:
      (A) LENGTH: 25
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO: 2:

CCCCACTGAA GCACCTTTTT TTTTT                                25

(2) INFORMATION FOR SEQ ID NO: 3:

```
    (i) SEQUENCE CHARACTERISTICS:
        (A) LENGTH: 36
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 3:

CAGTCCGTGG TAGGGCAGGT TGGGGTGACT TCGTGG                                36

(2) INFORMATION FOR SEQ ID NO: 4:

(i) SEQUENCE CHARACTERISTICS:
        (A) LENGTH: 53
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION:  Nucleotides 49-53 are bound by a
            phosphorothioate linkage (xi) SEQUENCE DESCRIPTION: SEQ ID NO: 4:

ATCCGCCTGA TTAGCGATAC TCAGAAGGAT AAACTGTCCA GAACTTGGAT                 50

TTT                                                                    53

(2) INFORMATION FOR SEQ ID NO: 5:

(i) SEQUENCE CHARACTERISTICS:
        (A) LENGTH: 40
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: Nucleotide 39 is an inverted-
            orientation (3'3'linkage) phosphoramidite (xi) SEQUENCE DESCRIPTION: SEQ ID NO: 5:

CAGTCCGTGG TAGGGCAGGT TGGGGTGACT TCGTGGAATT                            40

(2) INFORMATION FOR SEQ ID NO: 6:

(i) SEQUENCE CHARACTERISTICS:
        (A) LENGTH: 38
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION:  Nucleotides 37 and 38 are bound by a
            phosphorothioate bond (xi) SEQUENCE DESCRIPTION: SEQ ID NO: 6:

CAGTCCGTGG TAGGGCAGGT TGGGGTGACT TCGTGGAA                              38

(2) INFORMATION FOR SEQ ID NO: 7:

(i) SEQUENCE CHARACTERISTICS:
        (A) LENGTH: 39
        (B) TYPE: nucleic acid
        (C) STRANDEDNESS: single
        (D) TOPOLOGY: linear
```

(ii) MOLECULE TYPE: DNA (xi) SEQUENCE DESCRIPTION: SEQ ID NO: 7:

CAGTCCGTGG TAGGGCAGGT TGGGGTGACT TCGTGGAAT                    39

(2) INFORMATION FOR SEQ ID NO: 8:

(i) SEQUENCE CHARACTERISTICS:
        (A) LENGTH: 40
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: Nucleotide number 39 is an inverted-
            orientation (3'3' linkage) phosphoramidite (xi) SEQUENCE DESCRIPTION: SEQ ID NO: 8:

CAGTCCGTGG TAGGGCAGGT TGGGGTGACT TCGTGGAATT                   40

(2) INFORMATION FOR SEQ ID NO: 9:

(i) SEQUENCE CHARACTERISTICS:
        (A) LENGTH: 38
        (B) TYPE: nucleic acid
        (C) STRANDEDNESS: single
        (D) TOPOLOGY: linear (ii) MOLECULE TYPE: DNA (ix) FEATURE:

(ix) FEATURE:
        (D) OTHER INFORMATION:  Nucleotide number 37 is an inverted-
            orientation (3'3' linkage) phosphoramidite (xi) SEQUENCE DESCRIPTION: SEQ ID NO: 9:

CAGTCCGTGG TAGGGCAGGT TGGGGTGACT TCGTGGTT                     38

(2) INFORMATION FOR SEQ ID NO: 10:

(i) SEQUENCE CHARACTERISTICS:
        (A) LENGTH: 35
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 10:

GCGGGGCTAC GTACCGGGGC TTTGTAAAAC CCCGC                        35

(2) INFORMATION FOR SEQ ID NO: 11:

(i) SEQUENCE CHARACTERISTICS:
        (A) LENGTH: 35
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 11:

GCGGGGCTAC GTACCGGGGC TTTGTAAAAC CCCGC                        35

(2) INFORMATION FOR SEQ ID NO: 12:

(i) SEQUENCE CHARACTERISTICS:

(A) LENGTH: 40
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION:  Nucleotide number 39 is an inverted
            orientation phosphoramidite (xi) SEQUENCE DESCRIPTION: SEQ ID NO: 12:

TCAGTCCGTG GTAGGGCAGG TTGGGGTGAC TTCGTGGATT                          40

(2) INFORMATION FOR SEQ ID NO: 13:

(i) SEQUENCE CHARACTERISTICS:
        (A) LENGTH: 38
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION:  Nucleotide 37 is an inverted
            orientation (3'3' linkage) phosphoramidite (xi) SEQUENCE DESCRIPTION: SEQ ID NO: 13:

CAGTCCGTGG TAGGGCAGGT TGGGGTGACT TCGTGGTT                            38

(2) INFORMATION FOR SEQ ID NO: 14:

(i) SEQUENCE CHARACTERISTICS:
        (A) LENGTH: 35
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 14:

GCGGGGCTAC GTACCGGGGC TTTGTAAAAC CCCGC                               35

(2) INFORMATION FOR SEQ ID NO: 15:

(i) SEQUENCE CHARACTERISTICS:
        (A) LENGTH: 38
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION:  Nucleotide number 37 is an inverted
            orientation (3'3' linkage) phosphoramidite (xi) SEQUENCE DESCRIPTION: SEQ ID NO: 15:

TCAGTCCGTG GTAGGGCAGG TTGGGGTGAC TTCGTGTT                            38

(2) INFORMATION FOR SEQ ID NO: 16:

(i) SEQUENCE CHARACTERISTICS:
        (A) LENGTH: 33
        (B) TYPE: nucleic acid
        (C) STRANDEDNESS: single
        (D) TOPOLOGY: linear (ii) MOLECULE TYPE: DNA (ix) FEATURE:

```
        (D) OTHER INFORMATION: Nucleotides at positions 1-4 and 29-33
            are bound by a phosphorothioate bond.

(ix) FEATURE:
        (D) OTHER INFORMATION: Nucleotides at positions 5, 13, 16,
            17, 20, 23-26, and 28 are 2-OMethyl (2'-OMe) modified.

(ix) FEATURE:
        (D) OTHER INFORMATION: Nucleotides at positions 6-9, 12, 15,
            19, 21, 22, and 27 are 2'-amino (2'-NH2) modified.

(xi) SEQUENCE DESCRIPTION: SEQ ID NO: 16:

TTTTACCCUG AUGGUAGACG CCGGGGUGTT TTT                                33

(2) INFORMATION FOR SEQ ID NO: 17:

(i) SEQUENCE CHARACTERISTICS:
        (A) LENGTH: 33
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: Nucleotides at positions 1-4 and 29-33
            are bound by a phosphorothioate bond.

(ix) FEATURE:
        (D) OTHER INFORMATION: Nucleotides at positions 5-28 are
            2'-OMethyl (2'-OMe) modified.

(xi) SEQUENCE DESCRIPTION: SEQ ID NO: 17:

TTTTACCCUG AUGGUAGACG CCGGGGUGTT TTT                                33

(2) INFORMATION FOR SEQ ID NO: 18:

(i) SEQUENCE CHARACTERISTICS:
        (A) LENGTH: 38
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 18:

CAGTCCGTGG TAGGGCAGGT TGGGGTGACT TCGTGGAA                           38

(2) INFORMATION FOR SEQ ID NO: 19:

(i) SEQUENCE CHARACTERISTICS:
        (A) LENGTH: 33
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: Nucleotides at positions 1-4 and 29-33
            are bound by a phosphorothioate bond.

(ix) FEATURE:
        (D) OTHER INFORMATION: Nucleotides at positions 5, 13, 16,
            17, 20, 23-26, and 28 are 2'-OMethyl (2'-OMe) modified.

(ix) FEATURE:
        (D) OTHER INFORMATION: Nucleotides at positions 6-9, 12, 15,
            19, 21, 22 and 27 are 2'-amino (2'-NH2) modified.

(xi) SEQUENCE DESCRIPTION: SEQ ID NO: 19:

TTTTACCCUG AUGGUAGACG CCGGGGUGTT TTT                                33
```

(2) INFORMATION FOR SEQ ID NO: 20:

(i) SEQUENCE CHARACTERISTICS:
        (A) LENGTH: 28
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: All nucleotides are 2'-OMethyl
            (2'-OMe) modified.

(xi) SEQUENCE DESCRIPTION: SEQ ID NO: 20:

UUUUACCCUG AUGGUAGACG CCGGGGUG                                      28

(2) INFORMATION FOR SEQ ID NO: 21:

(i) SEQUENCE CHARACTERISTICS:
        (A) LENGTH: 33
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: Nucleotides at positions 1-4 and 29-33
            are bound by a phosphorothioate bond (ix) FEATURE:
        (D) OTHER INFORMATION: Nucleotides at positions 5, 13, 16,
            17, 20, 23-26, and 28 are 2=-OMethyl (2=-OMe) modified (ix) FEATURE:
        (D) OTHER INFORMATION: Nucleotides at positions 6-9, 12, 15,
            19, 21, 22 and 27 are 2=-amino (2=-NH2) modified (xi) SEQUENCE DESCRIPTION: SEQ ID NO: 21:

TTTTACCCUG AUGGUAGACG CCGGGGUGTT TTT                                 33

(2) INFORMATION FOR SEQ ID NO: 22:

(i) SEQUENCE CHARACTERISTICS:
        (A) LENGTH: 33
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: Nucleotides at positions 1-4 and 29-33
            are bound by a phosphorothioate bond.

(ix) FEATURE:
        (D) OTHER INFORMATION: Nucleotides at positions 5, 13, 16,
            17, 20, 23-26, and 28 are 2'-OMethyl (2'-OMe) modified.

(ix) FEATURE:
        (D) OTHER INFORMATION: Nucleotides at positions 6-9, 12, 15,
            19, 21, 22, and 27 are 2'-amino (2'-NH2) modified.

(xi) SEQUENCE DESCRIPTION: SEQ ID NO: 22:

TTTTACCCUG AUGGUAGACG CCGGGGUGTT TTT                                 33

(2) INFORMATION FOR SEQ ID NO: 23:

(i) SEQUENCE CHARACTERISTICS:
        (A) LENGTH: 28
        (B) TYPE: nucleic acid
        (C) STRANDEDNESS: single

```
        (D) TOPOLOGY: linear (ii) MOLECULE TYPE: RNA (ix) FEATURE:
        (D) OTHER INFORMATION:  Nucleotides at positions 1-5, 10-11,
            13-14, 16-18, 20, 23-26, and 28 are 2'-OMethyl (2'-OMe)
            modified.

(ix) FEATURE:
        (D) OTHER INFORMATION:  Nucleotides at positions 6-9, 12, 15,
            19, 21-22, and 27 are 2'-Fluoro (2'-F) modified.

(xi) SEQUENCE DESCRIPTION: SEQ ID NO: 23:

UUUUACCCUG AUGGUAGACG CCGGGGUG                                               28

(2) INFORMATION FOR SEQ ID NO: 24:

(i) SEQUENCE CHARACTERISTICS:
        (A) LENGTH: 48
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO: 24:

AGCCATTCAC CATGGCCCCT TCCTACGTAT GTTCTGCGGG TGGCTTAC                         48

(2) INFORMATION FOR SEQ ID NO: 25:

(i) SEQUENCE CHARACTERISTICS:
        (A) LENGTH: 28
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  Nucleotides at positions 1-4, 13,
            16-17, 20, 23-26, and 28 are 2'-OMethyl (2'-OMe)
            modified.

(ix) FEATURE:
        (D) OTHER INFORMATION:  Nucleotides at positions 6-9, 12, 15,
            19, 21-22, and 27 are 2'-Fluoro (2'-F) modified.

(xi) SEQUENCE DESCRIPTION: SEQ ID NO: 25:

UUUUACCCUG AUGGUAGACG CCGGGGUG                                               28

(2) INFORMATION FOR SEQ ID NO: 26:

(i) SEQUENCE CHARACTERISTICS:
        (A) LENGTH: 28
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  Nucleotides at positions 1-4 are
            2'-OMethyl (2'-OMe) modified.

(ix) FEATURE:
        (D) OTHER INFORMATION:  Nucleotides at positions 6-9, 12, 15,
            19, 21-22, and 27 are 2'-Fluoro (2'-F) modified.

(xi) SEQUENCE DESCRIPTION: SEQ ID NO: 26:

UUUUACCCUG AUGGUAGACG CCGGGGUG                                               28
```

(2) INFORMATION FOR SEQ ID NO: 27:

(i) SEQUENCE CHARACTERISTICS:
        (A) LENGTH: 29
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: Nucleotides at positions 1-4 are
            2'-OMethyl (2'-OMe) modified.

(ix) FEATURE:
        (D) OTHER INFORMATION: Nucleotides at positions 6-9, 12, 15,
            19, 21-22, and 27 are 2'-Fluoro (2'-F) modified.

(xi) SEQUENCE DESCRIPTION: SEQ ID NO: 27:

UUUUACCCUG AUGGUAGACG CCGGGGUGT                              29

(2) INFORMATION FOR SEQ ID NO: 28:

(i) SEQUENCE CHARACTERISTICS:
        (A) LENGTH: 33
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: Nucleotides at positions 1-4 and 29-33
            are bound by a phosphorothiate bond.

(ix) FEATURE:
        (D) OTHER INFORMATION: Nucleotides at positions 5, 8-9, 11,
            14, 16, 18, 23, 26, and 28 are 2=-OMethyl (2=OMe)
            modified.

(ix) FEATURE:
        (D) OTHER INFORMATION: Nucleotides at positions 6-7, 10, 12,
            17, 21-22, 24-25, and 27 are 2=-amino (2=-NH2) modified.

(xi) SEQUENCE DESCRIPTION: SEQ ID NO: 28:

TTTTGUCGGU ACGGAGUGGA CCGUCACGTT TTT                          33

(2) INFORMATION FOR SEQ ID NO: 29:

(i) SEQUENCE CHARACTERISTICS:
        (A) LENGTH: 28
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: Nucleotides at positions 1-4, 13,
            16-17, 20, 23-26, and 28 are 2'-OMethyl (2'-OMe)
            modified.

(ix) FEATURE:
        (D) OTHER INFORMATION: Nucleotides at positions 6-9, 12, 15,
            19, 21-22, and 27 are 2'-Fluoro (2'-F) modified.

(xi) SEQUENCE DESCRIPTION: SEQ ID NO: 29:

UUUUACCCUG AUGGUAGACG CCGGGGUG                               28

(2) INFORMATION FOR SEQ ID NO: 30:

(i) SEQUENCE CHARACTERISTICS:
        (A) LENGTH: 28
        (B) TYPE: nucleic acid -continued

```
        (C) STRANDEDNESS: single
        (D) TOPOLOGY: linear (ii) MOLECULE TYPE: RNA (ix) FEATURE:
        (D) OTHER INFORMATION:   Nucleotides at positions 1-4, 13,
            16-17, 20, 23-26, and 28 are 2'-OMethyl (2'-OMe)
            modified.

(ix) FEATURE:
        (D) OTHER INFORMATION:   Nucleotides at positions 6-9, 12, 15,
            19, 21-22, and 27 are 2'-Fluoro (2'-F) modified.

(xi) SEQUENCE DESCRIPTION: SEQ ID NO: 30:

UUUUACCCUG AUGGUAGACG CCGGGGUG                                            28
```

NUCLEIC ACID LIGAND COMPLEXES

RELATEDNESS OF THE APPLICATION

The subject application is a continuation of U.S. Ser. No. 10/261,159, filed Sep. 30, 2002, which is a continuation of U.S. Ser. No. 09/569,572, filed May 10, 2000, now U.S. Pat. No. 6,465,188, which is a division of U.S. Ser. No. 08/945,604, filed Oct. 28, 1997, now U.S. Pat. No. 6,147,204, which is Section 371 national phase of PCT/US96/06171, filed May 2, 1996, which is a continuation-in-part of U.S. Ser. No. 08/434,465, filed May 4, 1995, now U.S. Pat. No. 6,011,020, and which is a continuation-in-part of U.S. Ser. No. 08/464,443, filed Jun. 5, 1995, now abandoned.

FIELD OF THE INVENTION

This invention relates to a method for preparing a therapeutic or diagnostic Complex comprised of a Nucleic Acid Ligand and a Lipophilic Compound or Non-Immunogenic, High Molecular Weight Compound by identifying a Nucleic Acid Ligand by SELEX methodology and associating the Nucleic Acid Ligand with a Lipophilic Compound or a Non-Immunogenic, High Molecular Weight Compound. The invention further relates to improving the pharmacokinetic properties of a Nucleic Acid Ligand by associating the Nucleic Acid Ligand to a Lipophilic Compound or Non-Immunogenic, High Molecular Weight Compound to form a Complex. The invention further relates to a method for targeting a therapeutic or diagnostic agent to a specific predetermined biological Target by associating the agent with a Complex comprised of a Nucleic Acid Ligand and a Lipophilic Compound or Non-Immunogenic, High Molecular Weight Compound, wherein the Nucleic Acid Ligand has a SELEX Target associated with the specific predetermined Target and the Nucleic Acid Ligand is associated with the exterior of the Complex. The invention also includes complexes comprising one or more Nucleic Acid Ligand in association with a Lipophilic Compound or Non-Immunogenic, High Molecular Weight Compound.

BACKGROUND OF THE INVENTION

A. Selex

The dogma for many years was that nucleic acids had primarily an informational role. Through a method known as Systematic Evolution of Ligands by EXponential enrichment, termed SELEX, it has become clear that nucleic acids have three dimensional structural diversity not unlike proteins. SELEX is a method for the in vitro evolution of nucleic acid molecules with highly specific binding to target molecules and is described in U.S. patent application Ser. No. 07/536,428, filed Jun. 11, 1990, entitled "Systematic Evolution of Ligands by Exponential Enrichment", now abandoned, U.S. patent application Ser. No. 07/714,131, filed Jun. 10, 1991, entitled "Nucleic Acid Ligands", now U.S. Pat. No. 5,475,096, U.S. patent application Ser. No. 07/931,473, filed Aug. 17, 1992, entitled "Nucleic Acid Ligands", now U.S. Pat. No. 5,270,163 (see also PCT/US91/04078), each of which is specifically incorporated by reference herein. Each of these applications, collectively referred to herein as the SELEX Patent Applications, describes a fundamentally novel method for making a Nucleic Acid Ligand to any desired target molecule. The SELEX process provides a class of products which are referred to as Nucleic Acid Ligands, each ligand having a unique sequence, and which has the property of binding specifically to a desired target compound or molecule. Each SELEX-identified Nucleic Acid Ligand is a specific ligand of a given target compound or molecule. SELEX is based on the unique insight that Nucleic Acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size or composition can serve as targets.

The SELEX method involves selection from a mixture of candidate oligonucleotides and step-wise iterations of binding, partitioning and amplification, using the same general selection scheme, to achieve virtually any desired criterion of binding affinity and selectivity. Starting from a mixture of Nucleic Acids, preferably comprising a segment of randomized sequence, the SELEX method includes steps of contacting the mixture with the target under conditions favorable for binding, partitioning unbound Nucleic Acids from those Nucleic Acids which have bound specifically to target molecules, dissociating the Nucleic Acid-target complexes, amplifying the Nucleic Acids dissociated from the Nucleic Acid-target complexes to yield a ligand-enriched mixture of Nucleic Acids, then reiterating the steps of binding, partitioning, dissociating and amplifying through as many cycles as desired to yield highly specific high affinity Nucleic Acid Ligands to the target molecule.

It has been recognized by the present inventors that the SELEX method demonstrates that Nucleic Acids as chemical compounds can form a wide array of shapes, sizes and configurations, and are capable of a far broader repertoire of binding and other functions than those displayed by Nucleic Acids in biological systems.

The present inventors have recognized that SELEX or SELEX-like processes could be used to identify Nucleic Acids which can facilitate any chosen reaction in a manner similar to that in which Nucleic Acid Ligands can be identified for any given target. In theory, within a Candidate Mixture of approximately $10^{13}$ to $10^{18}$ Nucleic Acids, the present inventors postulate that at least one Nucleic Acid exists with the appropriate shape to facilitate each of a broad variety of physical and chemical interactions.

The basic SELEX method has been modified to achieve a number of specific objectives. For example, U.S. patent application Ser. No. 07/960,093, filed Oct. 14, 1992, entitled "Method for Selecting Nucleic Acids on the Basis of Structure," describes the use of SELEX in conjunction with gel electrophoresis to select Nucleic Acid molecules with specific structural characteristics, such as bent DNA. U.S. patent application Ser. No. 08/123,935, filed Sep. 17, 1993, entitled "Photoselection of Nucleic Acid Ligands," describes a SELEX based method for selecting Nucleic Acid Ligands containing photoreactive groups capable of binding and/or photocrosslinking to and/or photoinactivating a target molecule. U.S. patent application Ser. No. 08/134,028, filed Oct. 7, 1993, entitled "High-Affinity Nucleic Acid Ligands That Discriminate Between Theophylline and Caffeine," describes a method for identifying highly specific Nucleic Acid Ligands able to discriminate between closely related molecules, which can be non-peptidic, termed Counter-SELEX. U.S. patent application Ser. No. 08/143,564, filed Oct. 25, 1993, entitled "Systematic Evolution of Ligands by EXponential Enrichment: Solution SELEX," describes a SELEX-based method which achieves highly efficient partitioning between oligonucleotides having high and low affinity for a target molecule.

The SELEX method encompasses the identification of high-affinity Nucleic Acid Ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified Nucleic Acid Ligands containing modified nucleotides are described in U.S. patent application Ser. No. 08/117,991, filed Sep. 8, 1993, entitled "High Affinity Nucleic Acid Ligands Containing Modified Nucleotides," that describes oligonucleotides containing nucleotide derivatives chemically modified at the 5- and 2'-positions of pyrimidines. U.S. patent application Ser. No. 08/134,028, supra, describes highly specific Nucleic Acid Ligands containing one or more nucleotides modified with 2'-amino (2'-NH$_2$), 2'-fluoro (2'-F), and/or 2'-O-methyl (2'-OMe). U.S. patent application Ser. No. 08/264,029, filed Jun. 22, 1994, entitled "Novel Method of Preparation of 2' Modified Pyrimidine Intramolecular Nucleophilic Displacement", describes oligonucleotides containing various 2'-modified pyrimidines.

The SELEX method encompasses combining selected oligonucleotides with other selected oligonucleotides and non-oligonucleotide functional units as described in U.S. patent application Ser. No. 08/284,063, filed Aug. 2, 1994, entitled "Systematic Evolution of Ligands by Exponential Enrichment: Chimeric SELEX" and U.S. patent application Ser. No. 08/234,997, filed Apr. 28, 1994, entitled "Systematic Evolution of Ligands by Exponential Enrichment: Blended SELEX," respectively. These applications allow the combination of the broad array of shapes and other properties, and the efficient amplification and replication properties, of oligonucleotides with the desirable properties of other molecules. Each of the above described patent applications which describe modifications of the basic SELEX procedure are specifically incorporated by reference herein in their entirety.

B. Lipid Constructs

Lipid Bilayer Vesicles are closed, fluid-filled microscopic spheres which are formed principally from individual molecules having polar (hydrophilic) and non-polar (lipophilic) portions. The hydrophilic portions may comprise phosphato, glycerylphosphato, carboxy, sulfato, amino, hydroxy, choline or other polar groups. Examples of lipophilic-groups are saturated or unsaturated hydrocarbons such as alkyl, alkenyl or other lipid groups. Sterols (e.g., cholesterol) and other pharmaceutically acceptable adjuvants (including anti-oxidants like alpha-tocopherol) may also be included to improve vesicle stability or confer other desirable characteristics.

Liposomes are a subset of these bilayer vesicles and are comprised principally of phospholipid molecules that contain two hydrophobic tails consisting of fatty acid chains. Upon exposure to water, these molecules spontaneously align to form spherical, bilayer membranes with the lipophilic ends of the molecules in each layer associated in the center of the membrane and the opposing polar ends forming the respective inner and outer surface of the bilayer membrane(s). Thus, each side of the membrane presents a hydrophilic surface while the interior of the membrane comprises a lipophilic medium. These membranes may be arranged in a series of concentric, spherical membranes separated by thin strata of water, in a manner not dissimilar to the layers of an onion, around an internal aqueous space. These multilamellar vesicles (MLV) can be converted into small or Unilamellar Vesicles (UV), with the application of a shearing force.

The therapeutic use of liposomes includes the delivery of drugs which are normally toxic in the free form. In the liposomal form, the toxic drug is occluded, and may be directed away from the tissues sensitive to the drug and targeted to selected areas. Liposomes can also be used therapeutically to release drugs over a prolonged period of time, reducing the frequency of administration. In addition, liposomes can provide a method for forming aqueous dispersions of hydrophobic or amphiphilic drugs, which are normally unsuitable for intravenous delivery.

In order for many drugs and imaging agents to have therapeutic or diagnostic potential, it is necessary for them to be delivered to the proper location in the body, and the liposome can thus be readily injected and form the basis for sustained release and drug delivery to specific cell types, or parts of the body. Several techniques can be employed to use liposomes to target encapsulated drugs to selected host tissues, and away from sensitive tissues. These techniques include manipulating the size of the liposomes, their net surface charge, and their route of administration. MLVs, primarily because they are relatively large, are usually rapidly taken up by the reticuloendothelial system (principally the liver and spleen). UVs, on the other hand, have been found to exhibit increased circulation times, decreased clearance rates and greater biodistribution relative to MLVs.

Passive delivery of liposomes involves the use of various routes of administration, e.g., intravenous, subcutaneous, intramuscular and topical. Each route produces differences in localization of the liposomes. Two common methods used to direct liposomes actively to selected target areas involve attachment of either antibodies or specific receptor ligands to the surface of the liposomes. Antibodies are known to have a high specificity for their corresponding antigen and have been attached to the surface of liposomes, but the results have been less than successful in many instances. Some efforts, however, have been successful in targeting liposomes to tumors without the use of antibodies, sec, for example, U.S. Pat. No. 5,019,369.

An area of development aggressively pursued by researchers is the delivery of agents not only to a specific cell type but into the cell's cytoplasm and, further yet, into the nucleus. This is particularly important for the delivery of biological agents such as DNA, RNA, ribozymes and proteins. A promising therapeutic pursuit in this area involves the use of antisense DNA and RNA oligonucleotides for the treatment of disease. However, one major problem encountered in the effective application of antisense technology is that oligonucleotides in their phosphodiester form are quickly degraded in body fluids and by intracellular and extracellular enzymes, such as endonucleases and exonucleases, before the target cell is reached. Intravenous administration also results in rapid clearance from the bloodstream by the kidney, and uptake is insufficient to produce an effective intracellular drug concentration. Liposome encapsulation protects the oligonucleotides from the degradative enzymes, increases the circulation half-life and increases uptake efficiency as a result of phagocytosis of the Liposomes. In this way, oligonucleotides are able to reach their desired target and to be delivered to cells in vivo.

A few instances have been reported where researchers have attached antisense oligonucleotides to Lipophilic Compounds or Non-Immunogenic, High Molecular Weight Compounds. Antisense oligonucleotides, however, are only effective as intracellular agents. Antisense oligodeoxyribonucleotides targeted to the epidermal growth factor (EGF) receptor have been encapsulated into Liposomes linked to folate via a polyethylene glycol spacer (folate-PEG-Liposomes) and delivered into cultured KB cells via folate receptor-mediated endocytosis (Wang et al. (1995) 92:3318-3322). In addition, a Lipophilic Compound covalently attached to an antisense oligonucleotide has been demonstrated in the literature (EP 462 145 B1).

SUMMARY OF THE INVENTION

The present invention provides a method for preparing a therapeutic or diagnostic Complex comprised of a Nucleic Acid Ligand and a Lipophilic Compound or Non-Immunogenic, High Molecular Weight Compound by the method comprising identifying a Nucleic Acid Ligand from a Candidate Mixture of Nucleic Acids where the Nucleic Acid is a ligand of a given target by the method of (a) contacting the Candidate Mixture of Nucleic Acids with the target, (b) partitioning between members of said Candidate Mixture on the basis of affinity to the target, and c) amplifying the selected molecules to yield a mixture of Nucleic Acids enriched for Nucleic Acid sequences with a relatively higher affinity for binding to the target, and associating said identified Nucleic Acid Ligand with a Lipophilic Compound or a Non-Immunogenic, High Molecular Weight Compound.

In another embodiment, this invention provides a method for improving the cellular uptake of a Nucleic Acid Ligand having an intracellular SELEX Target by associating the Nucleic Acid Ligand with a Lipophilic Compound or a Non-Immunogenic, High Molecular Weight Compound to form a Complex comprised of a Nucleic Acid Ligand and a Lipophilic Compound or a Non-Immunogenic, High Molecular Weight Compound and administering the Complex to a patient.

In another embodiment, this invention provides a method for improving the pharmacokinetic properties of a Nucleic Acid Ligand by associating the Nucleic Acid Ligand to a Lipophilic Compound or a Non-Immunogenic, High Molecular Weight Compound to form a Complex comprised of a Nucleic Acid Ligand and a Lipophilic Compound or a Non-Immunogenic, High Molecular Weight Compound and administering the Complex to a patient.

In another embodiment, this invention provides a method for targeting a therapeutic or diagnostic agent to a specific predetermined biological Target in a patient comprising associating the therapeutic or diagnostic agent with a Complex comprised of a Nucleic Acid Ligand and a Lipophilic Compound or Non-Immunogenic, High Molecular Weight Compound, wherein the Nucleic Acid Ligand has a SELEX Target associated with the specific predetermined Target, and the Nucleic Acid Ligand is associated with the exterior of the Complex and administering the Complex to a patient.

It is an object of the present invention to provide Complexes comprising one or more Nucleic Acid Ligands in association with a Lipophilic Compound or Non-Immunogenic, High Molecular Weight Compound and methods for producing the same. It is a further object of the invention to provide one or more Nucleic Acid Ligands in association with a Lipophilic Compound or Non-Immunogenic, High Molecular Weight Compound with Improved Pharmacokinetic Properties. In another aspect of the invention, the Lipophilic Compound is a Lipid Construct. In this embodiment, the Lipid Construct is preferably a Lipid Bilayer Vesicle and most preferably a Liposome. In certain embodiments of the invention the Lipophilic Compound is cholesterol, dialkyl glycerol, or diacyl glycerol. In another embodiment of the invention, the Non-Immunogenic, High Molecular Weight Compound is PEG. In another embodiment of the invention, the Non-Immunogenic, High Molecular Weight Compound is magnetite. In the preferred embodiment, the Nucleic Acid Ligand is identified according to the SELEX method.

In embodiments of the invention directed to Complexes comprising cholesterol, dialkyl glycerol, diacyl glycerol, PEG, or magnetite in association with a Nucleic Acid Ligand or ligands, the Nucleic Acid Ligand or ligands can serve in a targeting capacity.

In embodiments of the invention directed to Complexes comprising a Lipid Construct where the Lipid Construct is of a type that has a membrane defining an interior compartment such as a Lipid Bilayer Vesicle, the Nucleic Acid Ligand in association with the Lipid Construct may be associated with the membrane of the Lipid Construct or encapsulated within the compartment. In embodiments where the Nucleic Acid Ligand is in association with the membrane, the Nucleic Acid Ligand can associate with the interior-facing or exterior-facing part of the membrane, such that the Nucleic Acid Ligand is projecting in to or out of the vesicle. In embodiments where the Nucleic Acid Ligand is projecting out of the Complex, the Nucleic Acid Ligand can serve in a targeting capacity. Non-Immunogenic, High Molecular Weight Compounds can also be associated with the membrane. In one embodiment, the Nucleic Acid Ligand may be associated with a Non-Immunogenic, High Molecular Weight Compound which is associated with the membrane. The membrane may have associated with it additional Non-Immunogenic, High Molecular Weight Compounds not associated with a Nucleic Acid Ligand.

In embodiments where the Nucleic Acid Ligand of the Complex serves in a targeting capacity, the Complex can incorporate or have associated with it therapeutic or diagnostic agents. In one embodiment, the therapeutic agent is a drug. In an alternative embodiment, the therapeutic or diagnostic agent is one or more additional Nucleic Acid Ligands. Nucleic Acid Ligands specific for different targets can project from the external surface of the Complex. The Complex can project from the external surface one or more Nucleic Acid Ligands which are specific for different SELEX Targets on the same Target.

These and other objects, as well as the nature, scope and utilization of this invention, will become readily apparent to those skilled in the art from the following description and the appended claims.

DETAILED DESCRIPTION OF THE INVENTION

Definitions

Figure 1A:
FIGS. 1A-1Y show the molecular descriptions of NX229, NX232, NX253, NX256, 225T3, 225T3N, T-P4, NX-256-PEG-20,000, 225T3N-PEG-3400, T-P4-PEG-(20,000 or 10,000), NX268, NX191, JW966, NX278, JW986, NX213, NX244, JW1130, NX287, JW1336-20K PEG, JW1379, JW1380, scNX278, JW986-PEG-(10,000, 20,000, or 40,000), and JW1336 (SEQ ID NOS:6-30). A lower case letter preceding a nucleotide indicates the following: m=2'-O-Methyl, a=2'-amino, r=ribo, and f=2'-fluoro. No letter preceding a nucleotide indicates a deoxyribonucleotide (2'H). An S following a nucleotide denotes a backbone modification consisting of a phosphorothioate internucleoside linkage.

"Covalent Bond" is the chemical bond formed by the sharing of electrons.

"Non-Covalent Interactions" are means of holding together molecular entities by interactions other than Covalent Bonds including ionic interactions and hydrogen bonds.

"Lipid Constructs," for purposes of this invention, are structures containing lipids, phospholipids, or derivatives thereof comprising a variety of different structural arrangements which lipids are known to adopt in aqueous suspension. These structures include, but are not limited to, Lipid Bilayer Vesicles, micelles, Liposomes, emulsions, lipid ribbons or sheets, and may be complexed with a variety of drugs and adjuvants which are known to be pharmaceutically acceptable. Common adjuvants include cholesterol and alpha-tocopherol, among others. The Lipid Constructs may be used alone or in any combination which one skilled in the art would appreciate to provide the characteristics desired for a particular application. In addition, the technical aspects of Lipid Constructs and Liposome formation are well known in the art and any of the methods commonly practiced in the field may be used for the present invention.

"Lipophilic Compounds" are compounds which have the propensity to associate with or partition into lipid and/or other materials or phases with low dielectric constants, including structures that are comprised substantially of lipophilic components. Lipophilic Compounds include Lipid Constructs as well as non-lipid containing compounds that have the propensity to associate with lipid (and/or other materials or phases with low dielectric constants). Cholesterol, phospholipid, and dialkyl glycerol are further examples of Lipophilic Compounds.

"Complex" as used herein describes the molecular entity formed by the association of a Nucleic Acid Ligand with a Lipophilic Compound or Non-Immunogenic, High Molecular Weight Compound. The association can be through either Covalent Bonds or Non-Covalent Interactions.

"Nucleic Acid Ligand" as used herein is a non-naturally occurring Nucleic Acid having a desirable action on a SELEX Target. A desirable action includes, but is not limited to, binding of the SELEX Target, catalytically changing the SELEX Target, reacting with the SELEX Target in a way which modifies/alters the SELEX Target or the functional activity of the SELEX Target, covalently attaching to the SELEX Target as in a suicide inhibitor, facilitating the reaction between the Target and another molecule. In the preferred embodiment, the action is specific binding affinity for a Target molecule, such Target molecule being a three dimensional chemical structure other than a polynucleotide that binds to the Nucleic Acid Ligand through a mechanism which predominantly depends on Watson/Crick base pairing or triple helix binding, wherein the Nucleic Acid Ligand is not a Nucleic Acid having the known physiological function of being bound by the Target molecule. In preferred embodiments of the invention, the Nucleic Acid Ligand of the Complexes of the invention are identified by the SELEX methodology. Nucleic Acid Ligands include Nucleic Acids that are identified from a Candidate Mixture of Nucleic Acids, said Nucleic Acid being a ligand of a given Target, by the method comprising a) contacting the Candidate Mixture with the Target, wherein Nucleic Acids having an increased affinity to the Target relative to the Candidate Mixture may be partitioned from the remainder of the Candidate Mixture; b) partitioning the increased affinity Nucleic Acids from the remainder of the Candidate Mixture; and c) amplifying the increased affinity Nucleic Acids to yield a ligand-enriched mixture of Nucleic Acids.

"Candidate Mixture" is a mixture of Nucleic Acids of differing sequence from which to select a desired ligand. The source of a Candidate Mixture can be from naturally-occurring Nucleic Acids or fragments thereof, chemically synthesized Nucleic Acids, enzymatically synthesized Nucleic Acids or Nucleic Acids made by a combination of the foregoing techniques. In a preferred embodiment, each Nucleic Acid has fixed sequences surrounding a randomized region to facilitate the amplification process.

"Nucleic Acid" means either DNA, RNA, single-stranded or double-stranded and any chemical modifications thereof. Modifications include, but are not limited to, those which provide other chemical groups that incorporate additional charge, polarizability, hydrogen bonding, electrostatic interaction, and fluxionality to the Nucleic Acid Ligand bases or to the Nucleic Acid Ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodouracil, backbone modifications such as internucleoside phosphorothioate linkages, methylations, unusual base-pairing combinations such as the isobases isocytidine and isoguanidine and the like. Modifications can also include 3' and 5' modifications such as capping.

"Non-Immunogenic, High Molecular Weight Compound" is a compound of approximately 1000 Da or more that typically does not generate an immunogenic response. For the purposes of this invention, an immunogenic response is one that causes the organism to make antibody proteins. Examples of Non-Immunogenic, High Molecular Weight Compounds include polyethylene glycol (PEG); polysaccharides, such as dextran; polypeptides, such as albumin; and magnetic structures; such as magnetite. In certain embodiments, the Non-Immunogenic, High Molecular Weight Compound can also be a Nucleic Acid Ligand.

"Lipid Bilayer Vesicles" are closed, fluid-filled microscopic spheres which are formed principally from individual molecules having polar (hydrophilic) and non-polar (lipophilic) portions. The hydrophilic portions may comprise phosphato, glycerylphosphato, carboxy, sulfato, amino, hydroxy, choline and other polar groups. Examples of non-polar groups are saturated or unsaturated hydrocarbons such as alkyl, alkenyl or other lipid groups. Sterols (e.g., cholesterol) and other pharmaceutically acceptable adjuvants (including anti-oxidants like alpha-tocopherol) may also be included to improve vesicle stability or confer other desirable characteristics.

"Liposomes" are a subset of bilayer vesicles and are comprised principally of phospholipid molecules which contain two hydrophobic tails consisting of long fatty acid chains. Upon exposure to water, these molecules spontaneously align to form a bilayer membrane with the lipophilic ends of the molecules in each layer associated in the center of the membrane and the opposing polar ends forming the respective inner and outer surface of the bilayer membrane. Thus, each side of the membrane presents a hydrophilic surface while the interior of the membrane comprises a lipophilic medium. These membranes when formed are generally arranged in a system of concentric closed membranes separated by interlamellar aqueous phases, in a manner not dissimilar to the layers of an onion, around an internal aqueous space. These multilamellar vesicles (MLV) can be converted into small or unilamellar vesicles (UV), with the application of a shearing force.

"Cationic Liposome" is a Liposome that contains lipid components that have an overall positive charge at physiological pH.

"SELEX" methodology involves the combination of selection of Nucleic Acid Ligands which interact with a Target in a desirable manner, for example binding to a protein, with amplification of those selected Nucleic Acids. Iterative cycling of the selection/amplification steps allows selection of one or a small number of Nucleic Acids which interact most strongly with the Target from a pool which contains a very large number of Nucleic Acids. Cycling of the selection/amplification procedure is continued until a selected goal is achieved. In the present invention, the SELEX methodology can be employed to obtain a Nucleic Acid Ligand to a desirable Target.

The SELEX methodology is described in the SELEX Patent Applications.

"SELEX Target" means any compound or molecule of interest for which a ligand is desired. A Target can be a protein (such as VEGF, thrombin, and selectin), peptide, carbohydrate, polysaccharide, glycoprotein, hormone, receptor, antigen, antibody, virus, substrate, metabolite, transition state analog, cofactor, inhibitor, drug, dye, nutrient, growth factor, etc. without limitation. The terms "SELEX Target" and "Target" can be used interchangeably herein. It will be clear from the sentence context whether or not "Target" means "SELEX Target."

"Target" means a preselected location in a biological system including tissues, organs, cells, intracellular compartments, extracellular components. The latter include hormones (endocrine paracrine, autocrine), enzymes, neurotransmitters and constituents of physiological cascade phenomena (e.g., blood coagulation, complement, etc.).

"Improved Pharmacokinetic Properties" means that the Nucleic Acid Ligand in association with the Non-Immunogenic, High Molecular Weight Compound or Lipophilic Compound shows a longer circulation half-life in vivo relative to the same Nucleic Acid Ligand not in association with a Lipophilic Compound or Non-Immunogenic, High Molecular Weight Compound or other pharmacokinetic benefits such as improved Target to non-Target concentration ratio.

"Linker" is a molecular entity that connects two or more molecular entities through covalent or Non-Covalent Interactions.

"Spacer" is a Linker of the size that allows spatial separation of two or more molecular entities in a manner that preserves the functional properties of one or more of the molecular entities.

It is an object of the present invention to provide Complexes comprising one or more Nucleic Acid Ligands in association with a Lipophilic Compound or Non-Immunogenic, High Molecular Weight Compound. Such Complexes have one or more of the following advantages over a Nucleic Acid Ligand not in association with a Lipophilic Compound or Non-Immunogenic, High Molecular Weight Compound: 1) Improved Pharmacokinetic Properties. 2) improved capacity for intracellular delivery, or 3) improved capacity for targeting.

The Complexes of the present invention may benefit from one, two, or all three of these advantages. The Complexes of the present invention may contain different Nucleic Acid Ligands serving totally different purposes in the Complex. For example, a Complex of the present invention may be comprised of a) a Liposome, b) a Nucleic Acid Ligand that is targeted to an intracellular SELEX Target that is encapsulated within the interior of the Liposome, and c) a Nucleic Acid Ligand that is targeted to a particular cell type that is associated with and projecting from the exterior surface of the Liposome. In such a case, the Complex will 1) have Improved Pharmacokinetic Properties due to the presence of the Liposome, 2) have enhanced capacity for intracellular delivery of the encapsulated Nucleic Acid Ligand due to the properties of the Liposome, and 3) be specifically targeted to the preselected location in vivo by the exteriorly associated Nucleic Acid Ligand.

In another embodiment, the Complex of the present invention is comprised of a Nucleic Acid Ligand covalently attached to a Lipophilic Compound such as cholesterol, dialkyl glycerol, diacyl glycerol, or a Non-Immunogenic, High Molecular Weight Compound such as polyethylene glycol (PEG). In these cases, the pharmacokinetic properties of the Complex will be enhanced relative to the Nucleic Acid Ligand alone. In still other embodiments, the Complex of the present invention is comprised of a Nucleic Acid Ligand encapsulated inside a Liposome, and enhanced intracellular uptake of the Nucleic Acid Ligand is seen over the un-Complexed Nucleic Acid Ligand.

In certain embodiments of the invention, the Complex of the present invention is comprised of a Nucleic Acid Ligand attached to one (dimeric) or more (multimeric) other Nucleic Acid Ligands. The Nucleic Acid Ligand can be to the same or different SELEX Target. In embodiments where there are multiple Nucleic Acid Ligands to the same SELEX Target, there is an increase in avidity due to multiple binding interactions with the SELEX Target. Furthermore, in embodiments of the invention where the Complex is comprised of a Nucleic Acid Ligand attached to one or more other Nucleic Acid Ligands, the pharmacokinetic properties of the Complex will be improved relative to one Nucleic Acid Ligand alone.

The Lipophilic Compound or Non-Immunogenic, High Molecular Weight Compound can be covalently bonded or associated through Non-Covalent Interactions with the Nucleic Acid Ligand(s). In embodiments where the Lipophilic Compound is cholesterol, dialkyl glycerol, diacyl glycerol, or the Non-Immunogenic, High Molecular Weight Compound is PEG, a covalent association with the Nucleic Acid Ligand(s) is preferred. In embodiments where the Lipophilic Compound is a Cationic Liposome or where the Nucleic Acid Ligands are encapsulated within the Liposome, a non-covalent association with the Nucleic Acid Ligand(s) is preferred. In embodiments where covalent attachment is employed, the Lipophilic Compound or Non-Immunogenic, High Molecular Weight Compound may be covalently bound to a variety of positions on the Nucleic Acid Ligand, such as to an exocyclic amino group on the base, the 5-position of a pyrimidine nucleotide, the 8-position of a purine nucleotide, the hydroxyl group of the phosphate, or a hydroxyl group or other group at the 5' or 3' terminus of the Nucleic Acid Ligand. Preferably, however, it is bonded to the 5' or 3' hydroxyl group thereof. Attachment of the Nucleic Acid Ligand to other components of the Complex can be done directly or with the utilization of Linkers or Spacers.

The Lipophilic Compound or Non-Immunogenic, High Molecular Weight Compound can associate through Non-Covalent Interactions with the Nucleic Acid Ligand(s). For example, in one embodiment of the present invention, the Nucleic Acid Ligand is encapsulated within the internal compartment of the Lipophilic Compound. In another embodiment of the present invention, the Nucleic Acid Ligand associates with the Lipophilic Compound through electrostatic interactions. For instance, a Cationic Liposome can associate with an anionic Nucleic Acid Ligand. Another example of a Non-Covalent Interaction through ionic attractive forces is one in which a portion of the Nucleic Acid Ligand hybridizes through Watson-Crick base-pairing or triple helix base-pairing to an oligonucleotide which is associated with a Lipophilic Compound or Non-Immunogenic, High Molecular Weight Compound.

One problem encountered in the therapeutic and in vivo diagnostic use of Nucleic Acids is that oligonucleotides in their phosphodiester form may be quickly degraded in body fluids by intracellular and extracellular enzymes such as endonucleases and exonucleases before the desired effect is manifest. Certain chemical modifications of the Nucleic Acid Ligand can be made to increase the in vivo stability of the Nucleic Acid Ligand or to enhance or to mediate the delivery of the Nucleic Acid Ligand. Modifications of the Nucleic Acid Ligands contemplated in this invention include, but are not limited to, those which provide other chemical groups that incorporate additional charge, polarizability, hydrophobicity, hydrogen bonding, electrostatic interaction, and fluxionality to the Nucleic Acid Ligand bases or to the Nucleic Acid Ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, unusual base-pairing combinations such as the isobases isocytidine and isoguanidine and the like. Modifications can also include 3' and 5' modifications such as capping.

Where the Nucleic Acid Ligands are derived by the SELEX method, the modifications can be pre- or post-SELEX modifications. Pre-SELEX modifications yield Nucleic Acid Ligands with both specificity for their SELEX Target and improved in vivo stability. Post-SELEX modifications made to 2'-OH Nucleic Acid Ligands can result in improved in vivo stability without adversely affecting the binding capacity of the Nucleic Acid Ligands. The preferred modifications of the Nucleic Acid Ligands of the subject invention are 5' and 3' phosphorothioate capping or 3'3' inverted phosphodiester linkage at the 3' end. For RNA ligands, additional 2' amino ($2'-NH_2$) modification of some or all of the nucleotides is preferred.

In another aspect of the present invention, the association of the Nucleic Acid Ligand with a Lipophilic Compound or Non-Immunogenic, High Molecular Weight Compound, results in Improved Pharmacokinetic Properties (i.e., slower clearance rate) relative to the Nucleic Acid Ligand not in association with a Lipophilic Compound or Non-Immunogenic, High Molecular Weight Compound. In one embodiment of the invention, the Complex includes a Lipid Construct. The Complex with the Nucleic Acid Ligand can be formed through covalent or Non-Covalent Interactions. In a preferred embodiment, the Lipid Construct is a Lipid Bilayer Vesicle. In the most preferred embodiment, the Lipid Construct is a Liposome.

In certain embodiments of this invention, the Complex comprises a Liposome with a targeting Nucleic Acid Ligand projecting out of the Liposome. In embodiments where there are multiple Nucleic Acid Ligands to the same Target, there is an increase in avidity due to multiple binding interactions with the Target.

Liposomes for use in the present invention can be prepared by any of the various techniques presently known in the art or subsequently developed. Typically, they are prepared from a phospholipid, for example, distearoyl phosphatidylcholine, and may include other materials such as neutral lipids, for example, cholesterol, and also surface modifiers such as positively charged (e.g., sterylamine or aminomannose or aminomannitol derivatives of cholesterol) or negatively charged (e.g., dicetyl phosphate, phosphatidyl glycerol) compounds. Multilamellar Liposomes can be formed by the conventional technique, that is, by depositing a selected lipid on the inside wall of a suitable container or vessel by dissolving the lipid in an appropriate solvent, and then evaporating the solvent to leave a thin film on the inside of the vessel or by spray drying. An aqueous phase is then added to the vessel with a swirling or vortexing motion which results in the formation of MLVs. UVs can then be formed by homogenization, sonication or extrusion (through filters) of MLV's. In addition, UVs can be formed by detergent removal techniques.

In certain embodiments of this invention, the Complex comprises a Liposome with a targeting Nucleic Acid Ligand(s) associated with the surface of the Liposome and an encapsulated therapeutic or diagnostic agent. Preformed Liposomes can be modified to associate with the Nucleic Acid Ligands. For example, a Cationic Liposome associates through electrostatic interactions with the Nucleic Acid Ligand. Alternatively, a Nucleic Acid Ligand attached to a Lipophilic Compound, such as cholesterol, can be added to preformed Liposomes whereby the cholesterol becomes associated with the liposomal membrane. Alternatively, the Nucleic Acid Ligand can be associated with the Liposome during the formulation of the Liposome. Preferably, the Nucleic Acid Ligand is associated with the Liposome by loading into preformed Liposomes.

It is well known in the art that Liposomes are advantageous for encapsulating or incorporating a wide variety of therapeutic and diagnostic agents. Any variety of compounds can be enclosed in the internal aqueous compartment of the Liposomes. Illustrative therapeutic agents include antibiotics, antiviral nucleosides, antifungal nucleosides, metabolic regulators, immune modulators, chemotherapeutic drugs, toxin antidotes, DNA, RNA, antisense oligonucleotides, etc. By the same token, the Lipid Bilayer Vesicles may be loaded with a diagnostic radionuclide (e.g., Indium 111, Iodine 131, Yttrium 90, Phosphorous 32, or gadolinium) and fluorescent materials or other materials that are detectable in in vitro and in vivo applications. It is to be understood that the therapeutic or diagnostic agent can be encapsulated by the Liposome walls in the aqueous interior. Alternatively, the carried agent can be a part of, that is, dispersed or dissolved in the vesicle wall-forming materials.

During Liposome formation, water soluble carrier agents may be encapsulated in the aqueous interior by including them in the hydrating solution, and lipophilic molecules incorporated into the lipid bilayer by inclusion in the lipid formulation. In the case of certain molecules (e.g., cationic or anionic lipophilic drugs), loading of the drug into preformed Liposomes may be accomplished, for example, by the methods described in U.S. Pat. No. 4,946,683, the disclosure of which is incorporated herein by reference. Following drug encapsulation, the Liposomes are processed to remove unencapsulated drug through processes such as gel chromatography or ultrafiltration. The Liposomes are then typically sterile filtered to remove any microorganisms which may be present in the suspension. Microorganisms may also be removed through aseptic processing.

If one wishes to encapsulate large hydrophilic molecules with Liposomes, larger unilamellar vesicles can be formed by methods such as the reverse-phase evaporation (REV) or solvent infusion methods. Other standard methods for the formation of Liposomes are known in the art, for example, methods for the commercial production of Liposomes include the homogenization procedure described in U.S. Pat. No. 4,753,788 and the thin-film evaporation method described in U.S. Pat. No. 4,935,171, which are incorporated herein by reference.

It is to be understood that the therapeutic or diagnostic agent can also be associated with the surface of the Lipid Bilayer Vesicle. For example, a drug can be attached to a phospholipid or glyceride (a prodrug). The phospholipid or glyceride portion of the prodrug can be incorporated into the lipid bilayer of the Liposome by inclusion in the lipid formulation or loading into preformed Liposomes (see U.S. Pat. Nos. 5,194,654 and 5,223,263, which are incorporated by reference herein).

It is readily apparent to one skilled in the art that the particular Liposome preparation method will depend on the intended use and the type of lipids used to form the bilayer membrane.

A Nucleic Acid Ligand or ligands in association with a Lipophilic Compound or Non-Immunogenic, High Molecular Weight Compound may enhance the intracellular delivery of the Nucleic Acid Ligand(s) over non-associated Nucleic Acid Ligand(s). The efficiency of delivery of the Complex to cells may be optimized by using lipid formulations and conditions known to enhance fusion of Liposomes with cellular membranes. For example, certain negatively charged lipids such as phosphatidylglycerol and phosphatidylserine promote fusion, especially in the presence of other fusogens (e.g., multivalent cations like Ca2+, free fatty acids, viral fusion proteins, short chain PEG, lysolecithin, detergents and surfactants). Phosphatidylethanolamine may also be included in the Liposome formulation to increase membrane fusion and, concomitantly, enhance cellular delivery. In addition, free fatty acids and derivatives thereof, containing, for example, carboxylate moieties, may be used to prepare pH-sensitive Liposomes which are negatively charged at higher pH and neutral or protonated at lower pH. Such pH-sensitive Liposomes are known to possess a greater tendency to fuse.

In the preferred embodiment, the Nucleic Acid Ligands of the present invention are derived from the SELEX methodology. SELEX is described in U.S. patent application Ser. No. 07/536,428, entitled Systematic Evolution of Ligands by EXponential Enrichment, now abandoned, U.S. patent application Ser. No. 07/714,131, filed Jun. 10, 1991, entitled Nucleic Acid Ligands, now U.S. Pat. No. 5,475,096, U.S. patent application Ser. No. 07/931,473, filed Aug. 17, 1992, entitled Nucleic Acid Ligands, now U.S. Pat. No. 5,270,163 (see also PCT/US91/04078). These applications, each specifically incorporated herein by reference, are collectively called the SELEX Patent Applications.

The SELEX process provides a class of products which are Nucleic Acid molecules, each having a unique sequence, and each of which has the property of binding specifically to a desired Target compound or molecule. Target molecules are preferably proteins, but can also include among others carbohydrates, peptidoglycans and a variety of small molecules. SELEX methodology can also be used to Target biological structures, such as cell surfaces or viruses, through specific interaction with a molecule that is an integral part of that biological structure.

In its most basic form, the SELEX process may be defined by the following series of steps:

1) A Candidate Mixture of Nucleic Acids of differing sequence is prepared. The Candidate Mixture generally includes regions of fixed sequences (i.e., each of the members of the Candidate Mixture contains the same sequences in the same location) and regions of randomized sequences. The fixed sequence regions are selected either: (a) to assist in the amplification steps described below, (b) to mimic a sequence known to bind to the Target, or (c) to enhance the concentration of a given structural arrangement of the Nucleic Acids in the Candidate Mixture. The randomized sequences can be totally randomized (i.e., the probability of finding a base at any position being one in four) or only partially randomized (e.g., the probability of finding a base at any location can be selected at any level between 0 and 100 percent).

2) The Candidate Mixture is contacted with the selected Target under conditions favorable for binding between the Target and members of the Candidate Mixture. Under these circumstances, the interaction between the Target and the Nucleic Acids of the Candidate Mixture can be considered as forming Nucleic Acid-target pairs between the Target and those Nucleic Acids having the strongest affinity for the Target.

3) The Nucleic Acids with the highest affinity for the target are partitioned from those Nucleic Acids with lesser affinity to the target. Because only an extremely small number of sequences (and possibly only one molecule of Nucleic Acid) corresponding to the highest affinity Nucleic Acids exist in the Candidate Mixture, it is generally desirable to set the partitioning criteria so that a significant amount of the Nucleic Acids in the Candidate Mixture (approximately 5-50%) are retained during partitioning.

4) Those Nucleic Acids selected during partitioning as having the relatively higher affinity for the target are then amplified to create a new Candidate Mixture that is enriched in Nucleic Acids having a relatively higher affinity for the target.

5) By repeating the partitioning and amplifying steps above, the newly formed Candidate Mixture contains fewer and fewer unique sequences, and the average degree of affinity of the Nucleic Acids to the target will generally increase. Taken to its extreme, the SELEX process will yield a Candidate Mixture containing one or a small number of unique Nucleic Acids representing those Nucleic Acids from the original Candidate Mixture having the highest affinity to the target molecule.

The basic SELEX method has been modified to achieve a number of specific objectives. For example, U.S. patent application Ser. No. 07/960,093, filed Oct. 14, 1992, entitled "Method for Selecting Nucleic Acids on the Basis of Structure", describes the use of SELEX in conjunction with gel electrophoresis to select Nucleic Acid molecules with specific structural characteristics, such as bent DNA. U.S. patent application Ser. No. 08/123,935, filed Sep. 17, 1993, entitled "Photoselection of Nucleic Acid Ligands" describes a SELEX based method for selecting Nucleic Acid Ligands containing photoreactive groups capable of binding and/or photocrosslinking to and/or photoinactivating a target molecule. U.S. patent application Ser. No. 08/134,028, filed Oct. 7, 1993, entitled "High-Affinity Nucleic Acid Ligands That Discriminate Between Theophylline and Caffeine", describes a method for identifying highly specific Nucleic Acid Ligands able to discriminate between closely related molecules, termed Counter-SELEX. U.S. patent application Ser. No. 08/143,564, filed Oct. 25, 1993, entitled "Systematic Evolution of Ligands by EXponential Enrichment: Solution SELEX", describes a SELEX-based method which achieves highly efficient partitioning between oligonucleotides having high and low affinity for a target molecule. U.S. patent application Ser. No. 07/964,624, filed Oct. 21, 1992, entitled "Methods of Producing Nucleic Acid Ligands" describes methods for obtaining improved Nucleic Acid Ligands after SELEX has been performed. U.S. patent application Ser. No. 08/400,440, filed Mar. 8, 1995, entitled "Systematic Evolution of Ligands by EXponential Enrichment: Chemi-SELEX", describes methods for covalently linking a ligand to its target.

The SELEX method encompasses the identification of high-affinity Nucleic Acid Ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified Nucleic Acid Ligands containing modified nucleotides are described in U.S. patent application Ser. No. 08/117,991, filed Sep. 8, 1993, entitled "High Affinity Nucleic Acid Ligands Containing Modified Nucleotides", that describes oligonucleotides containing nucleotide derivatives chemically modified at the 5- and 2'-positions of pyrimidines. U.S. patent application Ser. No. 08/134,028, supra, describes highly specific Nucleic Acid Ligands containing one or more nucleotides modified with 2'-amino (2'-$NH_2$), 2'-fluoro (2'-F), and/or 2'-O-methyl (2'-OMe). U.S. patent application Ser. No. 08/264,029, filed Jun. 22, 1994, entitled "Novel Method of Preparation of 2' Modified Pyrimidine Intramolecular Nucleophilic Displacement", describes oligonucleotides containing various 2'-modified pyrimidines.

The SELEX method encompasses combining selected oligonucleotides with other selected oligonucleotides and non-oligonucleotide functional units as described in U.S. patent application Ser. No. 08/284,063, filed Aug. 2, 1994, entitled "Systematic Evolution of Ligands by Exponential Enrichment: Chimeric SELEX" and U.S. patent application Ser. No. 08/234,997, filed Apr. 28, 1994, entitled "Systematic Evolution of Ligands by Exponential Enrichment: Blended SELEX", respectively. These applications allow the combination of the broad array of shapes and other properties, and the efficient amplification and replication properties, of oligonucleotides with the desirable properties of other molecules. Each of the above described patent applications which describe modifications of the basic SELEX procedure are specifically incorporated by reference herein in their entirety.

SELEX identifies Nucleic Acid Ligands that are able to bind targets with high affinity and with outstanding specificity, which represents a singular achievement that is unprecedented in the field of Nucleic Acids research. These characteristics are, of course, the desired properties one skilled in the art would seek in a therapeutic or diagnostic ligand.

In order to produce Nucleic Acid Ligands desirable for use as a pharmaceutical, it is preferred that the Nucleic Acid Ligand (1) binds to the target in a manner capable of achieving the desired effect on the target; (2) be as small as possible to obtain the desired effect; (3) be as stable as possible; and (4) be a specific ligand to the chosen target. In most situations, it is preferred that the Nucleic Acid Ligand has the highest possible affinity to the target. Additionally, Nucleic Acid Ligands can have facilitating properties.

In co-pending and commonly assigned U.S. patent application Ser. No. 07/964,624, filed Oct. 21, 1992 ('624), methods are described for obtaining improved Nucleic Acid Ligands after SELEX has been performed. The '624 application, entitled Methods of Producing Nucleic Acid Ligands, is specifically incorporated herein by reference.

In embodiments where the Nucleic Acid Ligand(s) can serve in a targeting capacity, the Nucleic Acid Ligands adopt a three dimensional structure that must be retained in order for the Nucleic Acid Ligand to be able to bind its target. In addition, the Nucleic Acid Ligand must be properly oriented with respect to the surface of the Complex so that its Target binding capacity is not compromised. This can be accomplished by attaching the Nucleic Acid Ligand at a position that is distant from the binding portion of the Nucleic Acid Ligand. The three dimensional structure and proper orientation can also be preserved by use of a Linker or Spacer as described supra.

Any variety of therapeutic or diagnostic agents can be attached, encapsulated, or incorporated into the Complex as discussed supra for targeted delivery by the Complex. In embodiments where the Complex is comprised of a Liposome and a Nucleic Acid Ligand, for example, a fungi-specific Nucleic Acid Ligand exposed on the surface of the Complex could Target a fungal cell for delivery of a fungicide (e.g., amphotericin B). Alternatively, a chemotherapeutic agent can be delivered to tumor cells via a Nucleic Acid Ligand to a tumor antigen.

In an alternative embodiment, the therapeutic or diagnostic agent to be delivered to the Target cell could be another Nucleic Acid Ligand. For example, a Nucleic Acid Ligand that binds to a tumor antigen could be presented to the outside of the Complex, and a Nucleic Acid Ligand that binds to and inhibits the mutated isoform of an intracellular Target such as p21, the protein product of the ras gene, could be the agent to be delivered.

It is further contemplated by this invention that the agent to be delivered can be incorporated into the Complex in such a way as to be associated with the outside surface of the Complex. (e.g., a prodrug, receptor antagonist, or radioactive substance for treatment or imaging). As with the Nucleic Acid Ligand, the agent can be associated through covalent or Non-Covalent Interactions. The Complex would provide targeted delivery of the agent extracellularly, with the Liposome serving as a Linker.

In another embodiment, a Non-Immunogenic, High Molecular Weight Compound (e.g., PEG) can be attached to the Liposome to provide Improved Pharmacokinetic Properties for the Complex. Nucleic Acid Ligands may be attached to the Liposome membrane as described supra or may be attached to a Non-Immunogenic, High Molecular Weight Compound which in turn is attached to the membrane. In this way, the Complex may be shielded from blood proteins and thus be made to circulate for extended periods of time while the Nucleic Acid Ligand is still sufficiently exposed to make contact with and bind to its SELEX Target.

In one embodiment of this invention, the Nucleic Acid Ligand presented on the outside of the Complex can Target circulating proteins (e.g., antibodies, growth factors, protein hormones) for removal by the reticuloendothelial system (i.e., liver and spleen). As an example, the treatment of autoimmune diseases may be possible by such a Complex. Autoimmune diseases are the result of a failure of an organism's immune system to avoid recognition of self due to production of autoantibodies and autoreactive T cells. The attack by the immune system on host cells can result in a large number of disorders including neural diseases, such as multiple sclerosis and myasthenia gravis; diseases of the joints, such as rheumatoid arthritis; attacks on Nucleic Acids, as observed with systemic lupus erythematosus; and such other diseases associated with various organs, as psoriasis, juvenile onset diabetes, Sjogren's disease, and Graves disease. As it has been found that Liposomes associated with proteins are generally cleared by the reticuloendothelial system (i.e., spleen and liver) faster than Liposomes without associated proteins, Nucleic Acid Ligands complexed with a Liposome, can be used for removal of autoantibodies by the reticuloendothelial system.

In another embodiment of the present invention, Nucleic Acid Ligands specific for the same SELEX Target are attached to the surface of the same Liposome. This provides the possibility of bringing the same SELEX Targets in close proximity to each other and can be used to generate specific interactions between the same SELEX Targets. For example, Nucleic Acid Ligands to a tyrosine kinase receptor attached to a Liposome would bring the receptors in close proximity to one another. This would facilitate autophosphorylation which would initiate a signal transduction cascade.

In an alternative embodiment of the present invention, Nucleic Acid Ligands specific for different SELEX Targets are attached to the surface of the same Liposome. This provides the possibility of bringing the distinct Targets in close proximity to each other and can be used to generate specific interactions between the Targets. For example, Nucleic Acid Ligands specific for a tumor marker or antigen and Nucleic Acid Ligands specific for a T-cell receptor would bring the T-cells in close proximity to the tumor. In addition to using the Liposome as a way of bringing Targets in close proximity, agents could be encapsulated in the Liposome (e.g., immune system modulator) to increase the intensity of the interaction (e.g., increase the T-cell immune response).

In instances where it is difficult to identify biomolecules that are unique to a cellular Target of interest, specificity may be obtained by having Nucleic Acid Ligands that are specific for two or more markers to the Target associated with the Complex. In this scenario, it is expected that the best Nucleic Acid Ligands would have low or medium affinity for their respective Targets. The use of Nucleic Acid Ligands of this type are recommended since high affinity Nucleic Acid Ligands would lead to the association of drug with all cells possessing either marker protein, thereby reducing specificity. With lower affinity ligands, avidity is required to provide the necessary specificity.

The Liposome/Nucleic Acid Ligand Complex also allows for the possibility of multiple binding interactions to the Target. This, of course, depends on the number of Nucleic Acid Ligands per Complex and mobility of the Nucleic Acid Ligands and receptors in their respective membranes. Since the effective binding constant may increase as the product of the binding constant for each site, there is a substantial advantage to having multiple binding interactions. In other words, by having many. Nucleic Acid Ligands attached to the Liposome, and therefore creating multivalency, the effective affinity (i.e., the avidity) of the multimeric Complex for its Target may become as good as the product of the binding constant for each site.

In certain embodiments of the invention, the Complex of the present invention is comprised of a Nucleic Acid Ligand attached to a Lipophilic Compound such as cholesterol, or dialkyl glycerol, or diacyl glycerol. In this case, the pharmacokinetic properties of the Complex will be improved relative to the Nucleic Acid Ligand alone. As discussed supra, cholesterol may be covalently bound to the Nucleic Acid Ligand at numerous positions on the Nucleic Acid Ligand. In another embodiment of the invention, the Complex may further comprise a Lipid Construct such as a Liposome. In this embodiment, the cholesterol can assist in the incorporation of the Nucleic Acid Ligand into the Liposome due to the propensity for cholesterol to associate with other Lipophilic Compounds. The cholesterol in association with a Nucleic Acid Ligand can be incorporated into the lipid bilayer of the Liposome by inclusion in the formulation or by loading into preformed Liposomes. In the preferred embodiment, the cholesterol/Nucleic Acid Ligand Complex is associated with a preformed Liposome. The cholesterol can associate with the membrane of the Liposome in such a way so as the Nucleic Acid Ligand is projecting into or out of the Liposome. In embodiments where the Nucleic Acid Ligand is projecting out of the Complex, the Nucleic Acid Ligand can serve in a targeting capacity.

In other embodiments, the Complex of the present invention is comprised of a Nucleic Acid Ligand attached to a Non-Immunogenic, High Molecular Weight Compound such as PEG, dialkyl glycerol, diacyl glycerol, or cholesterol. In this embodiment, the pharmacokinetic properties of the Complex are improved relative to the Nucleic Acid Ligand alone. As discussed supra, the association could be through Covalent Bonds or Non-Covalent Interactions. In the preferred embodiment, the Nucleic Acid Ligand is associated with the PEG, dialkyl glycerol, diacyl glycerol, or a cholesterol molecule through Covalent Bonds. Also, as discussed supra, where covalent attachment is employed, PEG, dialkyl glycerol, diacyl glycerol, or cholesterol may be covalently bound to a variety of positions on the Nucleic Acid Ligand. In embodiments where PEG or diacyl glycerol are used, it is preferred that the Nucleic Acid Ligand is bonded to the 5' thiol through a maleimide or vinyl sulfone functionality or via a phosphodiester linkage. In embodiments where dialkyl glycerol and cholesterol are used, it is preferred that the Nucleic Acid Ligand is bonded via a phosphodiester linkage. In certain embodiments, a plurality of Nucleic Acid Ligands can be associated with a single PEG, dialkyl glycerol, diacyl glycerol, or cholesterol molecule. The Nucleic Acid Ligands can be to the same or different Target. In embodiments where there are multiple Nucleic Acid Ligands to the same Target, there is an increase in avidity due to multiple binding interactions with the Target. In yet further embodiments, a plurality of PEG, dialkyl glycerol, diacyl glycerol, or cholesterol molecules can be attached to each other. In these embodiments, one or more Nucleic Acid Ligands to the same Target or different Targets can be associated with each PEG, dialkyl glycerol, diacyl glycerol, or cholesterol molecule. This also results in an increase in avidity of each Nucleic Acid Ligand to its SELEX Target. In embodiments where multiple Nucleic Acids specific for the same SELEX Target are attached to PEG, dialkyl glycerol, diacyl glycerol, or cholesterol, there is the possibility of bringing the same Targets in close proximity to each other in order to generate specific interactions between the same Targets. Where multiple Nucleic Acid Ligands specific for different Targets are attached to PEG, dialkyl glycerol, diacyl glycerol, or cholesterol, there is the possibility of bringing the distinct Targets in close proximity to each other in order to generate specific interactions between the Targets. In addition, in embodiments where there are Nucleic Acid Ligands to the same Target or different Targets associated with PEG, dialkyl glycerol, diacyl glycerol, or cholesterol, a drug can also be associated with PEG, dialkyl glycerol, diacyl glycerol, or cholesterol. Thus the Complex would provide targeted delivery of the drug, with PEG, dialkyl glycerol, diacyl glycerol, or cholesterol serving as a Linker.

In another embodiment of the invention, the Complex is comprised of a Nucleic Acid Ligand attached to a Non-Immunogenic, High Molecular Weight Compound such as magnetite. As discussed supra, the association could be through Covalent Bonds or Non-Covalent Interactions. In the preferred embodiment, the Nucleic Acid Ligand is associated with magnetite through Covalent Bonds. The magnetite can be coated with a variety of compounds that display different functional chemistries for attachment (e.g., dextran, Lipophilic Compounds). The Nucleic Acid Ligand in association with the magnetite provides targeted delivery of the magnetite for use in nuclear magnetic resonance imaging.

The following examples are provided to explain and illustrate the present invention and are not to be taken as limiting of the invention. The structures of the Nucleic Acid Ligands described in the examples below are shown in FIG. 1. Example 1 describes the conjugation of Nucleic Acid Ligands with lipid, dialkyl glycerol or diacyl glycerol, as well as incorporation of pharmacokinetic modifiers via automated synthesis. Example 2 describes the conjugation of PEG and cholesterol with a Nucleic Acid Ligand. The modifications to the Nucleic Acid Ligand do not interfere with its ability to bind to its SELEX Target, as the binding affinities of the PEG-conjugated and cholesterylated Nucleic Acid Ligands were identical to the non-conjugated and non-cholesterylated molecules. Example 3 describes the incorporation of a cholesterol-derivatized Nucleic Acid Ligand into a lipid formulation. The activity of the Nucleic Acid Ligand/Liposome formulations containing thrombin Nucleic Acid Ligands was tested in an in vitro clotting inhibition assay. Liposome processing conditions do not affect the anticoagulation activity of the Nucleic Acid Ligand. In addition, the liposomal association does not affect the ability of the Nucleic Acid Ligand to bind and inhibit its Target. Example 4 describes the pharmacokinetic properties of Nucleic Acid Ligands in association with cholesterol alone, dialkyl glycerol alone, with PEG alone, with cholesterol and Liposome, with dialkyl glycerol and Liposomes, and with PEG and Liposome. Nucleic Acid Ligands that have been modified at the 2' sugar position of purines and pyrimidines are also included. Example 5 reports on the toxicity and intracellular uptake by human lymphocytes of Cationic Liposome-Nucleic Acid Ligand Complexes. Examples 6-10 describe the following effects on the incorporation of Nucleic Acid Ligands into preformed Liposomes: varying the negative charge of the lipids, varying the cholesterol content, varying the lipid/Nucleic Acid Ligand ratio with a fixed amount of Nucleic Acid Ligand, varying the lipid/Nucleic Acid Ligand ratio with a fixed amount of SUV, and varying the phospholipid chain length. Example 11 demonstrates that incorporation of a Nucleic Acid Ligand/cholesterol conjugate into a liposomal formulation has occurred via non-denaturing gel electrophoresis. Example 12 describes the way in which Nucleic Acid Ligands can be passively encapsulated into Liposomes. Example 13 describes the way in which Nucleic Acid Ligands can be remotely loaded into Liposomes. Example 14 describes the covalent conjugation of Nucleic Acid Ligands to Liposomes. Example 15 describes the in vitro and in vivo efficacy of a Nucleic Acid Ligand-Liposome Complex.

Example 1

Lipid, PEG, Dialkyl Glycerol and Diacyl Glycerol Reagents For Oligonucleotide Modification In this example, conjugation of Nucleic Acid Ligands with lipid and/or PEG or diacyl glycerol or diakyl glycerol reagents is described, as well as incorporation of the pharmacokinetic modifiers via automated synthesis using either phosphoramidite or H-phosphonate coupling chemistry. In the schemes depicted below, a solid arrow represents steps that have been completed, whereas a dashed arrow represents steps that have not yet been completed. Scheme 1 depicts the preparation of a dipalmitoyl phosphatidyl ethanolamine maleimide reagent for coupling to sulfhydryl-modified oligonucleotide substrates. This procedure is analogous to that reported by Cheronis et al (Cheronis, J. C. et al., *J. Med. Chem.* (1992) 35:1563-1572) for the preparation of bis- and tris-maleimide reagents from simple, aliphatic di- and triamine substrates. Treatment of the phospholipid with methoxycarbonyl maleimide resulted in formation of an uncharacterized intermediate which, upon incubation with sulfhydryl-modified oligonucleotide, resulted in complete conversion of the oligonucleotide to the dipalmitoyl phosphatidyl ethanolamine conjugate (vida infra). Similar reagents are also available commercially from Avanti Polar Lipids.

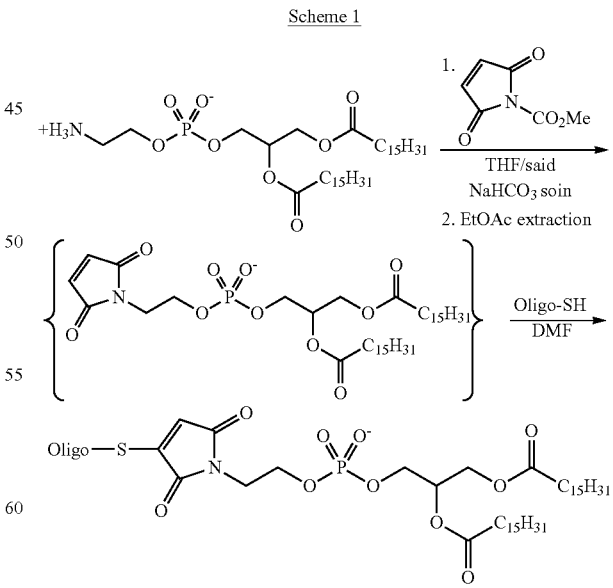

The ability to modify oligonucleotides under automated synthesis conditions has many obvious advantages. Reagents were prepared which allowed facile incorporation of lipid and/or PEG moieties under standard automated synthesis conditions. Initially, the versatile module 10 was designed and synthesized (Scheme 2) which could be divergently converted to any number of oligo modification reagents of interest by simply chemoselectively functionalizing the amine group then phosphitylation of the hydroxyl group. Noteworthy is the flexibility this strategy offers with respect to the modification group (the amine ligand) and the activated phosphate precursor (phosphoramidite, H-phosphonate, or phosphate triester) introduced via derivatization of the 2'-hydroxyl group. Additionally, the glycerol nucleus of automated synthesis reagents prepared in this way renders the products suitable for oligo modification at internal chain positions, or at the 5' end. An alternative synthesis of module 10 is shown in Scheme 3. Tetraethylene glycol (1; TEG) is derivatized as the monotosylate 2a upon treatment with a limiting amount of p-toluenesulfonyl chloride, preferably 10 mole percent, in a basic medium, preferably pyridine. In this manner, 2a was obtained in 75% yield after silica gel filtration. Conversion of 2a to the TEG phthalimide 3a was accomplished in 80% yield upon treatment with phthalimide in the presence of diazabicycloundecane (DBU) as a base at elevated temperature in DMF solution. Allylation of phthalimide 3a (allyl bromide, NaH, THF/DMF) afforded 65% yield of allyl TEG 4a. Treatment of 4a with 0.5% $OsO_4$ and 1.1 equivalents of N-methylmorpholine N-oxide (NMO) afforded a diol intermediate that was, without further purification, converted to the dimethoxytrityl (DMT) ether derivative 9 in 89% overall yield for the two steps. Finally, amine deprotection using 40% $MeNH_2$ was carried out to afford 10 in 95% purified yield. Module 10 has been further elaborated by treatment with PEG-nitrophenylcarbonate (PEG-NPC; Shearwater Polymers). In this way, the phosphitylation precursor 12 (Scheme 4) was prepared in excellent yield. Further conversions of 12 to both phosphoramidite 13 and H-phosphonate 14 have been carried out.

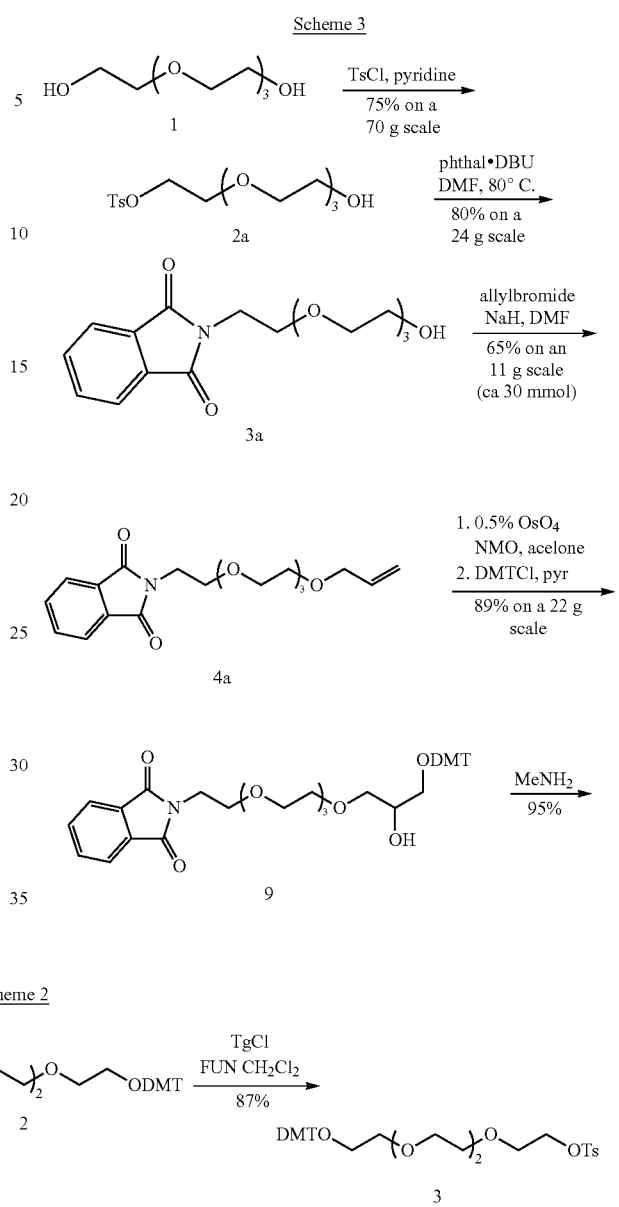

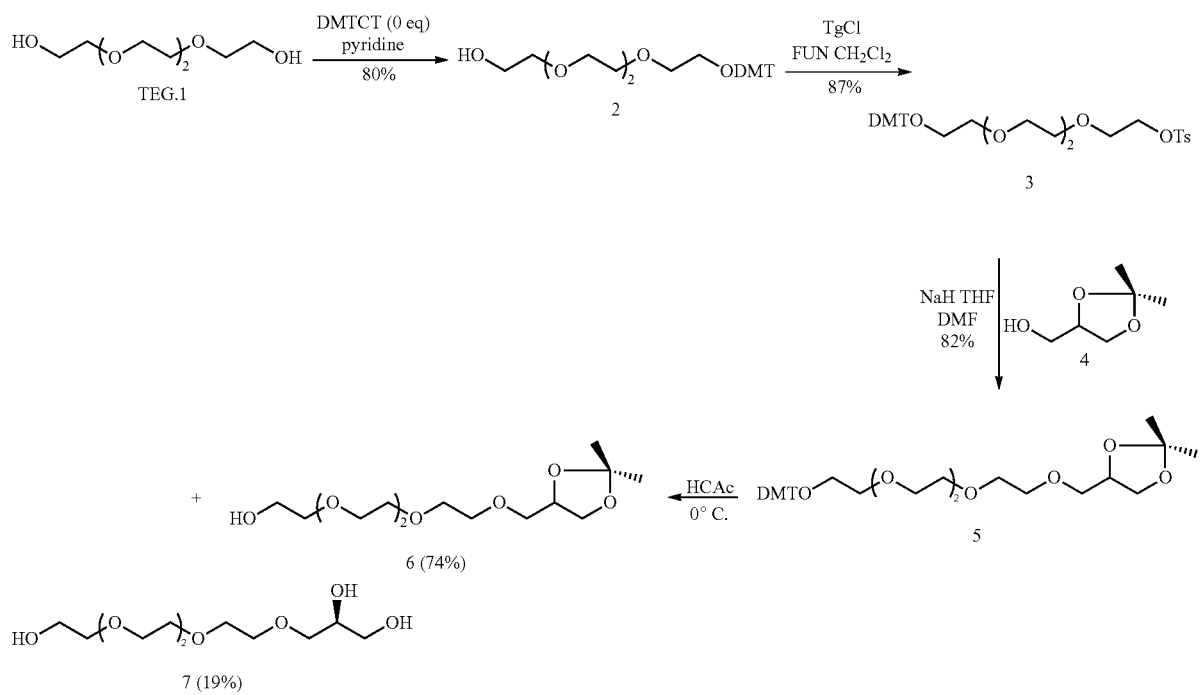

-continued

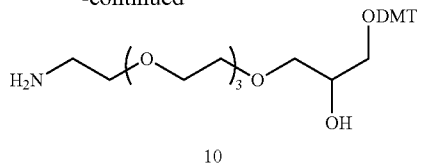

10 pyridine) and this activated intermediate was coupled with the module 10 (pyridine. 80° C.; 44%). Phosphitylation (CIP (iPr$_2$N)OCH$_2$CH$_2$CN; diisopropylethylamine (DIPEA), CH$_2$Cl$_2$; 59%) of 16 afforded the phosphoramidite 17 (Scheme 5). Synthesis of a C$_{18}$ analog of amidite 17 via a chloroformate intermediate is shown in Scheme 6. The dialkyl glycerol (18; DAG) was converted to the corresponding chloroformate 19 upon treatment with excess phosgene in Scheme 4

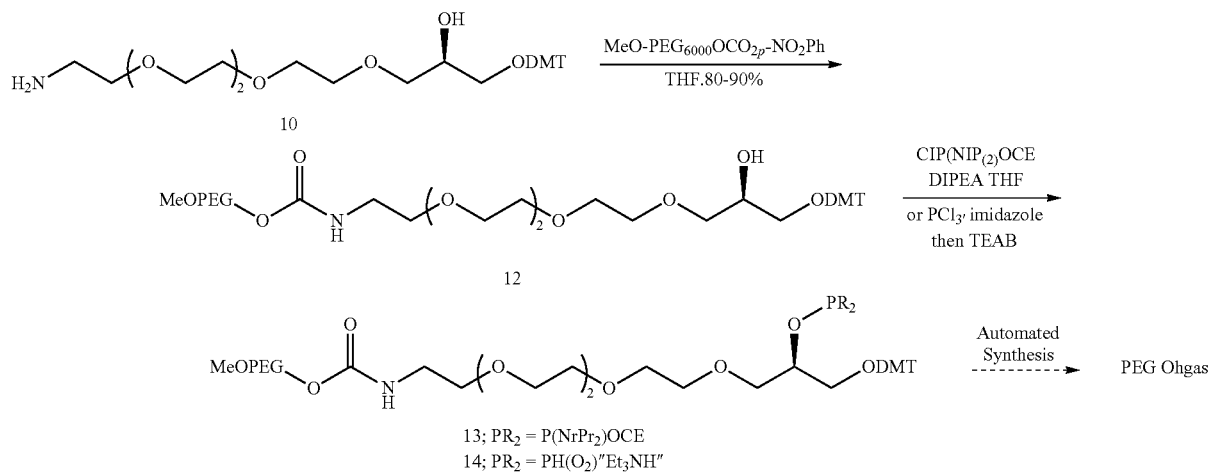

13; PR$_2$ = P(NrPr$_2$)OCE
14; PR$_2$ = PH(O$_2$)"Et$_3$NH"

The design of a lipid reagent for oligonucleotide modification by automated synthesis necessitates replacement of the ester linkages of native diacyl glycerols, as in the dipalmitoyl phosphatidyl derivative described above, by glycerol-alkyl linkages stable to the basic deprotection protocol required for synthetic oligo recovery. The linkage that was chosen to explore initially was the ether linkage, as in the known dipalmityl glycerol derivative 15 (available from Sigma), although long-chain alkyl carbamates (or a combination of ethers and carbamates) would also be suitable. Dipalmityl glycerol was activated as the acyl carbonyl imidazole (CDI, toluene. Conjugation of 19 and amino alcohol 10 was carried out in pyridine to afford adduct 20 in 57% purified yield. Phosphitylation of the secondary hydroxyl of 20 under standard condition afforded phosphoramidite 21 in 95% yield. Coupling of amidite 17 to the 5'-end of a trinucleotide (TTT) on an ABI 394 automated oligonucleotide synthesizer using a slightly modified synthesis cycle with extended coupling times (2×30 min couplings) for the lipid amidite resulted in 94+% coupling efficiency, as determined by in-line trityl cation analysis.

Scheme 5

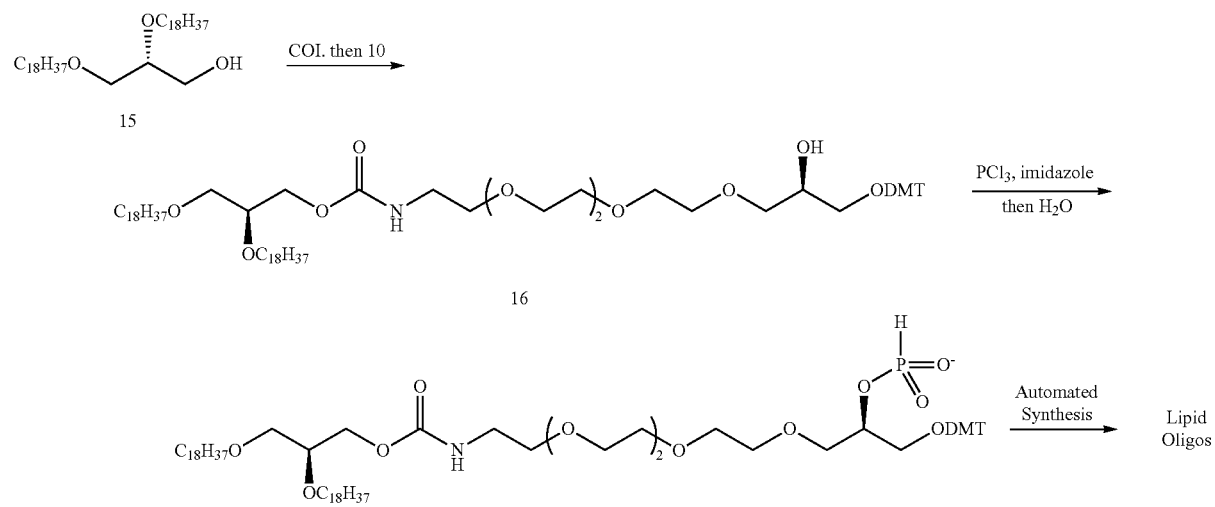

Scheme 6

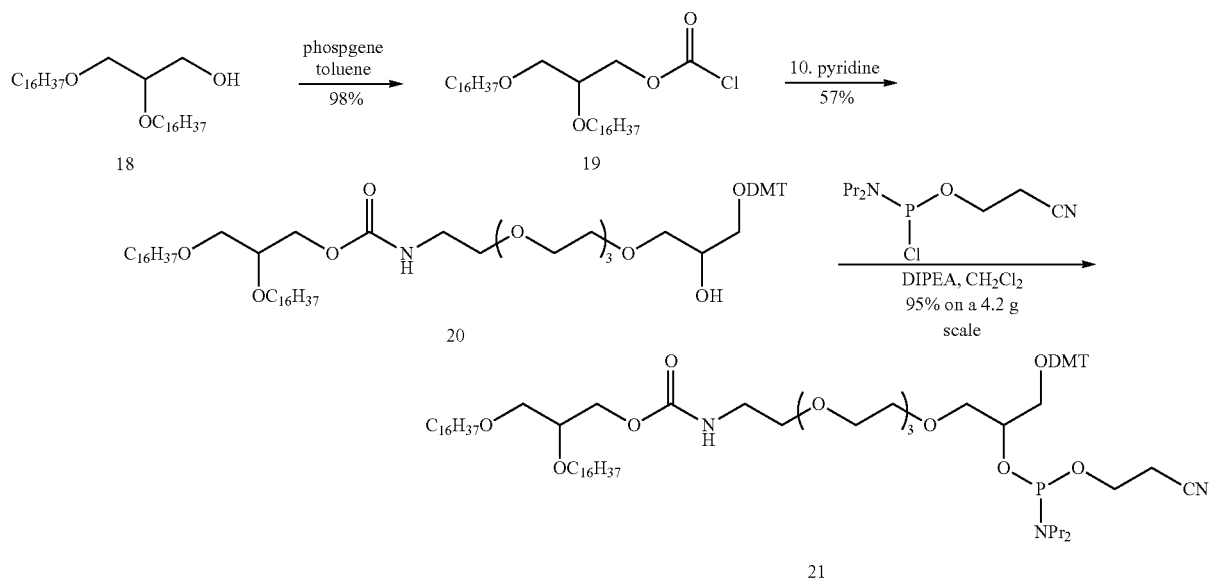

Example A

Synthesis of Dipalmitoyl Phosphatidylethanolamine (DPPE)

Maleimide Reagent: A suspension of 200 mg (0.289 mmol) of DPPE and 54 mg (0.347 mmol) of methoxycarbonyl maleimide in 10 mL of THF/saturated NaHCO$_3$ solution (1:1) was stirred at ambient temperature. After 12 h, the mixture was treated with 100 mL of EtOAc and the organic phase (which contained a gelatinous suspension of the product) separated from the aqueous phase. The organic phase was concentrated in vacuo, coevaporated twice with MeOH, and the resultant white solid triturated three times with EtOAc. This material was used without further characterization or purification in oligonucleotide conjugation experiments (viola infra).

Example B

Synthesis and Elaborations of Automated Synthesis Module 10

Tetraethylene glycol dimethoxytrityl ether (2): Tetraethylene glycol (76.4 mL, 0.44 mol) was dissolved in 300 mL of anhydrous pyridine and cooled to 0° C. 4,4'-dimethoxytrityl chloride (15 g, 0.044 mol) was added as a solid with stirring. The reaction flask was covered with a drying tube and the reaction was allowed to warm to ambient temperature overnight. The reaction was concentrated in vacuo at low temperature (<30° C.). The residue was diluted with 300 mL of ethyl acetate and extracted with 3×300 mL of water. The combined aqueous layers were extracted with ethyl acetate, and the combined organic layers were dried over sodium sulfate and concentrated. The crude residue was purified by flash chromatography using 1000 mL of silica gel (wet-packed onto column with hexane containing 5% triethylamine), eluting with 10-20-40-60-80% ethyl acetate in hexane containing 5% triethylamine, and then ethyl acetate containing 5% triethylamine. 19.51 g (89%) of 2 was collected as a gold oil. $^1$H NMR (300 MHz, CDCl$_3$) d 7.47-7.16 (overlapping signals, 9H), 6.79 (d, 4H), 3.72 (s, 6H), 3.66-3.62 (m, 2H), 3.22 (t, J=5.22 Hz, 1H), 2.96 (br t, 1H); $^{13}$C NMR (75 MHz, CDCl$_3$) d 158.12, 144.86, 136.04, 129.81, 127.93, 127.49, 126.40, 112.78, 85.67, 72.31, 70.48, 70.44, 70.12, 62.89, 61.39, 54.89; Low resolution MS m/e calculated for C$_{15}$H$_{25}$O$_7$S (M-DMT+1$^+$): 349.167, found 349.1.

Tetraethylene glycol dimethoxytrityl ether p-toluenesulfonate (3): Compound 2 (5.0 g, 10.06 mmol) was dissolved in 50 mL of anhydrous dichloromethane and cooled to 0° C. Triethylamine (1.82 mL, 13.1 mmol) was added, followed by p-toluenesulfonyl chloride (1.92 g, 10.06 mmol) as a solid, with stirring. The reaction was stored in the refrigerator overnight. TLC Analysis indicated the reaction was approximately 80% complete. An additional 0.5 equivalents of triethylamine and 0.5 equivalents of p-toluenesulfonyl chloride were added, and the reaction was stirred at room temperature overnight. The reaction was filtered through Celite and concentrated. The residue was purified by flash chromatography using 300 mL of silica gel (wet-packed onto column using 5% triethylamine in hexane) eluting with 25-50-75% ethyl acetate in hexane containing 5% triethylamine, and then ethyl acetate containing 5% triethylamine. 5.7 g (87%) of 3 was collected as an orange oil. $^1$H NMR (300 MHz, CDCl$_3$) d 7.75 (d, 2H), 7.44-7.12 (m, 11H), 6.78 (d, 4H), 4.12-4.09 (m, 2H), 3.73 (s, 6H), 3.66-3.54 (m, 13H), 3.22 (t, J=3.87 Hz, 2H), 2.41 (s, 3H).

Tetraethylene glycol monotosylate (2a): Tetraethylene glycol (200 mL, 1.15 mol) was dissolved in 500 mL of pyridine and cooled to 0° C. and treated with 22.0 g (0.115 mol) of p-toluenesulfonyl chloride. When solution was complete, the reaction mixture was stored in the refrigerator overnight, and then concentrated in vacuo. The residue was dissolved in 800 mL of EtOAc and extracted with 3×600 mL of H$_2$O. The H$_2$O fractions were back-extracted with EtOAc, and the combined EtOAc fractions were extracted with saturated aqueous Na$_2$HPO$_4$. The organic phase was dried over MgSO$_4$ and concentrated to a colorless oil The oil was purified by flash chromatography using 800 mL of silica gel and eluting with hexane, 25% EtOAc-50% EtOAc in hexane, then EtOAc, then 10% MeOH-20% MeOH in EtOAc to afford 23.7 g (60%) of pure product and 11% of product containing a minor impurity. 2a: $^1$H NMR (300 MHz, CDCl$_3$) d 7.77 (d, J=8.1 Hz, 2H), 7.32 (d, J=8.1 Hz, 2H), 4.13 (t, J=4.8 Hz, 2H), 3.68-3.53 (m, 14H), 2.58 (t, J=5.6 Hz, 1H), 2.42 (s, 3H); $^{13}$C NMR (75 MHz, CDCl$_3$) d 168.2, 158.3, 144.8, 135.9, 133.8, 132.0, 129.9, 128.0, 127.7, 126.6, 123.1, 113.0, 85.9, 73.0, 70.6, 70.4, 70.0, 69.7, 67.8, 64.4, 55.1, 37.1; Low resolution MS m/e calculated for C$_{15}$H$_{24}$O$_8$S (M+1): 349.1.

Tetraethylene glycol monophthalimide (3a): To a stirred solution of 31.96 g (0.092 mol) of 2a in 400 mL of anhydrous DMF was added 14.2 g (1.05 equiv.) of phthalimide and 14.4 mL (1.05 equiv.) of 1,8-diazabicyclo[5.4.0]undec-7-ene. The solution was heated at 70° C. for 18 h then concentrated in vacuo. The crude yellow oil was purified by flash chromatography using 1600 mL of silica gel and eluting with 25% EtOAc-50% EtOAc-75% EtOAc in hexane, then EtOAc, then 10% MeOH-20% MeOH in EtOAc to afford 23.8 g (80%) of 3a as an oil. Upon standing, 3a became a waxy white solid. $^1$H NMR (300 MHz, CDCl$_3$) d 7.84-7.78 (m, 2H), 7.70-7.66 (m, 2H), 3.86 (t, J=5.6 Hz, 2H), 3.70 (t, J=5.6 Hz, 2H), 3.64-3.51 (m, 12H), 2.67 (bs, 1H); $^{13}$C NMR (75 MHz, CDCl$_3$) d 168.2, 133.8, 132.0, 123.1, 72.4, 70.5, 70.4, 70.2, 70.0, 67.8, 61.6, 37.2.

Synthesis of compound 4a: A solution of 15 g (0.0464 mol) of 3a in 150 mL of THF and 15 mL of DMF was cooled to 0° C. under Ar. Allyl bromide (6.0 mL, 1.5 equiv.) was added to the solution, followed by addition of 1.76 g (1.5 equiv.) of NaH as a solid. The opaque yellow suspension was stirred at 0° C. for 30 minutes and then at room temperature for 18 hr. MeOH (50-100 mL) was added and concentrated then mixture was concentrated in vacuo. The crude material was purified by flash chromatography using 1500 mL of silica gel and eluting with 25% EtOAc-50% EtOAc-75% EtOAc in hexane, then EtOAc, then 10% MeOH in EtOAc to afford 11.05 g (65%) of 4a as a yellow oil. $^1$H NMR (300 MHz, CDCl$_3$) d 7.84-7.80 (m, 2H), 7.72-7.67 (m, 2H), 5.94-5.84 (m, 1H), 5.28-5.14 (m, 2H), 3.99 (d, J=5.61 Hz, 2H), 3.88 (t, J=5.85 Hz, 2H), 3.72 (t, J=5.76 Hz, 2H), 3.64-3.54 (m, 13H); $^{13}$C NMR (75 MHz, CDCl$_3$) d 168.0, 134.6, 133.7, 131.9, 123.0, 116.9, 72.0, 70.4, 69.9, 69.2, 67.7, 37.0.

(S)-(+)-2,2-Dimethyl-1,3-dioxolanyl-4-ylmethyl (dimethoxytrityl)tetra-ethylene glycol (5): Sodium hydride (0.56 g, 23.5 mmol) is weighed into a flame-dried flask, and 70 mL of anhydrous tetrahydrofuran and 15 mL of anhydrous N,N-dimethylformamide were added. The suspension was cooled to 0° C. under argon, and (S)-(+)-2,2-dimethyl-1,3-dioxolane-4-methanol (2.7 mL, 21.7 mmol) was added dropwise via syringe. After stirring for 30 min at 0° C., compound 3 (11.77 g, 18.1 mmol) in 15 mL of tetrahydrofuran was added dropwise via addition funnel. The reaction mixture was stirred at ambient temperature overnight, then quenched with 100 mL of saturated aqueous sodium bicarbonate and diluted with 300 mL of diethyl ether. The layers were separated, and the ether layer was extracted 3 times with 300 mL of water. The ether layer was dried over sodium sulfate and concentrated. The residue was purified by flash chromatography using 500 mL of silica gel and eluting first with hexane and then 10-20-30-40-50-75% ethyl acetate in hexane and then with ethyl acetate. 8.93 g (82%) of 5 was collected as a colorless oil. $^1$H NMR (CDCl$_3$) d 7.46-7.43 (m, 2H), 7.34-7.17 (m, 7H), 6.78 (d, 4H), 4.23 (pentet. J=6.1 Hz, 1H), 4.00 (t, 8.2H), 3.75 (s, 6H), 3.71-3.60 (m, 15H), 3.53 (dd, J=10.0, 5.7 Hz, 1H), 3.52 (10.4, J=5.2 Hz, 1H), 1.39 (s, 3H), 1.33 (s, 3H); $^{13}$C NMR (75 MHz, CDCl$_3$) d 158.24, 144.97, 136.20, 129.93, 128.07, 127.61, 126.51, 112.89, 109.21, 85.77, 74.57, 72.20, 70.82, 70.59, 70.40, 69.68, 66.67, 63.01, 55.04, 26.67, 25.29; Low resolution MS m/e calculated for C$_{35}$H$_{50}$O$_9$N (M+NH$_4^+$): 628.399, found 628.5.

(S)-(+)-2,2-Dimethyl-1,3-dioxolanyl-4-ylmethyl tetraethylene glycol (6): 100 mL of 80% acetic acid was cooled to 0° C. and then added to compound 5 (6.6 g, 10.8 mmol) The clear orange solution was stirred at 0° C. for 1 hr. Methanol (100 mL) was added, and the reaction mixture was concentrated in vacuo at low temperature (<30° C.). The residue was purified by flash chromatography using 200 mL of silica gel, eluting first with ethyl acetate, and then 5-10-15-20% methanol in ethyl acetate. 2.5 g (74%) of 6 was collected as a colorless oil. $^1$H NMR (CDCl$_3$) d 4.21 (pentet, J=6.2 Hz, 1H), 4.08 (dd, J=5.9, 4.8 Hz, 1H), 3.82-3.35 (m, 19H), 2.93 (br s, 1H), 1.34 (s, 3H), 1.28 (s, 3H); $^{13}$C NMR (75 MHz. CDCl$_3$) d 109.20, 74.50, 72.42, 72.14, 70.76, 70.39, 70.32, 70.14, 66.63, 61.48, 26.61, 25.23; Low resolution MS m/e calculated for C$_{35}$H$_{50}$O$_9$N (M+NH$_4$+): 628.399, found 628.5.

(S)-(+)-2,2-Dimethyl-1,3-dioxolanyl-4-ylmethyl (phthalimido)tetraethylene glycol (8): Alcohol 6 (4.06 g, 13.2 mmol) was dissolved in 50 mL of anhydrous dichloromethane and cooled to 0° C. Triethylamine (3.7 mL, 26.3 mmol) was added, followed by addition of p-toluenesulfonyl chloride (3.26 g, 17.1 mmol). The reaction flask was covered by a drying tube and allowed to warm to room temperature overnight. The reaction mixture was filtered through Celite, and the filtrate was concentrated in vacuo. The crude material was purified by flash chromatography on 400 mL of silica gel, eluting first with 10% ethyl acetate in hexane, and then 20-40-60-80-100% ethyl acetate, and then 10% methanol in ethyl acetate. Collected 5.21 g (85%) of the intermediate tosylate as a gold oil. ($^1$H NMR (400 MHz, CDCl$_3$) d 7.79 (d, J=8.1 Hz, 2H, tosyl aromatics), 7.32 (d, J=8.1 Hz, 2H, tosyl aromatics), 4.25 (pentet, J=6.0 Hz, 1H), 4.13 (t, 4.7H), 4.02 (dd, J=8.12, 6.4 Hz, 1H), 3.71-3.40 (m, 18H), 2.42 (s, 3H), 1.46 (s, 3H), 1.34 (s, 3H); $^{13}$C NMR (75 MHz, CDCl$_3$) d 144.74, 133.1, 129.76, 127.91, 109.8, 74.63, 72.27, 70.89, 70.68, 70.52, 70.44, 69.19, 68.60, 66.74, 64.1, 26.73, 25.34, 21.59; Low resolution MS m/e calculated for C$_{21}$H$_{38}$O$_9$NS (M+NH$_4^+$): 480.364, found 480.2.) The tosylate (5.2 g, 11.24 mmol) was dissolved in 60 mL of anhydrous dimethylformamide. 1,8-Diazabicyclo-[5.4.0]undec-7-ene (1.7 mL, 11.24 mmol) was added, followed by phthalimide (1.65 g, 11.24 mol). The reaction mixture was heated to 70° C. overnight. The reaction was concentrated in vacuo, and purified by flash chromatography on 400 mL of silica gel, eluting with 50% ethyl acetate in hexane. Collected 3.96 g (81%) of 8 as a colorless oil. $^1$H NMR (300 MHz, CDCl$_3$) d 7.83-7.79 (m, 2H), 7.72-7.68 (m, 2H), 4.26 (pentet, J=6.0 Hz, 1H), 4.03 (dd, J=8.2, 6.5 Hz, 1H), 3.88 (t, J=5.8 Hz, 1H), 3.74-3.44 (m, 18H), 1.39 (s, 3H), 1.33 (s, 3H); $^{13}$C NMR (75 MHz, CDCl$_3$) d 168.21, 133.88, 132.10, 123.19, 109.33, 74.66, 72.30, 70.90, 70.52, 70.04, 67.87, 66.79, 37.19, 26.75, 25.37; MS m/e calculated for C$_{22}$H$_{35}$O$_8$N$_2$ (M+NH$_4^+$): 455.288, found 455.2.

1-Dimethoxytrityl-3-(phthalimidotetraethylene glycolyl)-sn-glycerol (9): According to Scheme 2, compound 9 is synthesized as follows: the acetyl 8 (5.16 g, 11.8 mmol) was dissolved in 100 mL of anhydrous methanol, and anhydrous p-toluenesulfonic acid (100 mg) was added. The reaction flask was covered with a drying tube and the reaction was stirred at ambient temperature for 2.5 h, then neutralized by the addition of 10 mL of anhydrous pyridine, concentrated in vacuo, and coevaporated with anhydrous pyridine. The resulting diol was then dissolved in 150 mL of anhydrous pyridine and cooled to 0° C. 4,4'-Dimethoxytrityl chloride (4.39 g, 13 mmol) was added as a solid. The reaction flask was covered with a drying tube, and the reaction was allowed to warm to ambient temperature overnight. Methanol (50 mL) was added, and the reaction was concentrated in vacuo. The crude material was purified by flash chromatography on 700 mL of silica gel (wet-packed onto column with 5% triethylamine in hexane), eluting first with 10% ethylacetate in hexane (containing 5% triethylamine) and then 20-40-60-80-100% ethyl acetate (containing 5% triethylamine). Collected 6.98 g (82%) of 9 as a pale yellow oil. $^1$H NMR (300 MHz, CDCl$_3$) d 7.80 (dd, J=5.4, 3.1 Hz, 2H), 7.68 (dd, J=5.4, 3.1 Hz, 2H), 7.42-7.14 (m, 9H, DMT), 6.79 (d, 4H, DMT), 3.95 (br m, 1H), 3.86 (t, J=5.9 Hz, 1H), 3.75 (s, 6H), 3.70 (t, J=5.6 Hz, 1H), 3.63-3.37 (m, 18H), 3.16 (m, 2H), 2.84 (br d, 1H); $^{13}$C NMR (75 MHz, CDCl$_3$) d 168.15, 158.32, 144.79, 135.95, 133.82, 132.02, 129.95, 128.04, 127.69, 126.64, 123.12, 112.97, 85.89, 72.97, 70.64, 70.43, 69.97, 69.74, 67.80, 64.34, 55.10, 37.14; Low resolution MS m/e calculated for $C_{40}H_{49}O_{10}N_2$ (M+NH$_4^+$): 717.398, found 717.5. According to Scheme 3, compound 9 was synthesized as follows: To a stirred solution of 4a (10.13 g, 0.0279 mol) in 100 mL of acetone and 1 mL of H$_2$O was added 3.98 g (1.22 equiv.) of N-methylmorpholine N-oxide. To this suspension was added 1.75 mL (0.005 equiv.) of Osmium tetroxide as a 2.5% solution in iPrOH. After addition of the OsO$_4$ solution, the reaction mixture became clear yellow. After TLC analysis indicated complete conversion of 4a (ca 16 h), the reaction mixture was treated with 1.5 g of sodium hydrosulfite and 5.0 g of florisil and stirred 30 minutes. The suspension was filtered through florisil, the filtrate was concentrated to an oil. This crude product was combined with another batch prepared in the same manner from 1.0 g of 4a. Two 100 mL portions of pyridine were co-evaporated from the combined lots and the residue was dissolved in 300 mL pyridine. The solution was cooled to 0° C. and 10.89 g (1.05 equiv.) of 4,4'-dimethoxytrityl chloride was added. A drying tube was inserted in the flask and the reaction mixture was stirred at room temperature 16 h. The solution was treated with 20 mL of MeOH and concentrated in vacuo, keeping the temperature of the water bath below 40° C. The crude oil was purified by flash chromatography using 1100 mL of silica gel (wet-packed onto column using 3% triethylamine in hexane) and eluting with 10-100% EtOAc in hexane (all containing 3% triethylamine) to give 21.3 g (89% after two steps) of 9 as a yellow oil. $^1$H NMR (300 MHz, CDCl$_3$) d 7.80-7.77 (m, 2H), 7.66-7.64 (m, 2H), 7.39-7.22 (m, 9H), 7.20-6.76 (m, 4H), 3.97 (bs, 1H), 3.84 (t, J=5.97 Hz, 2H), 3.74 (s, 6H), 3.68 (t, J=5.7 Hz, 2H), 3.60-3.49 (m, 14H), 3.13-2.76 (m, 2H), 2.00 (bs, 1H); $^{13}$C NMR (75 MHz, CDCl3) d 168.2, 158.3, 144.8, 135.9, 133.8, 132.0, 129.9, 128.0, 127.7, 126.6, 123.1, 113.0, 85.9, 73.0, 70.6, 70.4, 70.0, 69.7, 67.8, 64.4, 55.1, 37.1; Low resolution MS ink calculated for $C_{40}H_{45}O_{10}N$ (M+NH$_4$+): 717.5.

1-Dimethoxytrityl-3-(aminotetraethylene glycolyl)-sn-glycerol (10): According to Scheme 2, compound 10 was synthesized as follows: Compound 9 (5.2 g, 7.2 mmol) was taken up in 50 mL of 40% methylamine in H$_2$O and 10 mL of methanol was added to solublize the starting material. The reaction mixture was heated at 50° C. for 5 hr, and than was concentrated in vacuo and coevaporated with toluene. The crude material was purified by flash chromatography on 200 mL of silica gel, eluting with 15% methanolic ammonia in dichloromethane. Collected 3.94 g (96%) of 10 as a pale yellow oil. $^1$H NMR (300 MHz, CDCl$_3$) d 7.46-7.21 (m, 9H, DMT), 6.81 (d, 4H, DMT), 4.00 (m, 1H), 3.80 (s, 6H), 3.70-3.49 (overlapping m, 18H), 3.20 (dd, J=9.24, 5.49 Hz, 1H), 3.12 (dd, J=9.21, 6.0 Hz, 1H), 2.84-2.80 (m, 3H); $^{13}$C NMR (75 MHz, CDCl$_3$) d 158.30, 144.82, 136.01, 129.95, 128.04, 127.66, 126.61, 112.95, 85.85, 73.46, 72.85, 70.55, 70.45, 69.99, 69.51, 64.43, 55.10, 41.40; Low resolution MS ink calculated for $C_{32}H_{44}O_8N$ (M+1$^+$): 570.353, found 570.4.

According to Scheme 3, compound 10 was synthesized as follows: Compound 9 (5.2 g, 7.2 mmol) was taken up in 50 mL of 40% methylamine in H$_2$O and 10 mL of methanol was added to solublize the starting material. The reaction mixture was heated at 50° C. for 5 hr, and than was concentrated in vacuo and coevaporated with toluene. The crude material was purified by flash chromatography on 200 mL of silica gel, eluting with 15% methanolic ammonia in dichloromethane. Collected 3.94 g (96%) of 10 as a pale yellow oil. $^1$H NMR (300 MHz, CDCl$_3$) d 7.46-7.21 (m, 9H, DMT), 6.81 (d, 4H, DMT), 4.00 (m, 1H), 3.80 (s, 6H), 3.70-3.49 (overlapping m, 18H), 3.20 (dd, J=9.24, 5.49 Hz, 1H), 3.12 (dd, J=9.21, 6.0 Hz, 1H), 2.84-2.80 (m, 3H); $^{13}$C NMR (75 MHz, CDCl$_3$) d 158.30, 144.82, 136.01, 129.95, 128.04, 127.66, 126.61, 112.95, 85.85, 73.46, 72.85, 70.55, 70.45, 69.99, 69.51, 64.43, 55.10, 41.40; Low resolution MS m/e calculated for $C_{32}H_{44}O_8N$ (M+1$^+$): 570.353, found 570.4.

PEG Reagent 12: To a stirred solution of 0.24 g (0.41 mmol) of 10 in 10 mL DMF was added 2.08 g (0.4 mmol) of methoxy-PEG$_{5000}$-nitrophenyl carbonate (Shearwater Polymers, Inc.). The mixture was stirred 70 h then concentrated in vacuo. The residue was dissolved in EtOAc and the organic phase washed with three 30 mL portions of 10% NaOH solution. Purification by flash chromatography using 100 mL of silica gel (wet packed with dichloromethane containing 5% Et$_3$N) eluting with 5-10-15-20% methanolic ammonia in dichloromethane afforded 1.97 g (85%) of 12 as a white solid. $^1$H NMR (300 MHz, CDCl$_3$) d 7.42-7.39 (d, 2H, DMT), 7.39-7.18 (m, 7H, DMT), 6.79 (d, 4H, DMT), 5.70 (br m, 1H), 4.21 (m, 1H), 3.97 (m, 1H), 3.88 (t, J=4.4 Hz, 1H), 3.81 (s, 6H, DMT), 3.78-3.50 (br m, ~500, PEG Hs), 3.42-3.31 (overlapping ms), 3.35 (s, PEG Me), 3.16 (m, 2H), 2.84 (br d, 4.2H); $^{13}$C NMR (75 MHz, CDCl$_3$) d 159.36, 157.19, 146.15, 136.95, 130.83, 128.86, 128.65, 127.61, 113.86, 86.48, 73.58, 72.88, 72.5-70.0 (PEG carbons), 68.31, 65.77, 64.45, 41.36, 30.75 (unassigned impurity).

PEG Phosphoramidite Reagent 13: To a stirred solution of 2.22 g (0.4 mmol) of 12 in 60 mL of THF over 3 Å molecular sieves was added 0.24 mL (1.39 mmol) of diisopropylethylamine and 0.1 mL (0.44 mmol) of 2-cyanoethyl N,N-diisopropylchlorophosphoramidite. After 5 h, 31P NMR indicated formation of desired product, as well as hydrolyzed phosphitylating agent and an additional 0.05 mL (0.22 mmol) of 2-cyanoethyl N,N-diisopropylchlorophosphoramidite was added. After 12 h, 0.07 mL (0.4 mmol) of DIPEA and 0.1 mL of the chlorophosphoramidite were added. The mixture was stirred 2 days, filtered through Celite and concentrated in vacuo. The residue was triturated with several portions of ether. $^{31}$P NMR d 156.4, 155.8. Also observed were signals at d 20.6, 19.8 presumed to correspond to hydrolyzed phosphitylation reagent.

PEG H-Phosphonate Reagent 14: To a stirred, 0° C. solution of anhydrous imidazole (0.4 g; 5.9 mmol) in 10 mL of MeCN was added 0.17 mL (1.9 mmol) of PCl$_3$, followed by 0.86 mL (6.2 mmol) of Et$_3$N. To this mixture was added a solution of 3.0 g (0.55 mmol) of 12 in 12 mL of MeCN dropwise. The reaction mixture was allowed to warm to ambient temperature and stirred 16 h. treated with 10 mL of 0.1 M triethylammonium bicarbonate solution, and concentrated in vacuo. Triethylamine then toluene were coevaporatcd from the crude residue, then the product was dissolved in dichloromethane. The organic phase was washed with 1.0 M triethylammonium bicarbonate (TEAB) solution, dried over sodium sulfate, and concentrated. Purification by flash chromatography on 300 mL of silica gel (wet packed with hexane/Et$_3$N (95:5)) eluting with 2-4-6-8-10-12-15% methanolic ammonia in dichloromethane afforded 1.95 g of product as a white solid. $^{31}$P NMR (CDCl$_3$) d 10.3, 10.2.

Synthesis of Lipid phosphoramidite 17: A solution of 540 mg (1 mmol) of 1,2-di-O-palmityl rac-glycerol in 10 mL of pyridine was treated with 195 mg (1.2 mmol) of carbonyldi-imidazole and the resulting mixture stirred at ambient temperature overnight. To this mixture was added 570 mg (1 mmol) of the amino alcohol as a solution in 3 mL of DMF. The mixture was warmed to 40° C. overnight, after which time $^1$H NMR analysis of an aliquot from the reaction indicated very negligible formation of product. The mixture was heated to 80° C. for 6 h (ca 1:1 product to starting material by $^1$H NMR), then concentrated in vacuo. The crude residue was applied to a column of 125 mL of SiO2 gel (Packed in hexanes) and the product eluted with a gradient of 20-50% EtOAc in hexanes (with 2% TEA) to afford 500 mg (44%) of intermediate 16 as a clear wax. (16: $^1$H NMR (300 MHz, CDCl$_3$) d 7.42 (d, J=7.2 Hz, 2H), 7.30-7.18 (m, 7H), 6.76 (d, J=8.2 Hz, 4H), 5.34 (br t, 1H), 4.20-3.25 (overlapping signals), 3.16 (m, 2H), 1.53 (m), 1.24 (m), 0.86 (t, J=6.5 Hz, 6H). Alcohol 16 (500 mg; 0.44 mmol) was dissolved in 4 mL of CH$_2$Cl$_2$ and 0.15 mL (2 equiv) of DIPEA. To this solution was added 0.15 mL (0.66 mmol) of 2-cyanoethyl (N,N-diisopropylamino) chlorophosphoramidite. After 3 h, TLC showed conversion to 2 spots and the mixture was diluted with CH$_2$Cl$_2$ and washed with NaHCO$_3$ solution. The organic phase was dried over Na$_2$SO$_4$ and concentrated. The crude residue was applied to a column of 50 mL of SiO$_2$ gel (packed in hexanes) and the product eluted with 20% EtOAc in hexanes (containing 2% TEA) to afford 350 mg (59%) of phosphoramidite 17 as a colorless wax. $^{31}$P NMR (CDCl$_3$) d 151.55, 151.08.

Automated synthesis of lipid-oligo: Phosphoramidite 17 was coupled to the 5'-end of a T-3mer (prepared by standard automated DNA synthesis on an ABI 394 instrument) using a modified coupling cycle consisting of two 30 minute exposures of an 0.1 M solution of 17 in 40% THF in MeCN to the column. In-line trityl analysis indicated a coupling efficiency of 94% for amidite 17.

Chloroformate 19: To a stirred solution of 3 g (5.03 mmol) of 1,2-di-O-octadecyl-sn-glycerol 21 in 60 mL of toluene was added 20 mL of a 1.93 M solution of phosgene. Additional phosgene solution (2×10 mL; 15.4 equiv phosgene total) was added until no further alcohol starting material remained (by $^1$H NMR analysis of concentrated aliquots). The excess phosgene and HCl was removed by aspirator and the reaction mixture was concentrated in vacuo to afford 3.3 g (98%) of the desired chloroformate 19 as a white powder. $^1$H NMR (300 MHz, CDCl$_3$) d 4.45 (dd, J=11.22, 3.69 Hz, 1H), 4.34 (dd, J=11.22, 6.15 Hz, 1H), 3.65 (m, 1H), 3.56-3.40 (m, 6H), 1.53 (m, 4H), 1.24 (m, 62H), 0.87 (t, J=6.36 Hz, 6H); $^{13}$C NMR (75 MHz, CDCl$_3$) d 75.90, 71.91, 71.35, 70.93, 69.36, 31.99, 29.96-29.44 (overlapping signals from hydrocarbon chains), 26.13, 26.04, 22.76, 14.18.

Conjugate 20: To a stirred solution of 2.25 g (3.95 mmol) of 10 in 60 mL of pyridine was added 2.6 g of the distearyl glycerol chloroformate 18. $^1$H NMR analysis of a concentrated aliquot after 2 h revealed no remaining chloroformate and the mixture was concentrated in vacuo. The crude residue was combined with material similarly prepared from 0.5 g (0.88 mmol) of 10 and 0.58 g of the chloroformate and the combined lots purified by flash silica gel chromatography on a column of 100 mL of silica gel (packed in hexanes containing 2% triethylamine) eluting with 200 mL hexanes, then 250 mL each of 10-20 and 30% EtOAc in hexanes, 500 mL 40% EtOAc in hexanes, then 250 mL each of 50-60-70 and 80% EtOAc in hexanes, and finally with 250 mL of EtOAc. The product containing fractions were concentrated to afford 3.3 g (57%) of the conjugate 20.

Phosphoramidite 21: To a stirred solution of 3.8 g (3.26 mmol) of the conjugate in 25 mL of CH$_2$Cl$_2$ was added 1.14 mL (6.52 mmol) of diisopropylethylamine then 1.09 mL (4.88 mmol) of 2-cyanoethyl N,N-diisopropylchloro-phosphoramidite. After 2 hours, the mixture was diluted with CH$_2$Cl$_2$ and washed with saturated NaHCO$_3$ solution, dried over Na$_2$SO$_4$, and concentrated. The crude residue was purified by flash silica gel chromatography on a column of 125 mL of silica gel (packed in hexanes containing 2% triethylamine) eluting with 100 mL hexanes, then 250 mL each of 10 and 20% EtOAc in hexanes, 500 mL 30% EtOAc in hexanes, then 250 mL of 50% EtOAc in hexanes. The product containing fractions were concentrated to afford 4.2 g (95%) of the phosphoramidite 21. $^{31}$P NMR (CDCl$_3$) d 151.52, 151.08.

Example 2

Preparation and Functional Properties of PEG Conjugated and Cholesterol-Derivatized Nucleic Acid Ligands A PEG 3400 Conjugate of a Nucleic Acid Ligand Retains the Binding Affinity of the Non-Conjugated Molecule The ability of a bFGF ligand/PEG-3400 conjugate to bind bFGF was tested. Molecule 225t3 (SEQ ID NO:10), a high affinity DNA ligand to bFGF, was chosen for conjugation with PEG via a primary amine-NHS coupling reaction. Ligand 225t3 has a binding affinity of 1 nM and folds into a blunt ended hairpin with a Tm of 68° C. Ligand 225t3 was modified with a 3'-amino-modifier C7 CPG (Glen Research, Sterling, Va.) using standard DNA synthesis methods and will be referred to as 225t3N (SEQ ID NO:11). 225t3N was reacted with the N-hydroxysuccinimidyl (NHS) active ester of PEG (avg. MW 3400) in 20% (v/v) dimethoxy formamide 80% (v/v) 0.5 M sodium bicarbonate buffered at pH 8.5. The resulting conjugate, 225t3N-PEG-3400 (SEQ ID NO:14), was purified from the free DNA on a 12% polyacrylimide/7 M urea gel. The conjugate was 5' end-labeled with $^{32}$P and a binding assay was performed. 225t3N-PEG-3400 (SEQ ID NO:14) binds to bFGF with the same affinity ($K_d$=1 nM) as 225t3.

Conjugation of PEG-20.000 to a Thrombin DNA Ligand.

Thrombin DNA ligand NX256 (SEQ ID NO:9) (FIG. 1D) containing an amino and a disulfide functionality was prepared using standard DNA synthesis methods and procedures on a Biosearch 8909 DNA/RNA synthesizer with dT-5'-LCAA-500 Å controlled-pore glass solid support and commercially available phosphoramidite reagents. Deprotection was followed by ion exchange HPLC purification. The 5' terminal disulfide bond was reduced by incubating the DNA in a solution 50 mM dithiolthreitol (DTT) at 37° C. for 30 min. The reduced DNA (containing a 5' terminal thiol) was run through a Nap-5 size exclusion column and the void volume, containing the DNA but not the DTT, was collected into a reaction vessel containing the maleimide derivatized PEG under an argon blanket. All solutions were purged with argon to remove oxygen. The reaction was kept at 40° C. for 1 h. The progress of the reaction was monitored by removing small aliquots and analyzing them by electrophoresis on 8%/7 M urea polyacrylamide gels. At the end of the 1 hour incubation period, the reaction was essentially complete, and at this time an equal volume of methylene chloride was added to the reaction mix and the vessel shaken until a milky white suspension formed. The mix was spun at 14,000 rpm in an eppendorf centrifuge until the layers separated. The aqueous layer contained the free Nucleic Acid Ligand and was discarded. The product (PEG-20,000 modified DNA ligand NX256, referred to as NX256-PEG-20,000; SEQ ID NO:13) (FIG. 1G) was further purified using ion exchange chromatography followed by reverse phase desalting and lyophilization to a white powder. This material was used to determine the effect of PEG modification on the pharmacokinetic behavior of the DNA Nucleic Acid Ligand (vide infra). PEG-10,000 modified ligand NX256, referred to as NX256-PEG-10,000, was prepared in an analogous manner.

$T_m$ Values for PEG Conjugates

PEG functionality can also be introduced via the thiophosphate-maleimide reaction. We introduced the thiophosphate group into the thrombin DNA ligand at the 5'-end by the standard phosphoramidite method using commercially available reagents (this ligand is referred to as T-P4) (FIG. 1F, SEQ ID NO:12). The conjugation to the maleimide-containing PEG is analogous to the sulfhydryl-maleimide reaction described above. The PEG-conjugated ligands are referred to as T-P4-PEG-10,000 and T-P4-PEG-20,000 (SEQ ID NO:15). Melting temperatures ($T_m$) for T-P4-PEG-10,000, T-P4-PEG-20,000 and T-P4-DNA ligands were determined from the first derivative of the optical absorbance at 260 nm vs. temperature plots. The Tm values for T-P6-PEG-10,000, T-P6-PEG-20,000 and T-P6 were 40° C. for all three ligands. These data and the bFGF-PEG-3400 Nucleic Acid Ligand binding data reported above, suggest that conjugation to PEG does not affect Nucleic Acid Ligand structure.

A Cholesterylated bFGF Ligand Retains the Binding Affinity of the Non-Cholesterylated Molecule Cholesterol can be introduced into a Nucleic Acid Ligand, at any position in the sequence, by the standard solid phase phosphoramidite method. For example, we incorporated a tetraethyleneglycol cholesterol phosphoramidite (Glen Research, Sterling, Va.) at the 3' end of ligand 225t3 (FIG. 1E; SEQ ID NO:10) to produce ligand 225t3-Cholesterol Following purification on a 12% polyacrylimide/7 M urea gel, 225t3-Chol was 5' end-labeled with $^{32}P$ and a binding assay performed. The binding affinity of 225t3-Chol was identical ($K_d$=1 nM) to that of 225t3.

Example 3

Nucleic Acid Ligand-Liposome Formulation and Anticoagulation Activity

A. Preparation of NX232 Liposomes

Figure 1B:
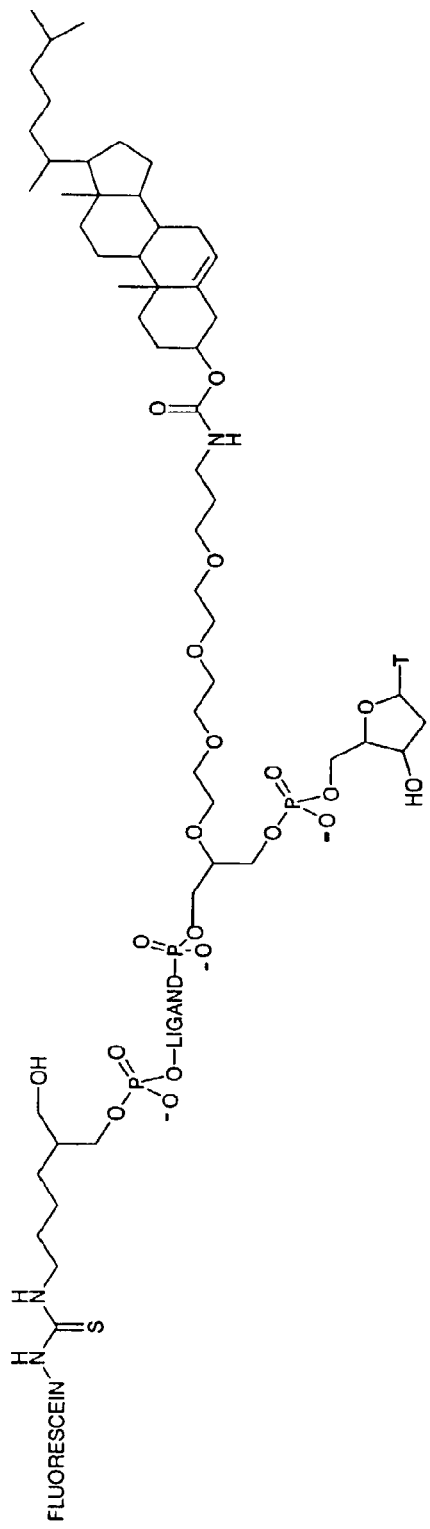
Figure 1C:
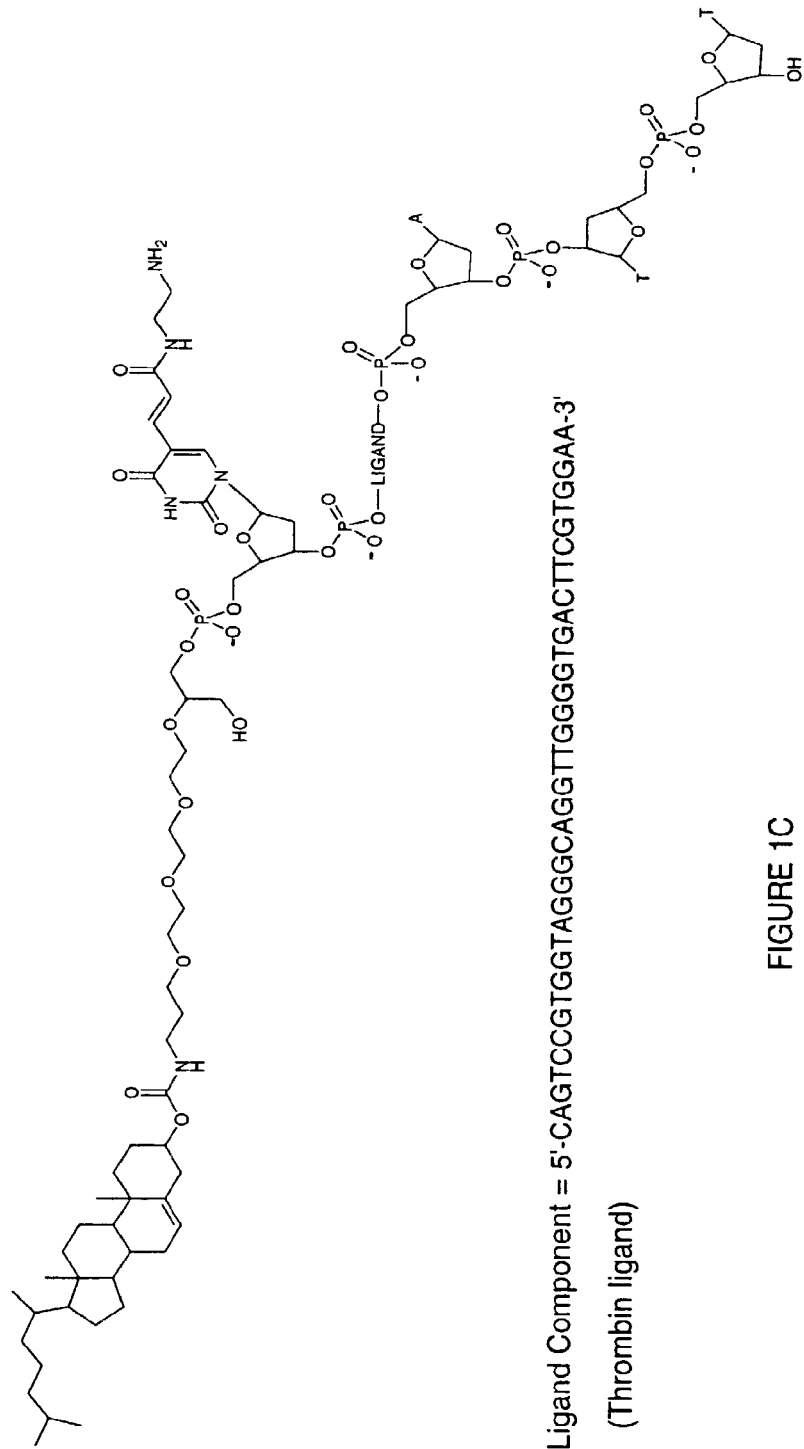
Figure 1D:
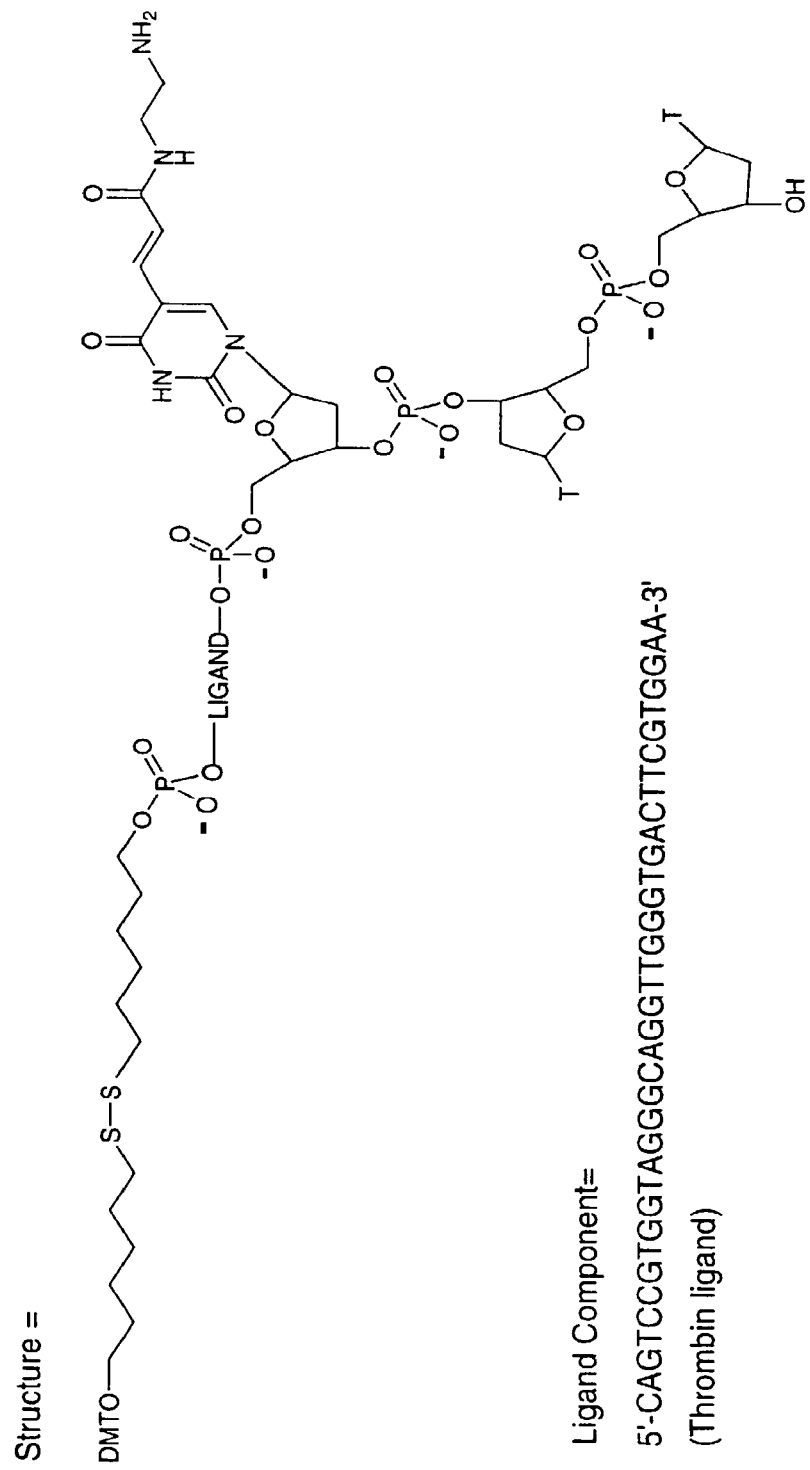
Figure 1E:
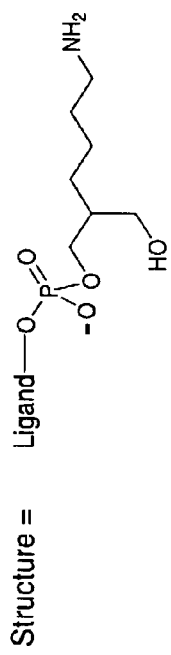
Figure 1F:
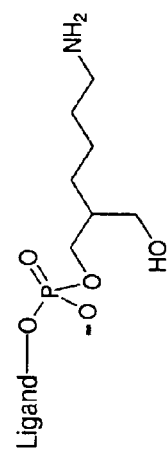
Figure 1G:
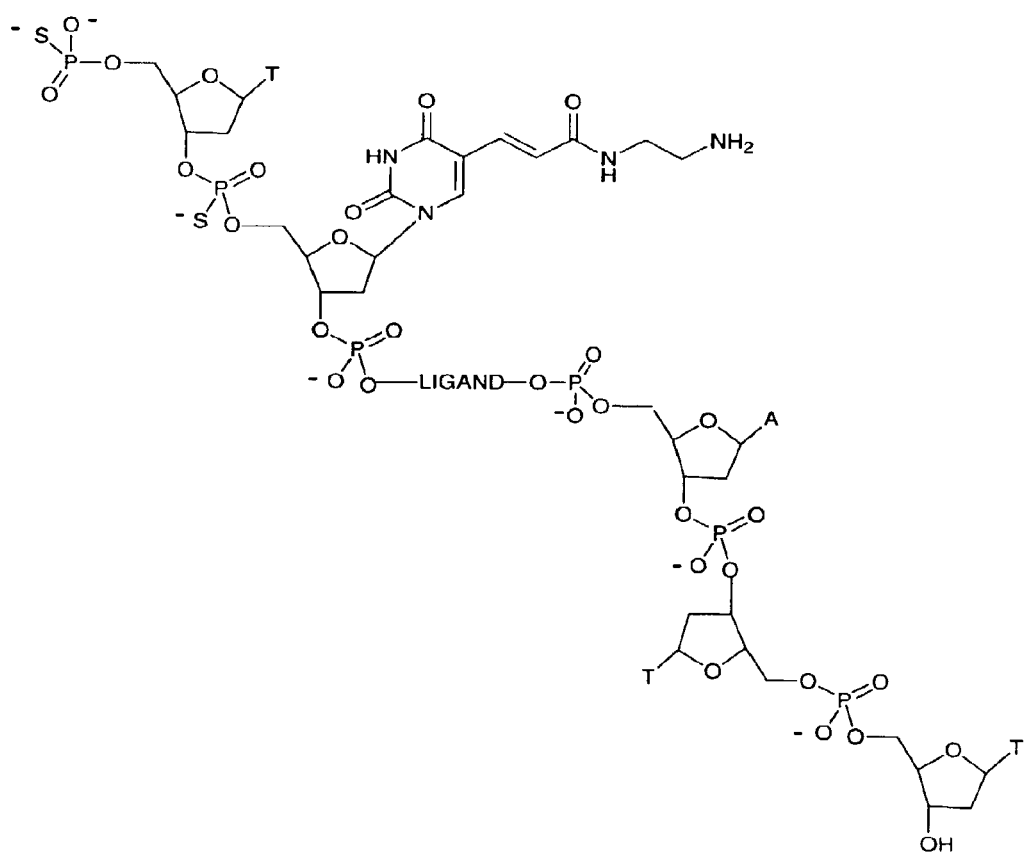
Figure 1I:
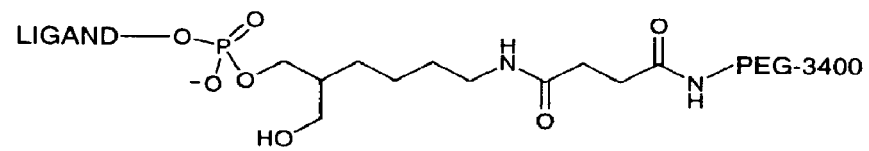
Figure 1J:
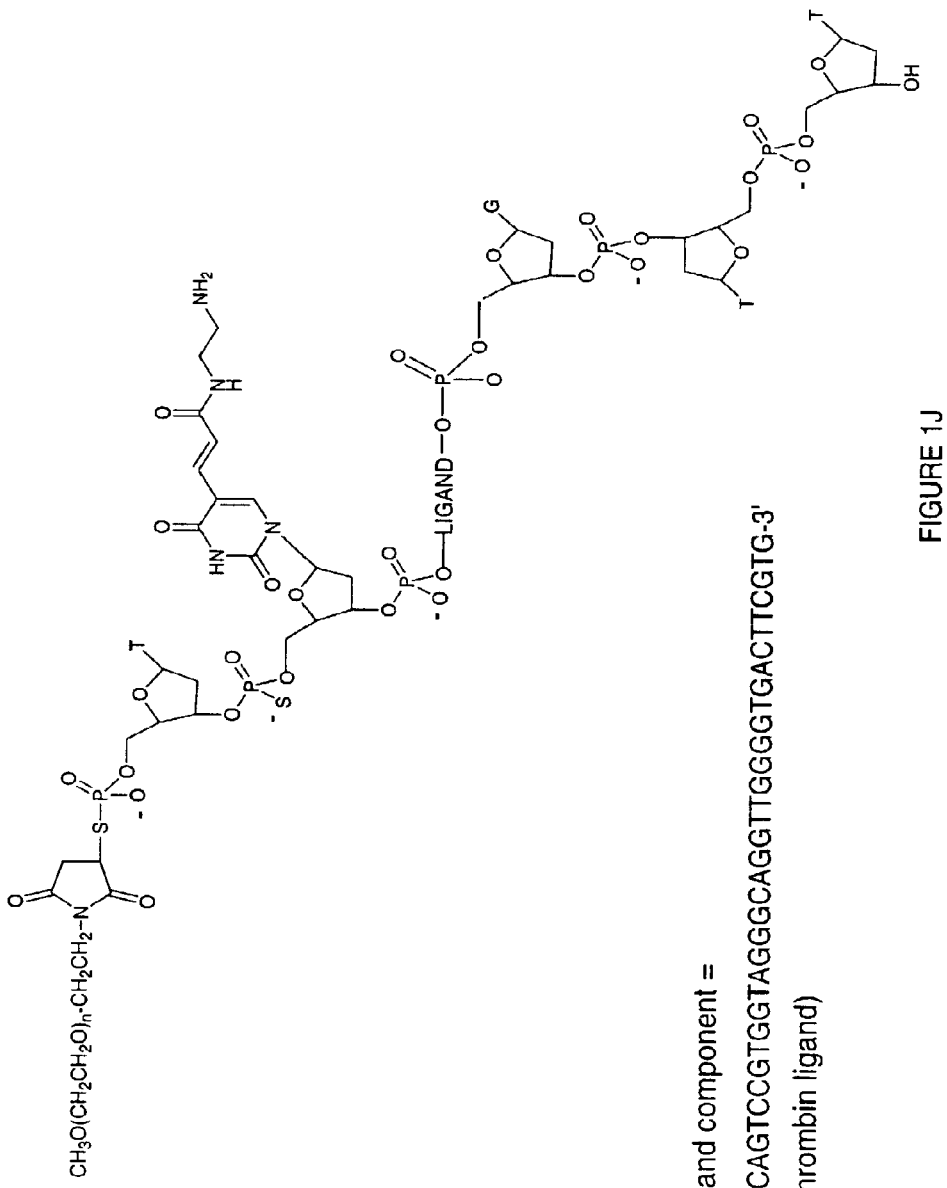

Fluorescein-labeled, cholesterol-derivatized NX232 (FIG. 1B; SEQ ID NO:7) was incorporated into Liposomes composed primarily of distearoylphosphatidylcholine (DSPC) and cholesterol (Chol) in a 2:1 molar ratio.

Eight formulations of NX232 Liposomes containing DSPC:Chol (2:1 mole ratio) were prepared. The mole percentage of NX232 was varied from 0.01 through 0.1 mole %, based upon total lipids present. The compositions (A-H) are reported in Table 1. Increasing fractions of the cationic lipid 1,2-dioleoyl-3-trimethylammonium-propane (DOTAP) were included in formulations D-H to evaluate the effect of positive charges on the strength of the association between NX232 and the Liposome surface.

TABLE 1

Summary of Liposome NX232 Preparations - Lipid compositions and mole percentage of NX232

| Compound[a] | M.W. | A | B | C | D | E | F | G | H |
|---|---|---|---|---|---|---|---|---|---|
| mole fractions: | | | | | | | | | |
| DSPC | 790.15 | 2.0 | 2.0 | 2.0 | 2.0 | 2.0 | 2.0 | 2.0 | 2.0 |
| Chol | 386.7 | 1.0 | 1.0 | 1.0 | 1.0 | 1.0 | 1.0 | 1.0 | 1.0 |
| DOTAP | 698.55 | 0.0 | 0.0 | 0.0 | 0.0 | 0.0012 | 0.003 | 0.006 | 0.012 |
| NX232 | 12,424.1 | 0.0003 | 0.0008 | 0.0015 | 0.003 | 0.0003 | 0.0008 | 0.0015 | 0.003 |
| (NX232 mole-%:) | | 0.01 | 0.025 | 0.05 | 0.1 | 0.01 | 0.025 | 0.05 | .0.1 |
| Weight Ratios: | | | | | | | | | |
| DSPC | | 1.0 | 1.0 | 1.0 | 1.0 | 1.0 | 1.0 | 1.0 | 1.0 |
| Chol | | 0.2447 | 0.2447 | 0.2447 | 0.2447 | 0.2447 | 0.2447 | 0.2447 | 0.2447 |
| DOTAP | | 0.0 | 0.0 | 0.0 | 0.0 | 0.0005 | 0.0013 | 0.0027 | 0.0053 |
| NX232 | | 0.0024 | 0.0059 | 0.0118 | 0.0236 | 0.0024 | 0.0059 | 0.0118 | 0.0236 |
| Amounts per ml[b]: | | | | | | | | | |
| DSPC | | 20.0 | 20.0 | 20.0 | 20.0 | 20.0 | 20.0 | 20.0 | 20.0 |
| Chol | | 4.894 | 4.894 | 4.894 | 4.894 | 4.894 | 4.894 | 4.894 | 4.894 |
| DOTAP | | 0.0 | 0.0 | 0.0 | 0.0 | 0.011 | 0.027 | 0.053 | 0.106 |
| NX232 | | 0.047 | 0.118 | 0.236 | 0.472 | 0.047 | 0.118 | 0.236 | 0.472 |

[a]DSPC = distearoylphosphatidylcholine; Chol = cholesterol; DOTAP = 1,2-dioleoyl-3-trimethylammonium-propoane.
[b]final total concentration for all components = 25 mg/ml.

Lipids and NX232 were co-solublized in a mixture of chloroform, methanol and water ($CHCl_3$:MeOH:$H_2O$, 1:5:1, v:v:v) and transferred to test tubes. Lipid films were formed by evaporating the solvent under nitrogen flow. The dried lipid films were stored under vacuum until hydration. The films were hydrated at 65° C. with an aqueous 9% sucrose solution (~250 mM) containing 10 mM tris(hydroxymethyl) aminomethane (TRIS) and 1 mM ethylenediaminetetraacetic acid (EDTA) at pH 7.4. Following hydration, the lipids were sonicated using a probe-type sonicator for approximately 6-9 minutes and then cooled to room temperature.

Figure 2:
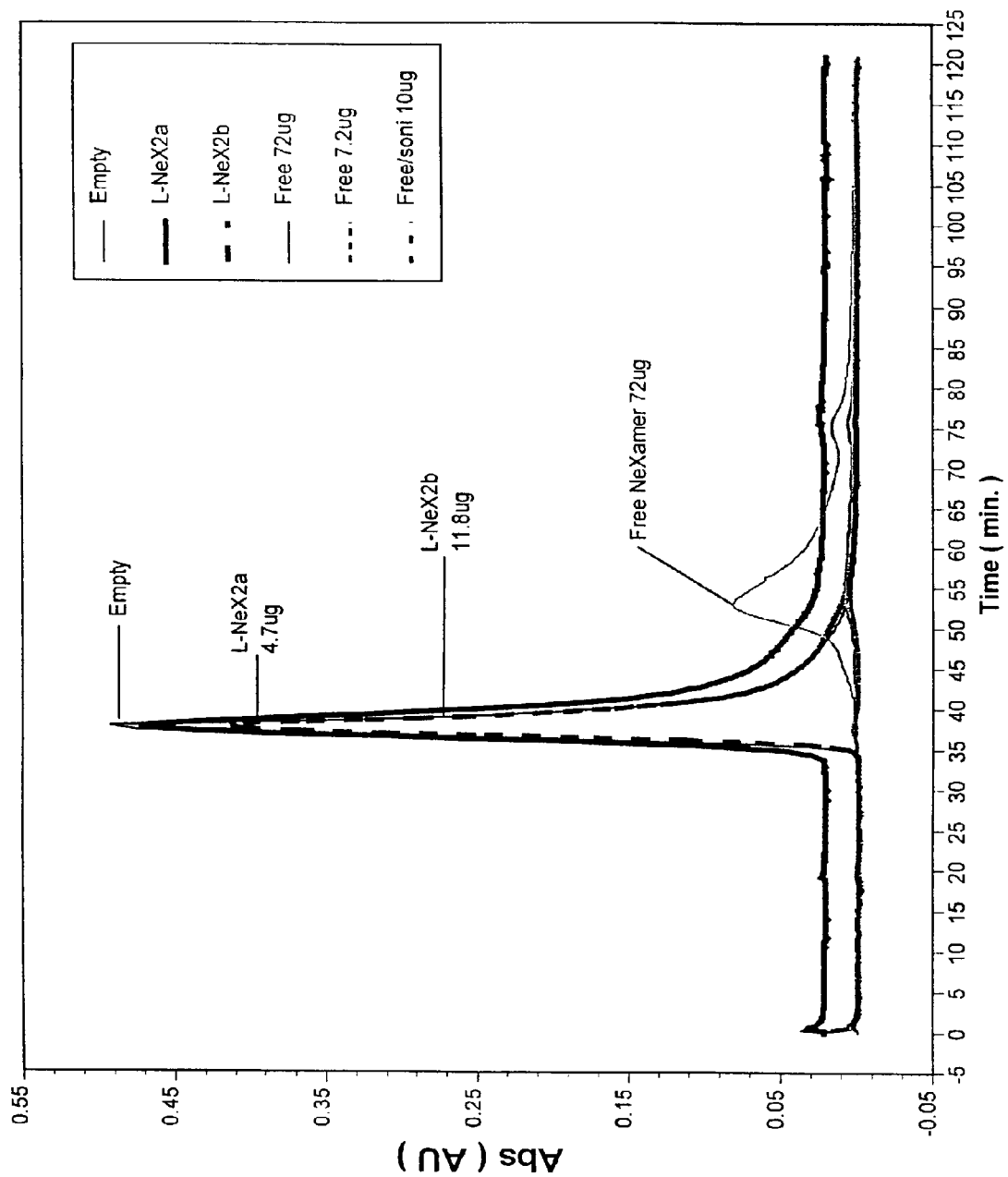
FIG. 2 shows gel permeation chromatograms for empty Liposomes (Empty), Liposomes with 4.7 mg NX232 (L-NeX2a), Liposomes with 11.8 mg NX232 (L-NeX2b), free NX232 at 72 mg (Free 72 mg), free NX232 at 7.2 mg (Free 7.2 mg), and free NX232 at 10 mg which had been sonicated (Free/soni 10 mg).

Unincorporated NX232 (FIG. 1B; SEQ ID NO:7) was removed by FPLC gel permeation chromatography using Sephacryl S-300, eluting with the sucrose hydrating solution described above. The gel permeation chromatograms for empty Liposomes (Empty), Liposomes with 4.7 μg NX232 (L-NeX2a), Liposomes with 11.8 μg NX232 (L-NeX2b), free NX232 at 72 μg (Free 72 μg), free NX232 at 7.2 μg (Free 7.2 μg), and free NX232 at 10 μg which had been sonicated (Free/soni 10 μg) are shown in FIG. 2. The chromatograms indicate that good separation of free NX232 and Liposomes is possible. The free NX232 chromatogram at 72 μg shows a distinct peak following the Liposomes (elution peak at ~53 minutes); however, 72 µg of the free Nucleic Acid Ligand had to be added in order to be visualized by UV absorbance at 254 nm. No similar peak can be discerned for free NX232 at 7.2 µg. Therefore, with the liposomal preparations, the NX232 amounts (4.7 µg for "a" and 11.8 µg for "b") may have been insufficient to show up as a distinct peak on the chromatogram.

Based on the absorbance measurements at 254 nm, NX232 is incorporated nearly quantitatively into these Liposomes. Since only approximately 50% of the NX232 molecules were fluorescein labeled, quantitative incorporation suggests that the presence of the fluorescein label does not significantly affect association of NX232 with Liposomes.

B. In Vitro Assay of Clotting Inhibition

NX232 (FIG. 1B; SEQ ID NO:7) contains the DNA sequence of a high affinity Nucleic Acid Ligand to thrombin. Thrombin is a critical component of the blood clotting cascade. The inhibition of the proteolytic activity of thrombin is known to decrease the ability of blood to clot. The activity of the various NX232 formulations were evaluated using a fibrin/thrombin clotting assay to measure anticoagulation activity. A buffer solution of 50 mM TRIS, 100 mM NaCl, 1 mM MgCl$_2$, and 0.1% polyethylene glycol (PEG$_{8000}$) (MW 8,000) at pH 7.4 was used for the assay. In the final 300 µl assay mixture, fibrinogen at a concentration of 2.5 mg/ml and thrombin at 1 National Institutes of Health (NIH) unit were added to glass test tubes. All solutions and containers were warmed to and maintained at 37° C. for coagulation measurements. Coagulation times are reported in Table 2.

TABLE 2

Effect of Processing on NX232 Anticoagulation Activity

| Preparation | NX232 (µg/300 µl) | Clot Time (sec.) |
| --- | --- | --- |
| Control (no additions) | — | 18-20 |
| NX232, unsonicated | 7.08 | 49-51 |
|  | 3.54 | 19-21 |
| NX232, sonicated | 7.08 | 45-50 |
|  | 3.54 | 20-25 |
| Liposomes: |  |  |
| Preparation A | 7.08 | 57-59 |
|  | 3.54 | 26-28 |
| Preparation B | 7.08 | 56-59 |
|  | 3.54 | 25-27 |

These results indicate that typical Liposome processing conditions, including sonication, solubilization, heating and drying, do not affect the anticoagulation activity of NX232. In addition, liposomal association does not affect the ability of NX232 to bind and inhibit its target.

Example 4

Pharmacokinetic Properties of Cholesterol, Diacyl Glycerol Dialkyl Glycerol, and PEG Modified DNAS The pharmacokinetic properties of thrombin DNA ligands NX229, NX232, NX253, NX253+Liposome, and NX256-PEG20K were determined (see FIGS. 1A-1C, 1G for molecular descriptions) (SEQ ID NOS:6-8, 13). Each oligonucleotide was diluted in PBS to a solution concentration of 0.5-1.0 mg/ml based on UV absorption at 260 nm and an extinction coefficient of 0.033 µg oligo/ml. In all but one study, 6 rats received 0.5-1.0 mg oligonucleotide/kg animal weight and plasma samples were taken at various times from 1 minute to 4 hours. One rat was used in the study in which NX253 was tested. The plasma samples and quality control samples were analyzed using a hybridization assay. The hybridization assay utilized a capture oligonucleotide that contains a complementary sequence to the 5'-end of the DNA ligands conjugated to an iron oxide (FeO) bead (FeO-spacer-5'-d (GTC AGG CAC CAT CCC-3') (SEQ ID NO: 1) where spacer=(dT)$_8$), and a detection oligonucleotide containing a biotin group at the 3'-end (5' d-CCC CAC TGA AGC ACC-spacer-3'-biotin-biotin, where spacer=(dT)$_{10}$) (SEQ ID NO:2). The amount of the biotin oligonucleotide attached to the bead was quantitated with the straptavidin-linked alkaline phosphatase, using CSPD-Sapphire as the luminescent substrate.

Figure 3:
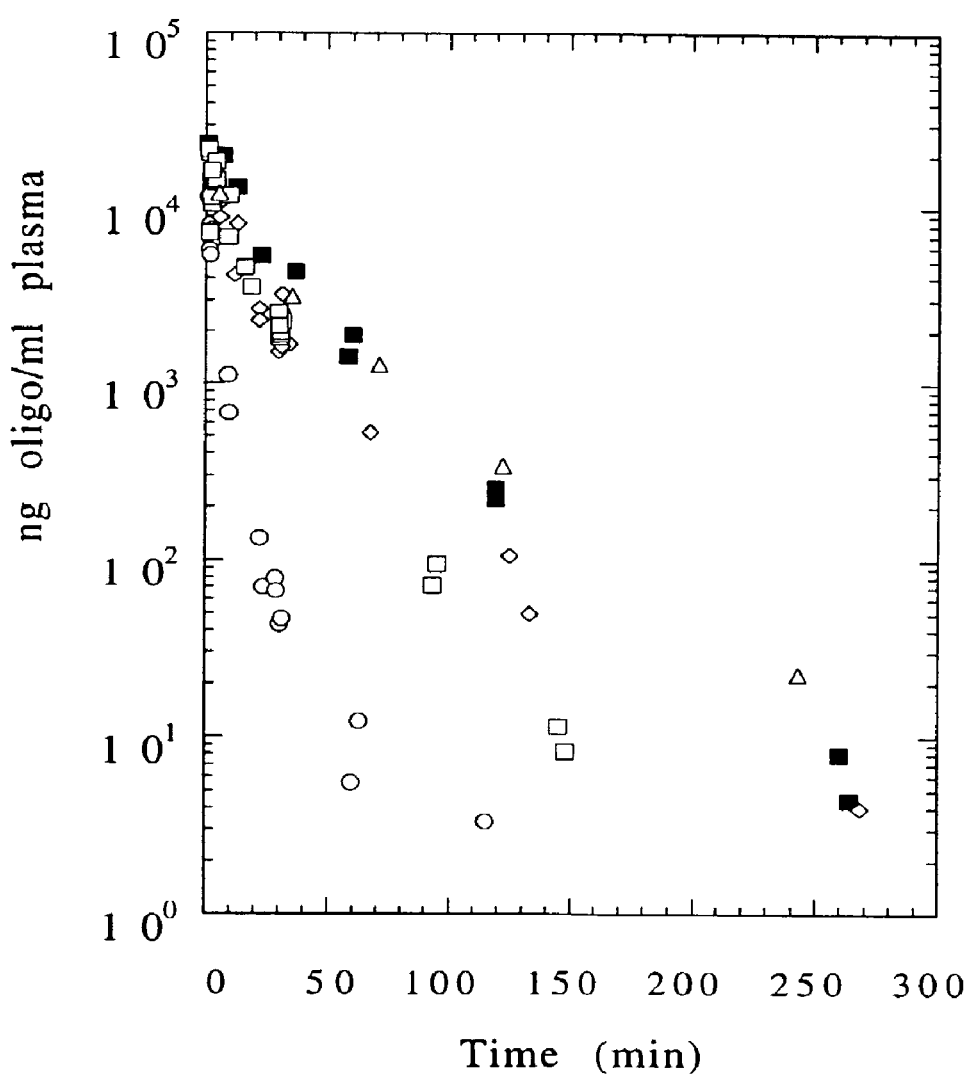
FIG. 3 summarizes the data for the plasma concentration of NX229, NX232, NX253, NX253+Liposome, and NX256-PEG20K as a function of time following the bolus injection.

Data for the plasma concentration of NX229, NX232, NX253, NX253+Liposome, and NX256-PEG20K (SEQ ID NOS:6-8, 13) as a function of time following the bolus injection are summarized in FIG. 3. The plasma concentrations of NX232, NX253, NX253+Liposome, and NX256-PEG20K as a function of time are considerably greater compared to that of NX229 (SEQ ID NO:6). All of these oligonucleotides share the same thrombin binding module (d(CAG TCC GTG GTA GGG CAG GTT GGG GTG ACT TCG TGG)) (SEQ ID NO:3). The plasma concentration of an oligonucleotide as a function of time can be significantly increased by introducing appropriate functional groups into the oligonucleotide. Prolonged plasma half-life of a cholesterol-containing oligonucleotide compared to the control (non-cholesterol-containing) oligonucleotide has been observed previously (de Smidt et al., Nucl. Acids Res., 19: 4695 (1991))

Figure 4:
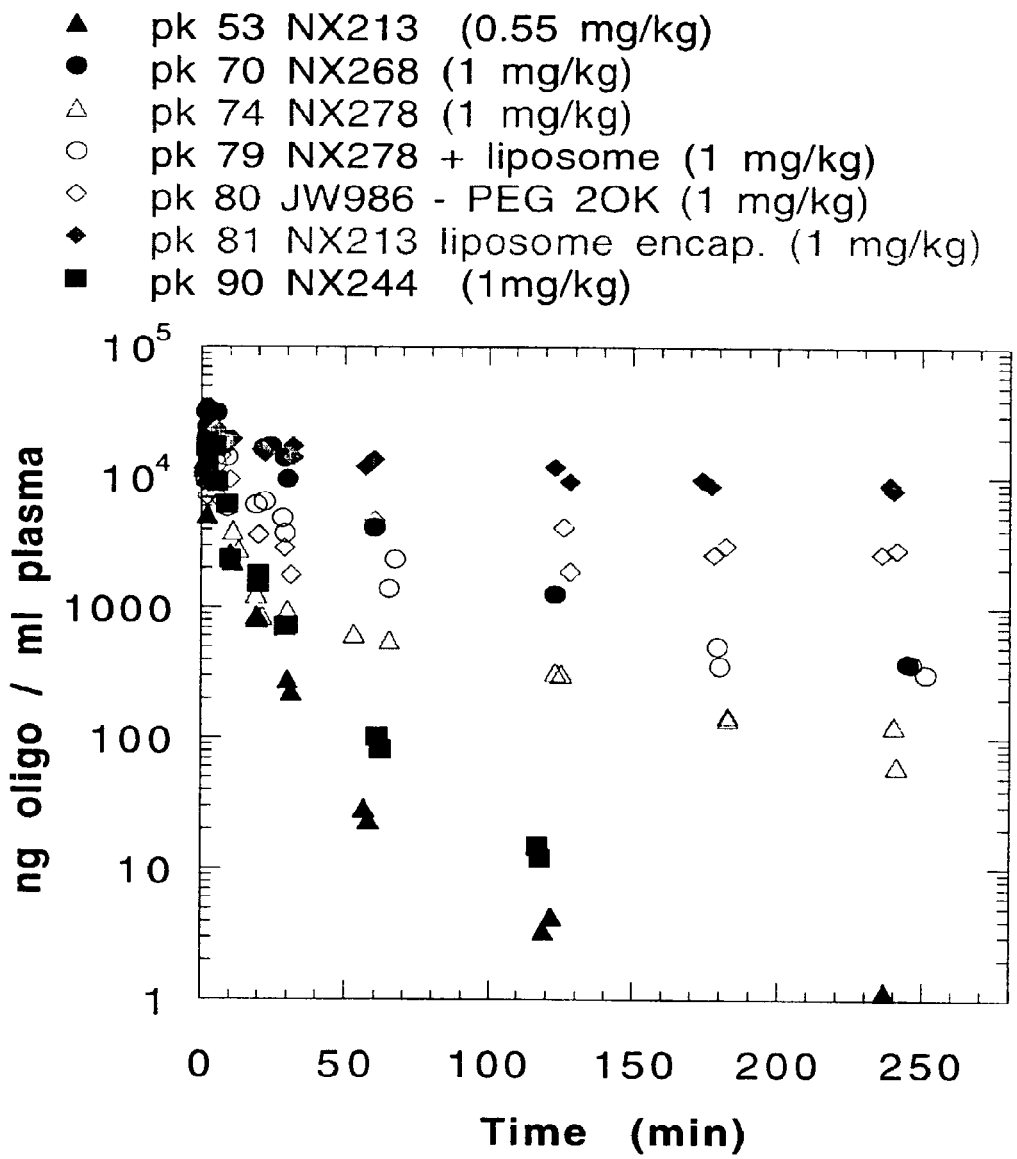
FIG. 4 summarizes the data for the plasma concentration of NX213 (SEQ ID NO:21), NX268 (SEQ ID NO:16), NX278 (SEQ ID NO:19), NX278+liposome, JW986 (SEQ ID NO:20), NX213 liposome encapsulated, and NX244 (SEQ ID NO:22) as a function of time following the bolus injection.

The plasma pharmacokinetic properties of a wide number of Nucleic Acid Ligands that have various functional groups attached to the base sequence of NX213 (see FIG. 1 for molecular description), as well as some liposomal formulations of these oligonucleotides have been assessed. These data are summarized in FIG. 4 (SEQ ID NOS:16, 19, 21, 22 and 29). The formulation with the slowest clearance rate was where NX213 (FIG. 1P; SEQ ID NO:21) was encapsulated within liposomes.

Figure 5:
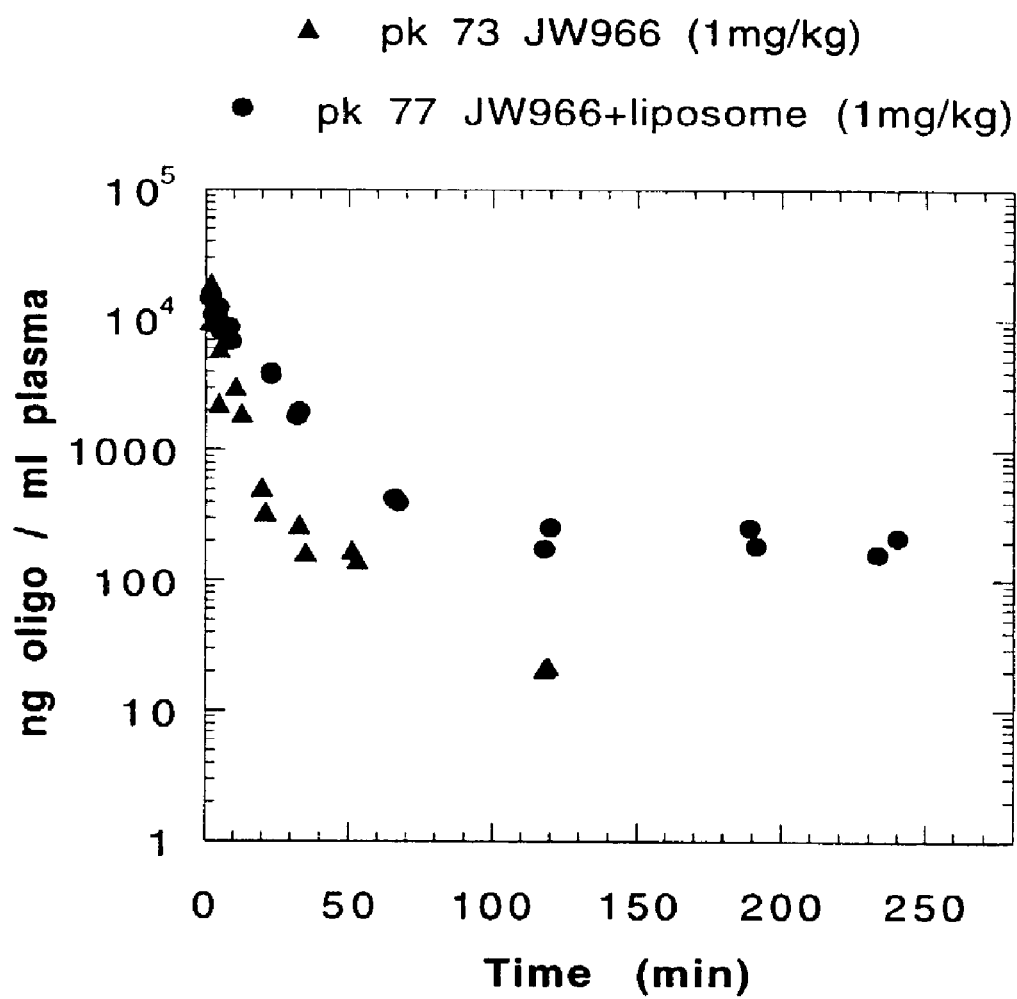
FIG. 5 summarizes the data for the plasma concentration of JW966 (SEQ ID NO:18) and JW966+liposome as a function of time following the bolus injection.

To determine the role of dialkyl glycerol DNA conjugates plus and minus liposomes PK studies 77 and 73 were carried out with the Thrombin DNA ligand dialkyl glycerol conjugate (See FIG. 1 for molecular description). These data are summarized in FIG. 5 (SEQ ID NO:18).

Figure 1K:
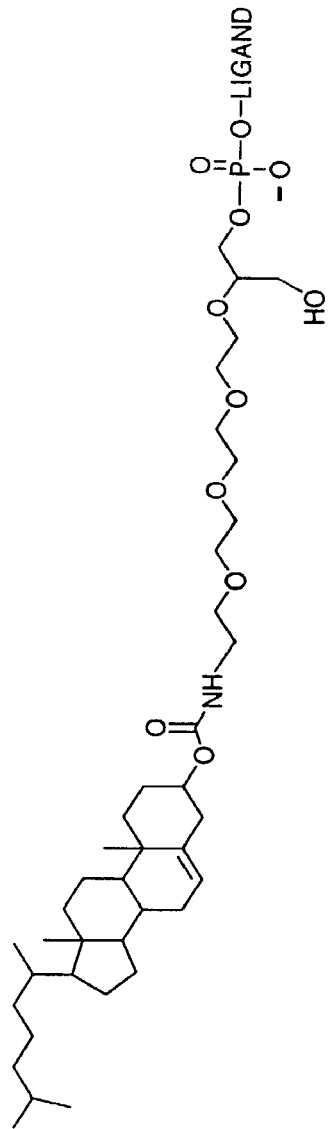
Figure 1M:
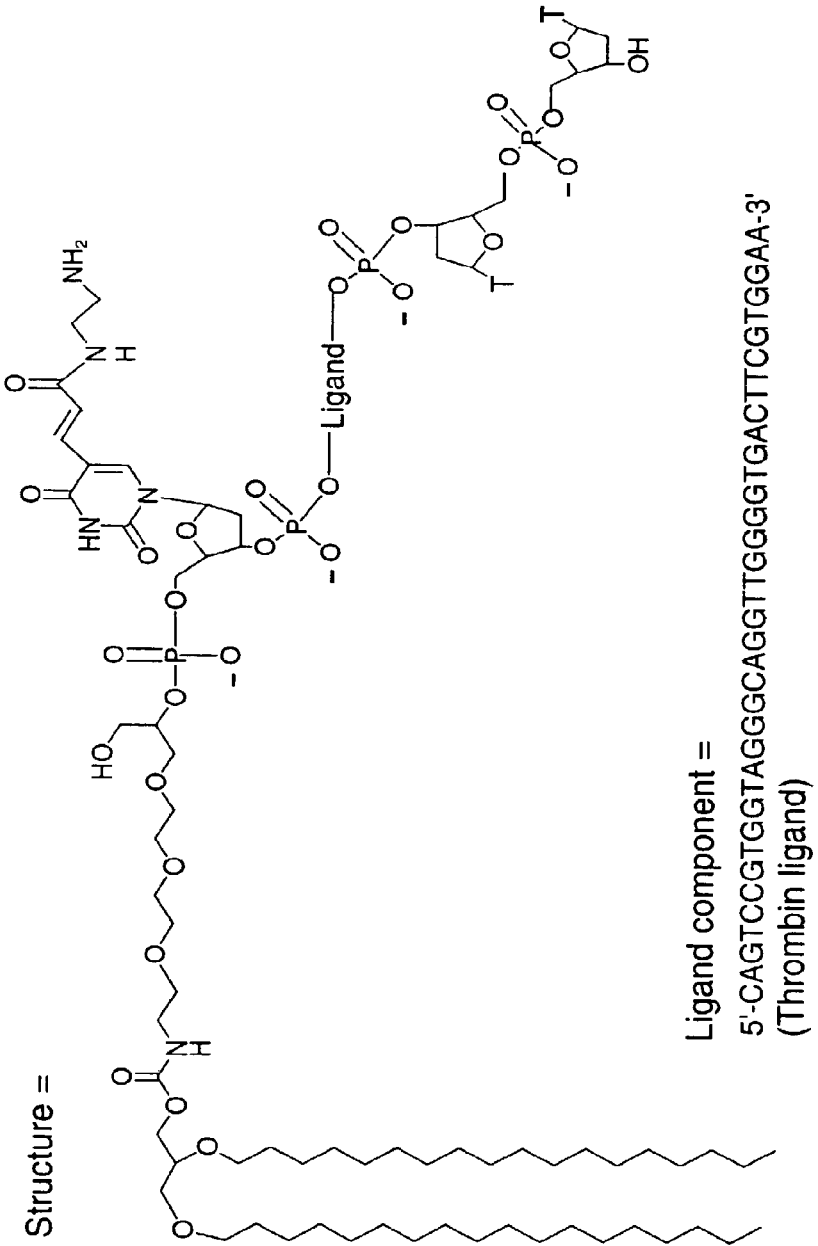
Figure 6:
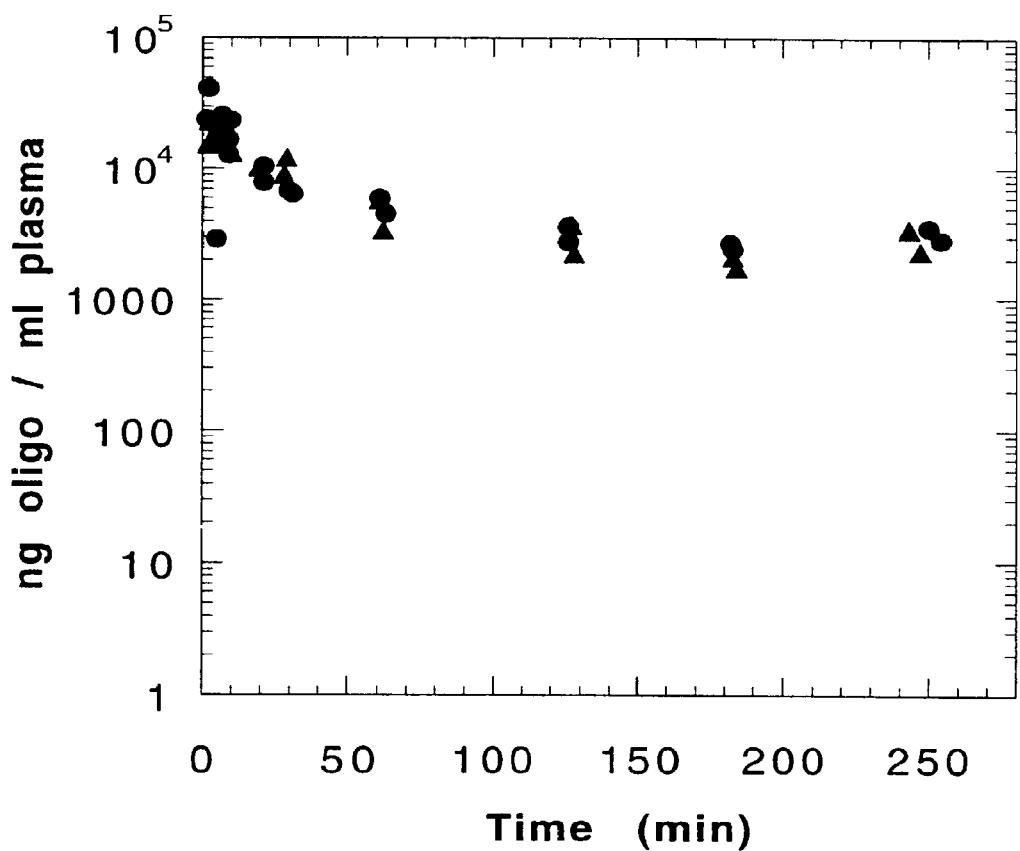
FIG. 6 summarizes the data for the plasma concentration of NX268 (SEQ ID NO:16) and NX268+liposome as a function of time following the bolus injection.

Cholesterylated VEGF oligonucleotides NX213 (NX268) (See FIG. 1K for molecular description; SEQ ID NO:16) were formulated with either PEG-liposomes or standard liposomes and the pharmacokinetics were evaluated (PK 85-86). These formulations contain oligonucleotides both on the inside and outside of the liposome. FIG. 6 (SEQ ID NO:16) shows the rat plasma levels of full length oligonucleotides as a function of time after injection. Both liposome formulations show similar oligonucleotide pharmacokinetics.

Figure 7:
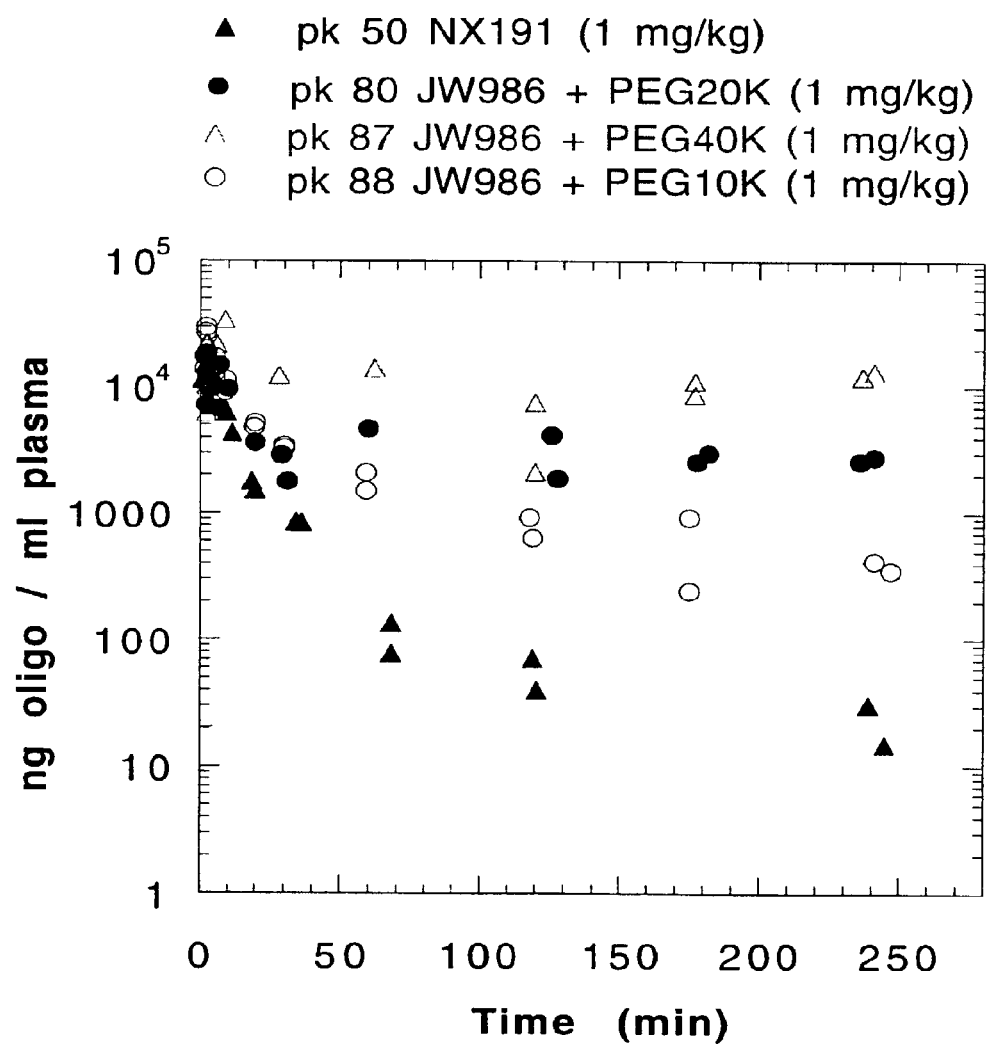
FIG. 7 summarizes the data for the plasma concentration of NX191 (SEQ ID NO:17), JW986+PEG20K, PEG40K, and PEG10K, (SEQ ID NO:29) as a function of time following the bolus injection.

To evaluate size dependence on clearance, 2' 0-methyl VEGF oligonucleotides with various PEG conjugates (See FIG. 1 for molecular description) (PK 50,80,87, &88) have been studied. FIG. 7 shows the comparison of the all 2' 0-methyl oligonucleotides plus PEG 40K, 20K, 10K, as well as in the absence PEG (SEQ ID NOS:17 and 29). These data demonstrate significantly slower plasma clearance with increasing size of the PEG conjugate.

Figure 1N:
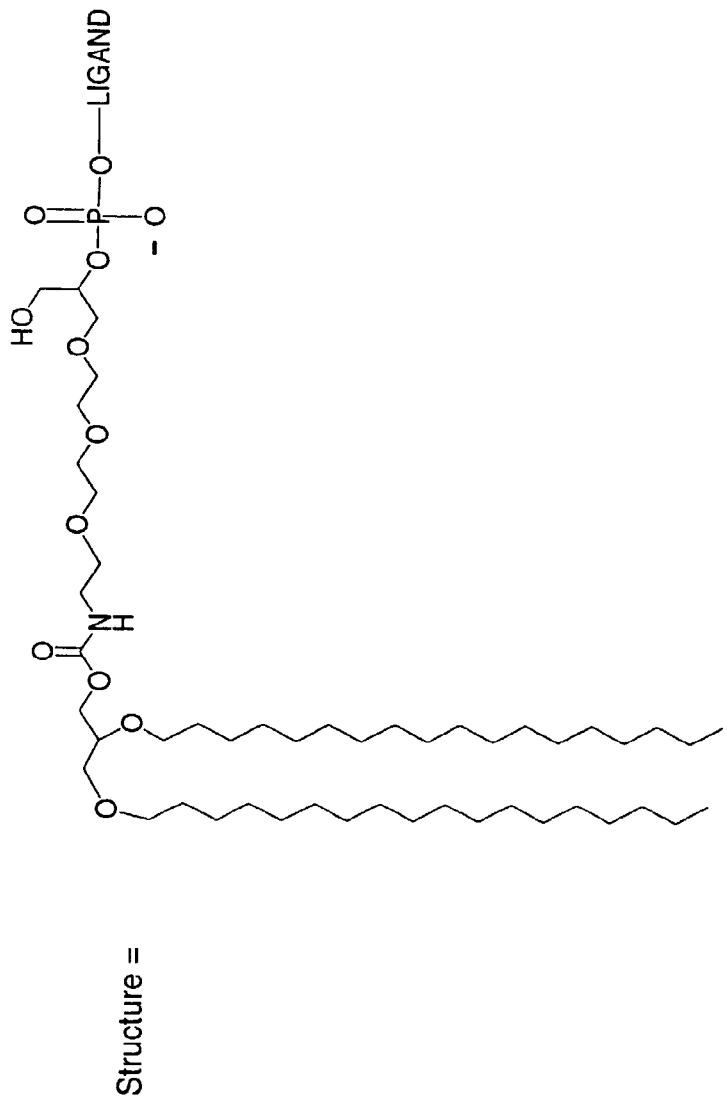
Figure 1:
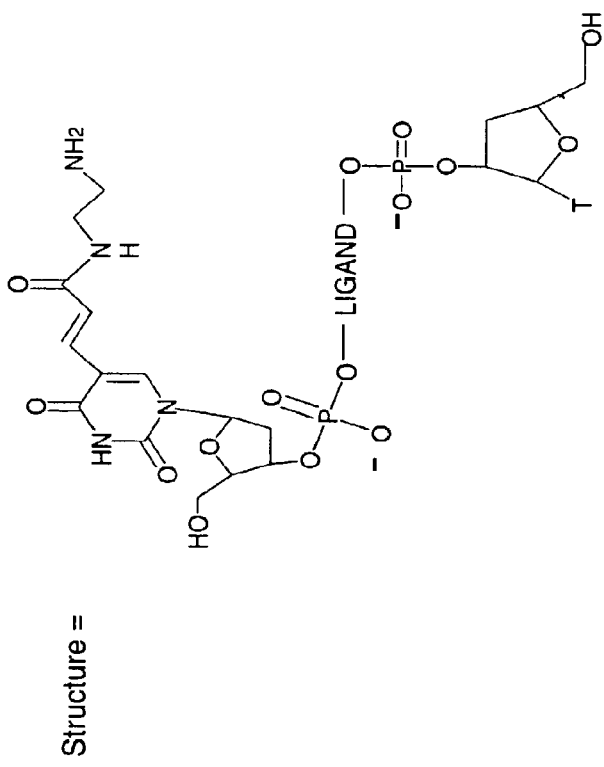
Figure 1R:
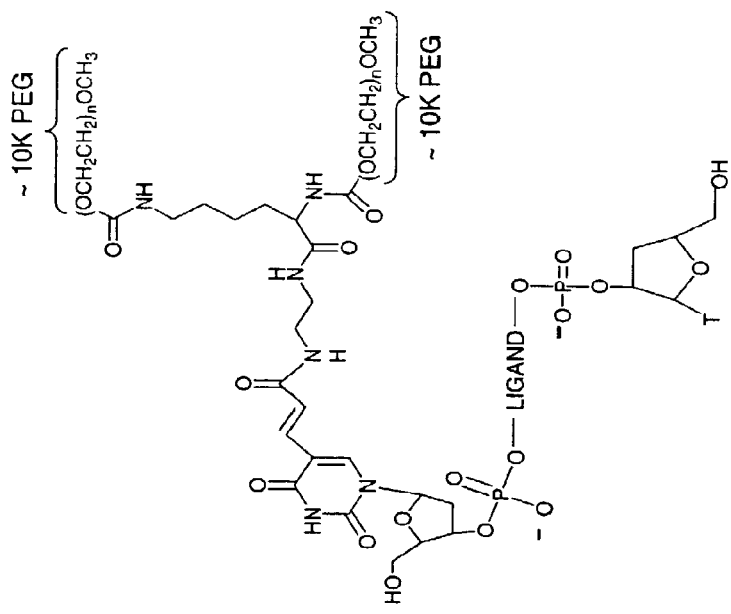
Figure 8:
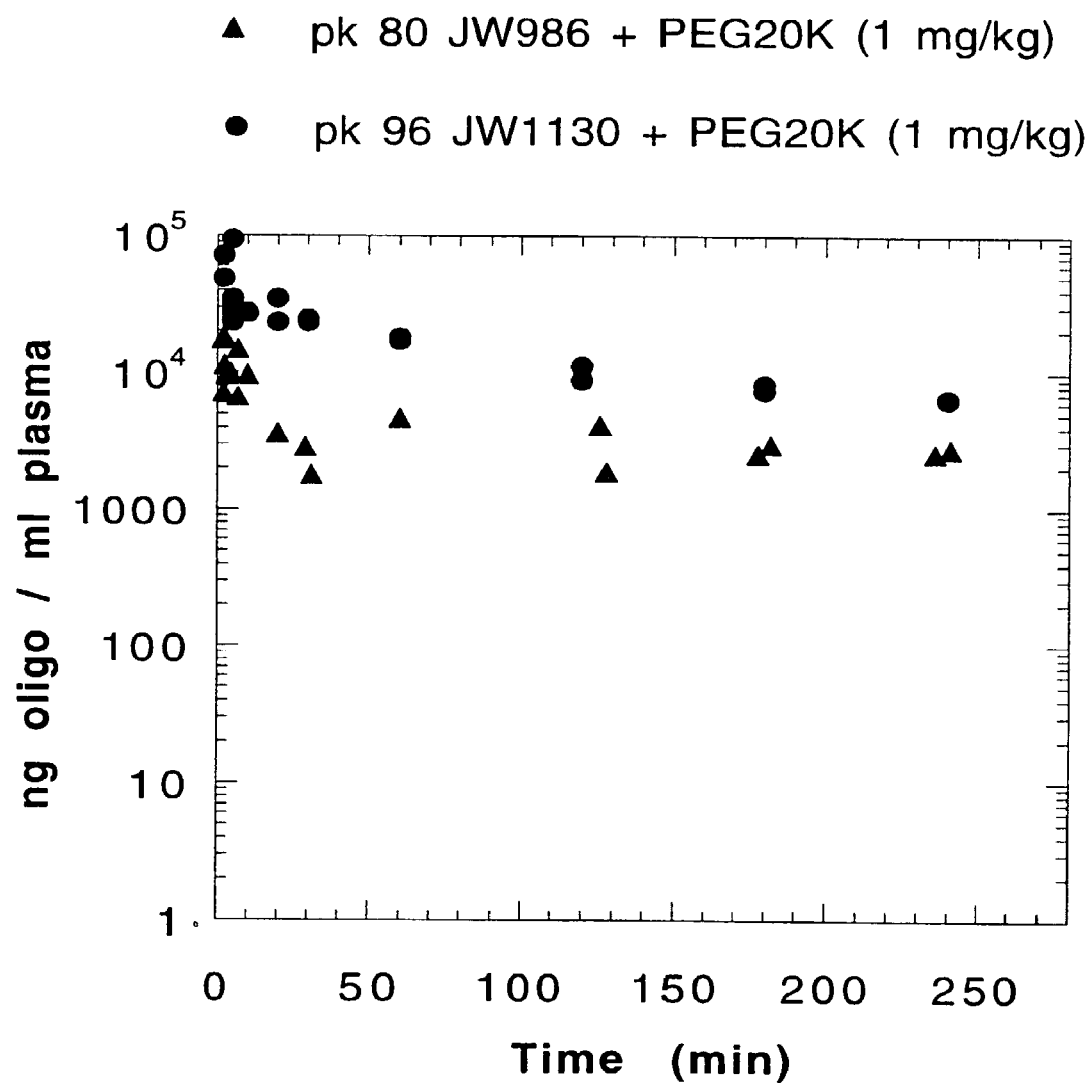
FIG. 8 summarizes the data for the plasma concentration of JW986+PEG20K (SEQ ID NO:29) and JW1130 (SEQ ID NO:23) as a function of time following the bolus injection.

PK 96 was carried out to evaluate the pharmacokinctics of 2' F pyrimidines in conjunction with 2' 0-methyl purines and PEG20K (JW1130) (See FIG. 1R for molecular description; SEQ ID NO:23). FIG. 8 shows the plasma levels of this oligonucleotide in comparison with the all 2' O-methyl version (PK 80, JW986) (See FIG. 1X for molecular description;

SEQ ID NO:29). These data show fairly similar clearance properties for both oligonucleotides.

The observation that JW1130 (SEQ ID NO:23), containing 2' F pyrimidines, shows similar clearance to JW986 (2' O-methyl pyrimidines) suggests that oligonucleotides with 2'F pyrimidines are resistant to nuclease digestion.

Figure 1S:
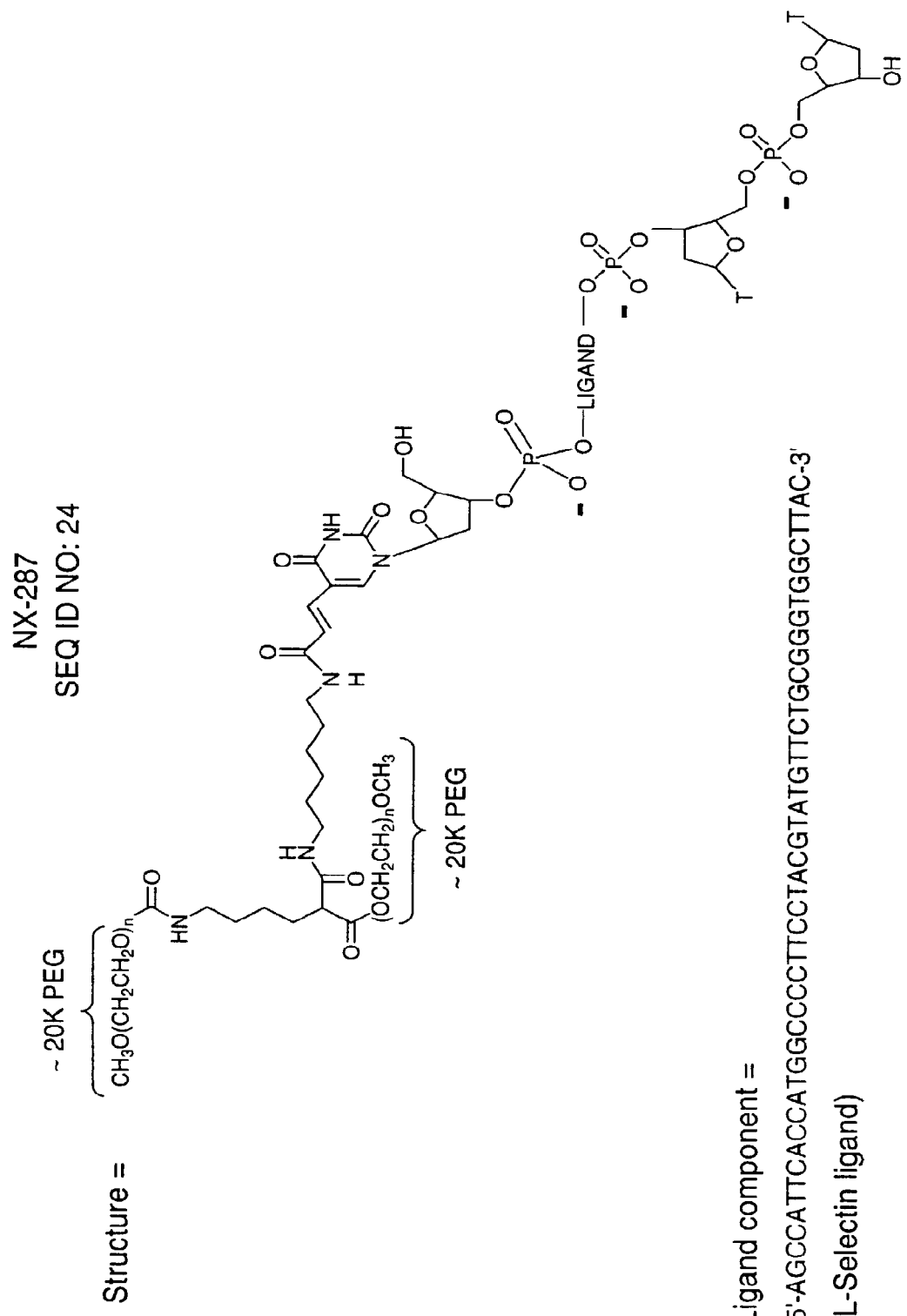
Figure 1T:
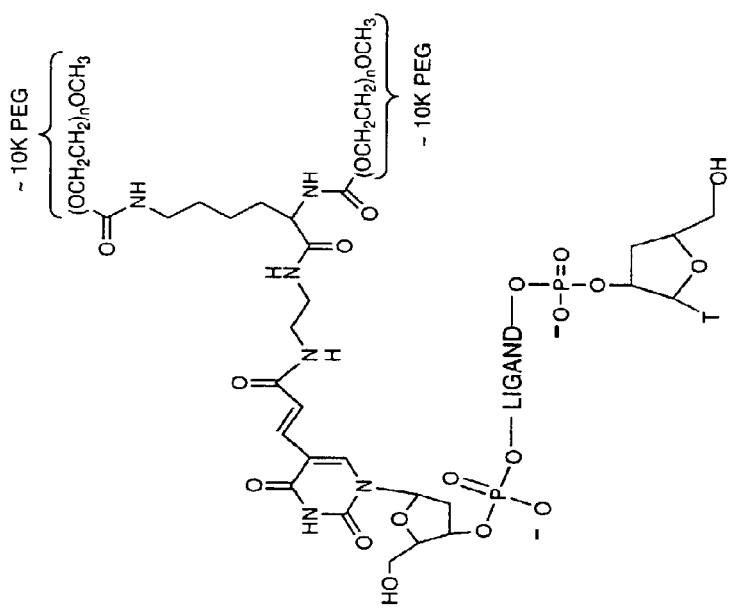
Figure 1U:
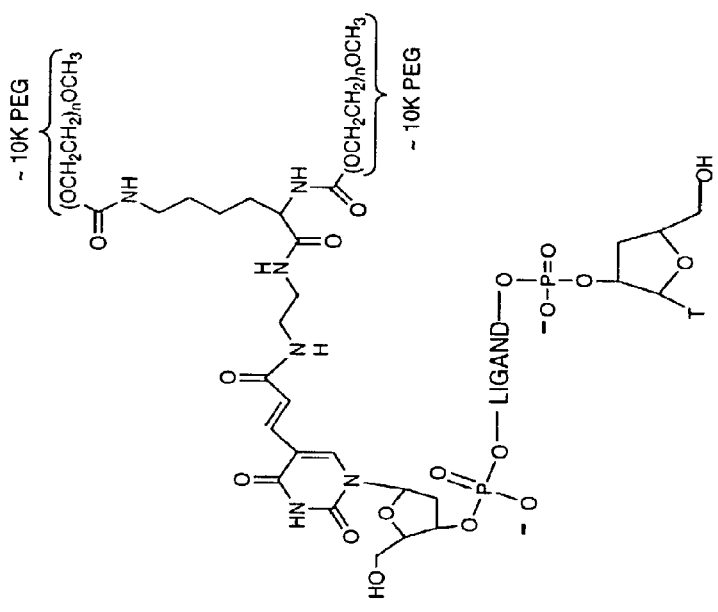
Figure 1V:
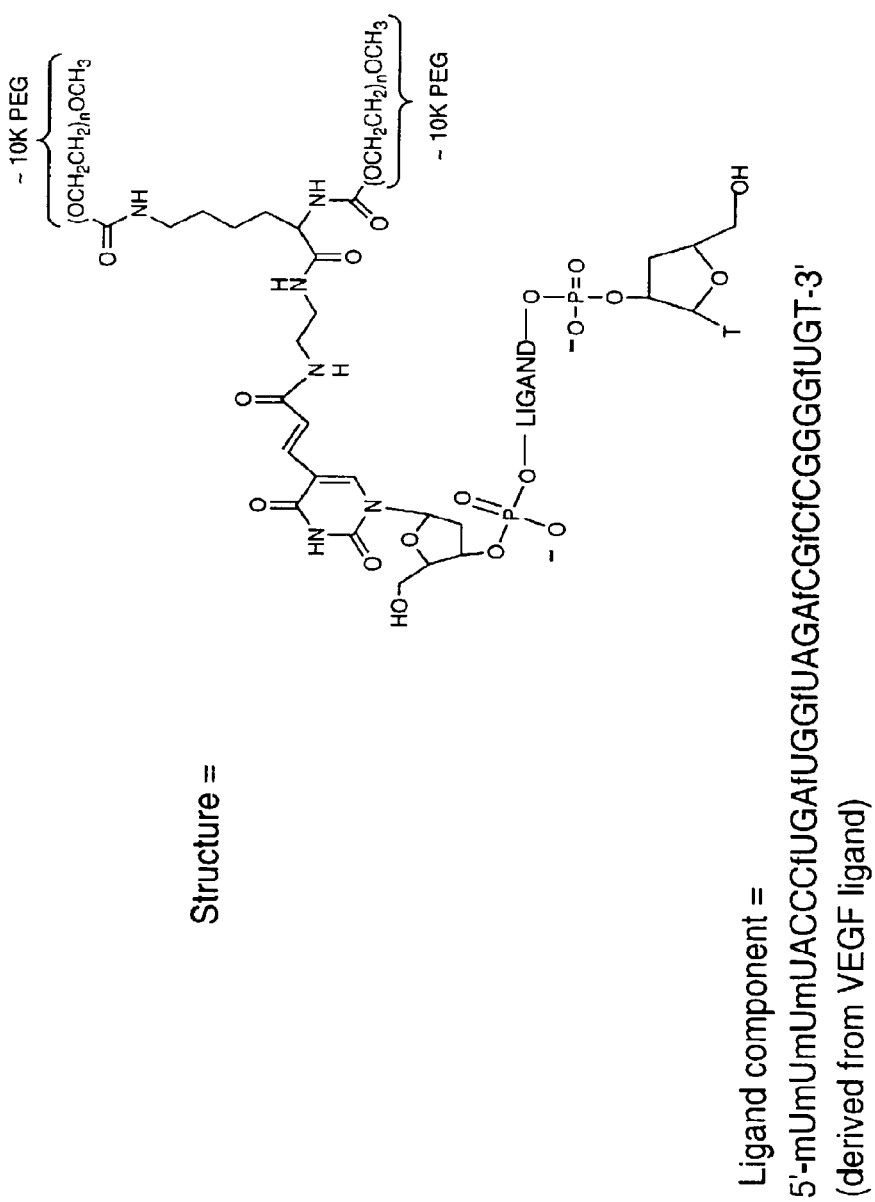
Figure 1X:
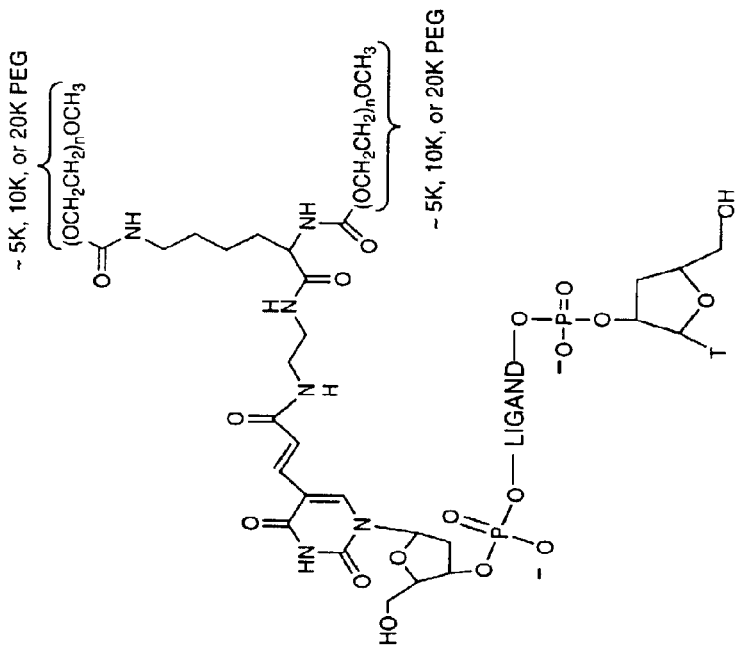
Figure 1Y:
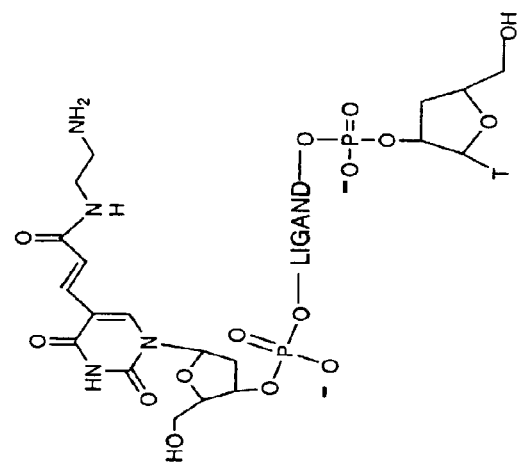
Figure 9:
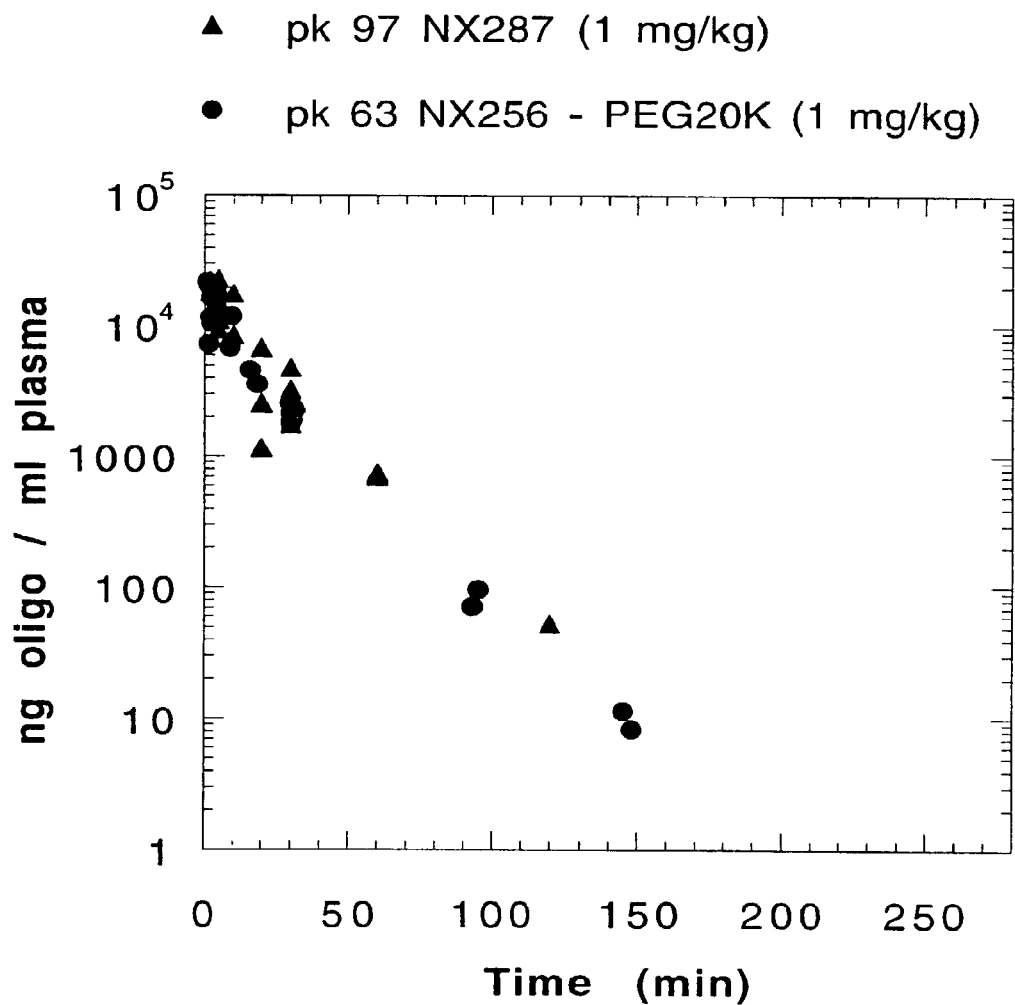
FIG. 9 summarizes the data for the plasma concentration of NX287+PEG40K (SEQ ID NO:24) and NX256 (SEQ ID NO:9) as a function of time following the bolus injection.

PK 97 was carried out to determine the clearance properties of a L-Selectin DNA ligand (NX287) (FIG. 1S; SEQ ID NO:24) conjugated with 40K PEG. FIG. 9 shows the plasma levels of this oligonucleotide as a function of time after bolus injection (dose 1 mg/kg). For comparison, Thrombin DNA ligand (NX256) (FIG. 1H; SEQ ID NO:13) conjugated with 20K PEG was included. As shown in FIG. 9 these two oligonucleotides show similar clearance rates presumably due to metabolism.

Figure 10:
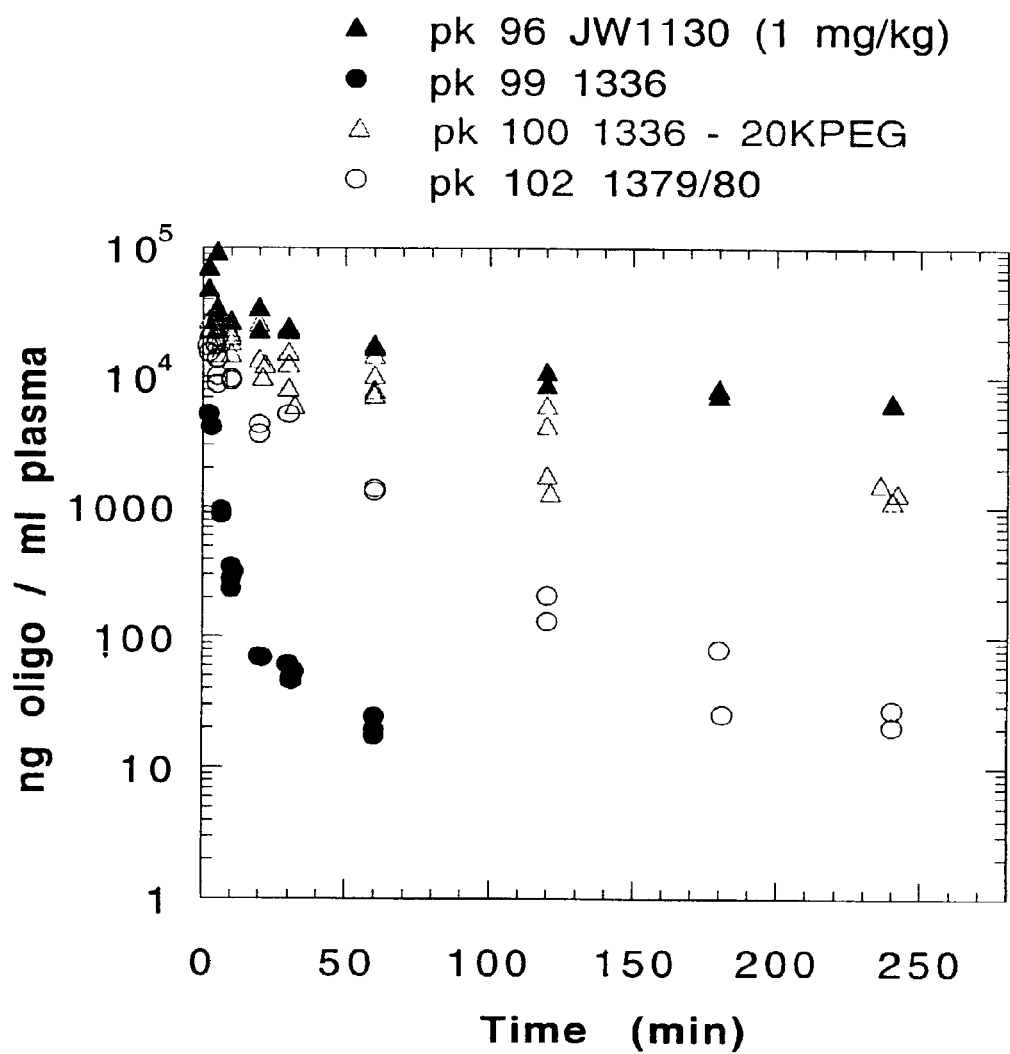
FIG. 10 summarizes the data for the plasma concentration of JW1130 (SEQ ID NO:23), 1136-PEG20K (SEQ ID NO:25), 1336 (SEQ ID NO:30), and 1379/80 (SEQ ID NOS: 26-27) as a function of time following the bolus injection.
Figure 11:
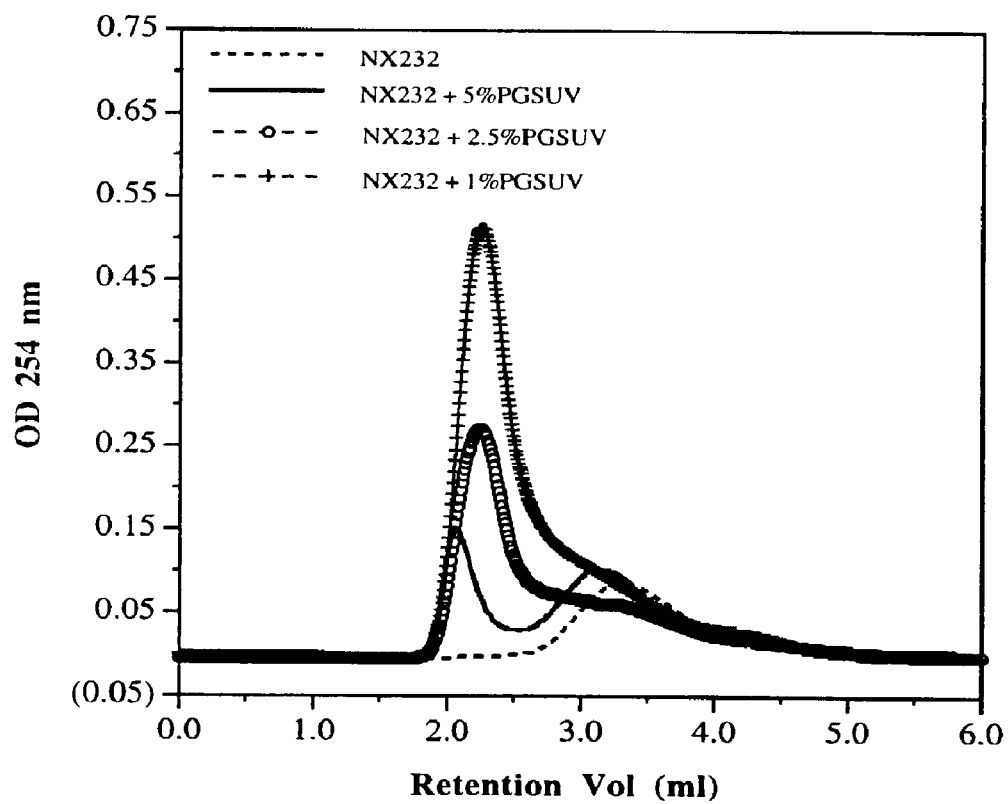
FIG. 11 shows the chromatograms for NX232 (SEQ ID NO:7), NX232+1% PGSUV, NX232+2.5% PGSUV, and NX232+PGSUV.

PK studies 99, 100 and 102 have been carried out as part of a larger study to assess the stability of oligonucleotides in vivo. These studies are shown in FIG. 10. For comparison, PK 96 (JW1130VEGF) 2'F Py 2'O-Met (14 Pu)+PEG 20K) (FIG. 1R; SEQ ID NO:23) is also included. The oligonucleotides used in PK studies 96, 100, and 102 differ only in the number of purine positions that contain 2' deoxy nucleotides, where PK 96 contains no 2' deoxy purines, PK 100 four 2' deoxy purines, and in PK 102 all 14 purines are 2' deoxy. FIG. 10 (SEQ ID NOS:23, 25, 26, 27 and 30) demonstrates a clear relationship between increasing clearance rate and the number of deoxy nucleotides present in the oligonucleotide. This observed increase in clearance rate with increasing number of deoxy nucleotides is assumed to be due to increased metabolism of these oligonucleotides. An encouraging observation is the high level of stability shown for PK 100 containing four 2' deoxy purines, and suggests that post-SELEX modification may be appropriate if a large number of purines can be modified. Also shown in FIG. 10 is PK 99 vs. PK 100, that differ in PEG20K conjugation. As previously observed with other oligonucleotides, conjugation to PEG molecules of significant molecular weight dramatically reduces the observed clearance rate from plasma.

Example 5

Cationic Liposome-Nucleic Acid Ligand Complexes: Toxicity and Their Intracellular Uptake By Human Lymphocytes Toxicity. To determine toxic effects of Liposome-Nucleic Acid Ligands on cells, the human primary peripheral blood lymphocytes (PBLs) were treated with Nucleic Acid Ligand alone, the two types of Liposomes alone, and the two Liposome-Nucleic Acid Ligand combinations (vide infra). Two different types of Liposomes, type 1 (=dioleoylphosphatidylethanolamine (DOPE):aminomannose cholesterol at 1:1 weight ratio) and type 2 (=DOPE: aminomannose cholesterol:DOTAP at a 1:1.5:1 weight ratio) were used for this study. The Liposomes were mixed at a ratio of 5:1 (Liposome: Nucleic Acid Ligand, by weight) with single stranded DNA SELEX ligand RTlt49-PS (5'-d(ATC CGC CTG ATT AGC GAT ACT CAG AAG GAT AAA CTG TCC AGA ACT TGG AsTsTsTsT)-3' (SEQ ID NO:4), where lowercase s indicates a phosphorothioate linkage) that binds to HIV-1 reverse transcriptase with a $K_d$ of approximately 1-5 nM. The Cationic Liposome-Nucleic Acid Ligand Complex was formed by incubating the Liposome and the type 1 or type 2 Liposome with RTlt49-PS at 65° C. for 10 minutes.

PBLS (phytohemagglutinin and natural IL-2 stimulated) were plated at a density of $2\times10^5$ cells per well in 96-well plates. Cells are treated at day 0, split and retreated at day 4 with Nucleic Acid Ligand alone, or the two types of Liposomes alone, or the two Liposome-Nucicic Acid Ligand Complexes. The viable cells were counted at day 7. The percent of viable cells for each of the treatment groups is summarized below:

| Treatment | % Viability |
| --- | --- |
| cells alone | 85 |
| 30 µg/ml RT1t49PS | 82 |
| Liposome type 1 (150 µg/ml) | 85 |
| Liposome type 2 (150 µg/ml) | 63 |
| Liposome type 1 (150 µg/ml) + RT1t49PS (30 µg/ml) | 88 |
| Liposome type 2 (150 µg/ml) + RT1t49PS (30 µg/ml) | 77 |

These results suggest the following. Ligand RTlt49PS was not toxic at concentrations up to 30 µg/ml. Liposome type 1 not toxic at concentrations up to 150 µg/ml while Liposome type 2 is moderately toxic (about 25% reduced viability) at this concentration. The toxicity of Liposome type 2 is expected because DOTAP is known to be toxic. Ligand RTlt49PS apparently reduces the toxicity of Liposome type 2 by about ~50%.

Cellular uptake. Intracellular delivery of fluoresceinated RTlt49PS ligand was examined with CEMss cells (human T cell line) using fluorescence activated cell sorting (FACS) analysis and confocal microscopy. For this study DOPE:aminomannose (1:1 mole ratio) Liposomes were used. Lipid films were prepared from 2.33 mg DOPE and 2.33 mg aminomannose, dissolved in chloroform, and kept under vacuum in a desiccator overnight. 1 ml of 9% sucrose was added to the film and the tube was heated at 65° C. for 0.5 minutes and vortexed. The lipid mixture was then sonicated at a power setting of 7 (microtip) for 2 minutes in a beaker containing water heated to 50° C. An additional 0.5 ml of 9% sucrose was added to the Liposomes and the Liposomes were sized using a MicroTrac particle sizer (average size 45 nm) and sterile filtered using a 0.45 µm cellulose acetate filter. Liposome-Nucleic Acid Ligand Complexes were prepared by incubating the Liposome with the Nucleic Acid Ligand at a 5:1 lipid:oligonucleotide w/w ratio for 10 minutes at 65° C.

For the cellular uptake experiment, $10^6$ CEM cells were diluted in 10 ml of 1640 RPMI/10% fetal calf serum in T25 flasks. The Nucleic Acid Ligand at 0.6 µM, as free drug or in a Liposome Complex, was added to each flask and incubated at 37° C. in an atmosphere containing 5% $CO_2$. Prior to observation, cells were centrifuged and washed twice to remove excess drug.

Confocal Microscopy was performed with an air-cooled argon laser (excitation 488 nm). Confocal images were taken at 1 µm slices (approximately 20 slices per series). Through 24 hours, no significant fluorescence (above background) was detectable in CEM cells incubated with Nucleic Acid Ligand alone. Significant fluorescence was detected in CEM cells incubated with Liposome-associated Nucleic Acid Ligands by 5 hours and increased through 24 hours. Fluorescence appeared to be localized in small vacuoles and not in the nucleus. In polarized cells (example 7 hr incubation with Liposome-associated Nucleic Acid Ligand), the fluorescence is localized in the rear of the cell away from the leading/advancing edge.

FACS analyses were performed with a Coulter Epics Elite equipped with an air-cooled argon laser (excitation 488 nm). CEM cells were gated for forward and side scatter and examined for green fluorescence. Dead cells and aggregates were excluded from the gate. As suggested by confocal microscopy, the fluorescence of cells incubated with Liposome-associated Nucleic Acid Ligand is about an order of magnitude greater than that of cells incubated with free Nucleic Acid Ligand. Uptake of Liposome-associated Nucleic Acid Ligand is not entirely homogeneous. Some cells are significantly more fluorescent than others. For a 5:1 w/w lipid: Nucleic Acid Ligand ratio ($M_r$ of Nucleic Acid Ligand=14, 0000; $M_r$ of lipid=700) and assuming 40,000 lipids per Liposomes, there are approximately 400 Nucleic Acid Ligands per Liposome. The lower detection limit of the FACS is approximately 500 fluorophores per cell or slightly greater than 1 Liposome per cell.

In conclusion, free 5'Fl-RTlt49PS Nucleic Acid Ligands do not significantly localize within CEM cells within 24 hours. Nucleic Acid Ligands associated with DOPE:aminomannose Liposomes localize within CEM cells by 5 hours and continue to localize in the cells through 24 hours. Liposome-associated Nucleic Acid Ligands appear to accumulate in vacuoles and not in the nucleus. The amount of Liposome-associated Nucleic Acid Ligand uptake is at least ten times greater than for free Nucleic Acid Ligand, as judged by FACS analysis.

Example 6

Incorporation of Nucleic Acid Ligands into Preformed Liposomes: Effect of Varying the Negative Charge of the Lipids Small unilamellar vesicles (SUV) composed of distearoylphosphatidylcholine (DSPC), cholesterol (Chol), and distearoylphosphatidylglycerol (DSPG) were prepared using formulations with the molar ratios shown in Table 3. Four compositions containing varying molar percentages of DSPG, a negatively-charged lipid, were prepared to evaluate the effect of negative Liposome charge on the incorporation of a polyanionic Nucleic Acid Ligand. The lipids were dissolved in $CHCl_3$, mixed and dried under a steady stream of nitrogen. The dried lipid film was further dried and stored under vacuum overnight prior to hydration. The lipid film was hydrated with a pH 7.4 phosphate buffer solution (PBS), containing $Na_2HPO_4$ (1.15 g/L), $NaH_2PO_4$ (0.228 g/L), and sucrose (90 g/L), at 65° C. to yield a 50 mg/mL lipid suspension. The hydrated lipid suspension was then sonicated for 15-30 min using a probe-type sonicator until an opalescent solution was obtained.

These preformed SUV were added to an equal volume of Nucleic Acid Ligand 232 (NX232) (SEQ ID NO:7), 1.0 mg/mL in PBS (final concentrations: 0.5 mg/mL NX232, 25 mg/mL lipid). The mixture was incubated at 65° C. for 15 min or kept at room temperature before being chromatographed on a Sephacryl HR S300 size-exclusion column (0.5×20 cm) to separate free from SUV-bound NX232. Chromatography conditions were as follows: eluent, PBS described above; flow rate, 0.1 mL/min; sample injected, 25 μL; detector, UV absorbance at 254 nm; fraction, 0.2 mL/fraction. The collected fractions were also monitored by fluorescence intensity (excited at 494 nm and emitted at 516 nm).

SUV-associated NX232 eluted with the SUV peak (excluded volume) and free-NX232 eluted in the included volume. The chromatogram (FIG. 4) clearly demonstrates that the degree of NX232 association with SUV was dependent upon the DSPG content in the SUV. As the percentage of negatively charged DSPG contained in the SUV was increased between samples A-D, NX232 association with SUV decreased.

TABLE 3

Composition of Liposomes with Various Negative Charges

| | Molar Percentage | | | |
|---|---|---|---|---|
| Lipid | (A) | (B) | (C) | (D) |
| DSPC | 85 | 87.5 | 89 | 90 |
| Cholesterol | 10 | 10 | 10 | 10 |
| DSPG | 5 | 2.5 | 1 | 0 |

Example 7

Incorporation of Nucleic Acid Ligands into Preformed Liposomes: Effect of Varying the Cholesterol Content SUV composed of DSPC and Chol were prepared and NX232 incorporation assayed as in Example 6. The Liposomes contained different molar ratios of DSPC and cholesterol as indicated in Table 4. NX232 associated with the Liposomes and eluted with the SUV when prepared at room temperature.

TABLE 4

Composition of Liposomes with Various Cholesterol Contents

| Formulation | Mole % DSPC | Mole % Cholesterol |
|---|---|---|
| (E) | 95 | 5 |
| (F) | 90 | 10 |
| (G) | 85 | 15 |
| (H) | 80 | 20 |
| (I) | 75 | 25 |
| (J) | 70 | 30 |
| (K) | 65 | 35 |

Liposome formulations J and K (approximately 2:1 mole ratio of DSPC:cholesterol) allow for the most efficient incorporation of the Nucleic Acid Ligand NX232.

Example 8

Incorporation of Nucleic Acid Ligands into Preformed LIPOSOMES: Effect of Varying Lipid/Nucleic Acid Ligand Ratio with a Fixed Amount of NX232

DSPC:Chol (2:1 molar ratio) SUV were prepared and assayed as in Example 6, but with varying lipid/NX232 ratios. A fixed amount of NX232 (SEQ ID NO:7), 1.0 mg/mL, was mixed at room temperature with an equal volume of SUV, containing lipid concentrations from 2.5 to 50 mg/mL (Table 5). The results suggest that the maximal association of NX232 with SUV was achieved at lipid/NX ratios (w/w) of 25/1. The highest lipid/NX ratio, 50/1, did not increase the amount of NX232 bound to SUV.

TABLE 5

Lipid/NX Ratios (w/w) Tested with
A Fixed Amount of NX232

| Lipid Conc. (mg/mL) | NX Conc. (mg/mL) | Lipid/NX Ratio (w/w) |
|---|---|---|
| 2.5 | 1.0 | 2.5/1 |
| 5.0 | 1.0 | 5/1 |
| 10.0 | 1.0 | 10/1 |
| 25.0 | 1.0 | 25/1 |
| 50.0 | 1.0 | 50/1 |

Example 9

Incorporation of Nucleic Acid Ligands into Preformed Liposomes: Effect of Varying Lipid/Nucleic Acid Ligand Ratio with a Fixed Amount of SUV Preformed SUV (DSPC/CH:2/1), 50 mg/mL, prepared as in Example 6, were mixed with an equal volume of NX232 at various concentrations from 0.5 to 5.0 mg/mL at room temperature (Table 6). The results indicate that maximal association of NX232 with SUV was obtained at a lipid/NX232 ratio (w/w) of 25/1. The fraction of NX232 associated with SUV decreased with lower lipid/NX232 ratio.

TABLE 6

Lipid/NX Ratios (w/w) Tested with
A Fixed Amount of SUV

| Lipid Conc. (mg/mL) | NX Conc. (mg/mL) | Lipid/NX Ratio (w/w) |
|---|---|---|
| 50 | 5.0 | 10/1 |
| 50 | 4.0 | 12.5/1 |
| 50 | 3.0 | 16.7/1 |
| 50 | 2.5 | 20/1 |
| 50 | 2.0 | 25/1 |
| 50 | 1.0 | 50/1 |
| 50 | 0.5 | 100/1 |

Example 10

Incorporation of Nucleic Acid Ligands into Preformed Liposomes: Effect of Varying the Phospholipid Chain Length SUV were prepared as in Example 6 from the phospholipids indicated in Table 7 to study NX232 association with SUV made of phospholipids with different chain length.

TABLE 7

Composition of Liposomes with Various Phospholipids

| Formulation | Phospholipid/Cholesterol | Molar Ratio |
|---|---|---|
| (M) | Distearoylphosphatidylcholine (C18)/Chol | 70/30 |
| (N) | Dipalmitoylphosphatidylcholine (C16)/Chol | 70/30 |
| (O) | Dimyristoylphosphatidylcholine (C14)/Chol | 70/30 |

Of the three Liposome formulations tested, the DPPC/cholesterol Liposome appears to have the highest capacity to incorporate the Nucleic Acid Ligand NX232.

Example 11

Figure 12:
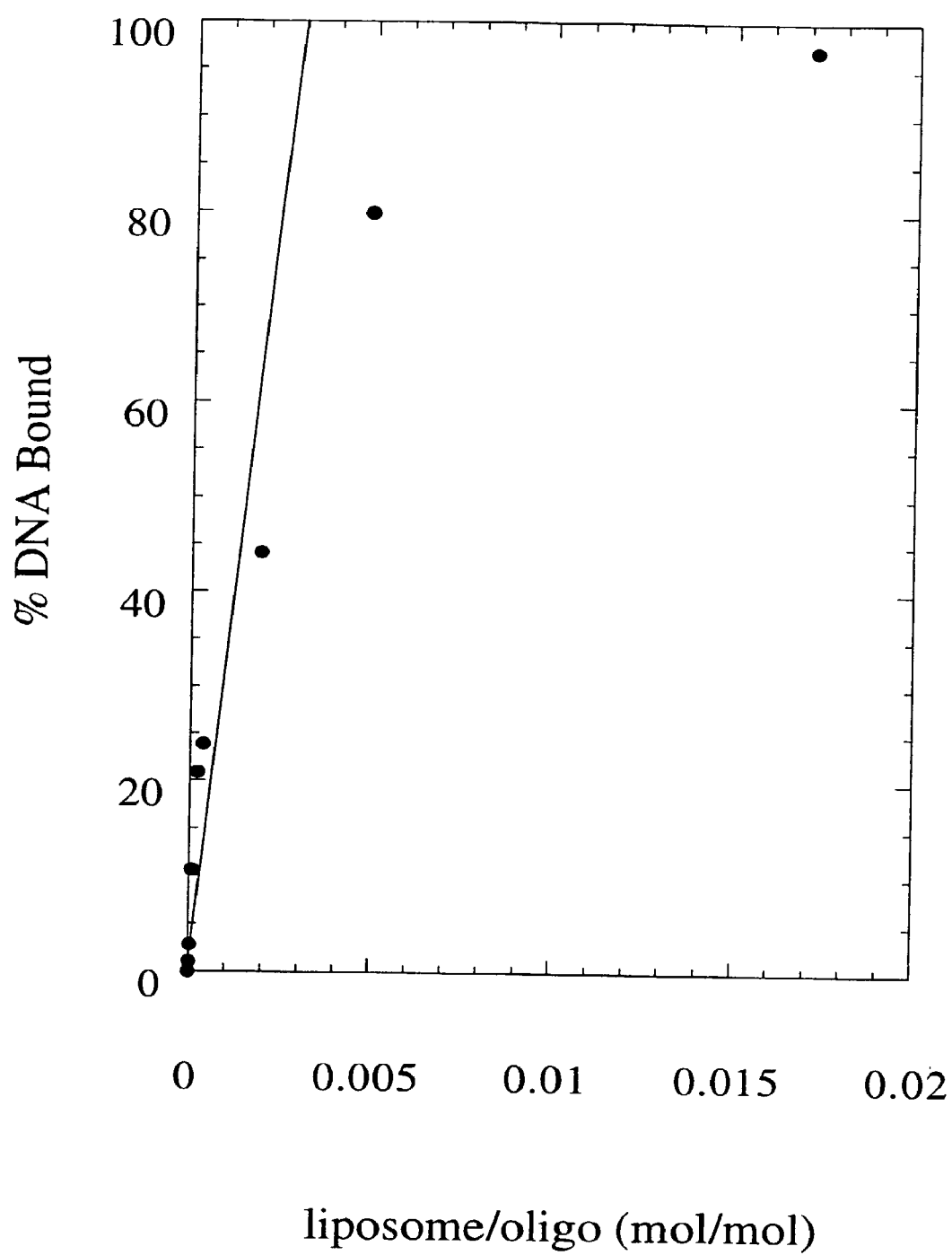
FIG. 12 shows the fraction of bound Nucleic Acid Ligand (NX253) (SEQ ID NO:8) as a function of Liposome:Nucleic Acid Ligand ratio.

Analysis of the Nucleic Acid Ligand-Liposome Complex by Non-Denaturing Gel Electrophoresis In this example, the incorporation of a Nucleic Acid Ligand conjugate with cholesterol into the liposomal formulation is demonstrated. The Liposome formulation used in this study is the DSPC:Cholesterol (2:1, mol/mol). The ability of the Liposome to incorporate the cholesterylated thrombin ligand NX 253, radiolabeled with $^{125}$I-Bolton-Hunter reagent (5'-[Cholesterol][dT-NH-$^{125}$I-Bolton-Hunter]-d(CAG TCC GTG GTA GGG CAG GTT GGG GTG ACT TCG TGG AA)[3'3' dT]dT-3' (SEQ ID NO:8), where dT-NH-$^{125}$I-Bolton-Hunter is the Amino-Modifier C6 dT (Glen Research, Sterling, Va.) conjugated to the Bolton-Hunter reagent (New England Nuclear, Boston, Mass.) and 3'3' dT (dT-5'-CE phosphoramidite, Glen Research, Sterling, Va.) is the inverted-orientation phosphoramidite) was examined by determining the fraction of bound Nucleic Acid Ligand as a function of Liposome:Nucleic Acid Ligand ratio. The Nucleic Acid Ligand-Liposome Complexes were prepared by incubating the Nucleic Acid Ligand with the Liposome in 25 mM Tris buffer, pH 7.4 containing 9% sucrose at 65° C. for 15 min. The free Nucleic Acid Ligand can be separated from the Liposome-bound Nucleic Acid Ligand by non-denaturing polyacrylamide gel electrophoresis. This method allows for rapid and complete separation of the two species. In order to allow the Liposome-bound Nucleic Acid Ligand to enter the gel (so that it can be visualized), it is necessary to disrupt the Liposomes by adding a 1% solution of triton X-100 to the loading wells for about 5 minutes prior to termination of the electrophoresis run. The amount of Liposome-bound Nucleic Acid Ligand was determined from the relative amount of the free Nucleic Acid Ligand, which runs as a well-defined band, by phosphorimager analysis. Assuming that there are approximately 60,000 lipids per Liposome, and that the mean MW of a lipid is 655.9 Da (=790.15×0.67+386.7×0.33), the saturation of the Liposome with the Nucleic Acid Ligand occurs at the molar ratio of Nucleic Acid Ligand to Liposome of approximately 300 (FIG. 12). The analog of NX253 that does not have the cholesterol moiety is not incorporated into the Liposome over the same range of Liposome concentrations (data not shown).

Example 12

Passive Encapsulation of Nucleic Acid Ligands into Liposomes

The Nucleic Acid Ligands are encapsulated within the aqueous interior of Liposomes. An aqueous solution of a Nucleic Acid Ligand is prepared by dissolving the Nucleic Acid Ligands in phosphate buffer solution (PBS) to yield a stock solution with a concentration of approximately 3.5 mg/ml. A lipid film containing DSPC:Chol (2:1 mole ratio) is prepared by drying the lipid mixture from chloroform:methanol:water (1:5:1, v:v:v) solvent. One ml of the Nucleic Acid stock solution is added to the lipid film and bath sonicated at a temperature of 40° C. for 10 seconds. The resulting solution is put through a 4-cycle freeze-thaw procedure using liquid nitrogen. The resulting homogeneous solution is extruded first through a 0.8 µm filter membrane (3 times) then extruded through a 0.45 µm filter (3 times) and finally through a 0.2 µm filter (3 times). Unencapsulated Nucleic Acid Ligands are Example 13

Remote Loading of Nucleic Acid Ligands into Liposomes

The Nucleic Acid Ligands are encapsulated within the aqueous interior of MLVs by remote loading. A lipid mixture of DSPC:Chol (2:1 mole ratio) is prepared as a lipid film using 20 µmol of lipid. The lipid film is vortexed into suspension using 0.1 M $MgCl_2$ at 65° C. to form MLVs having an average diameter of one micron. The Liposome suspension is frozen in liquid nitrogen and thawed at 65° C. The freeze/thaw cycling is repeated three times to ensure that the salt is uniformly distributed throughout the lamellae. The osmolarity of the internal aqueous phase is approximately 300 milliosmoles (mOsm). The Liposome suspension is pelleted by centrifugation at 10,000 g for 15 minutes to remove external $MgCl_2$ solution. The supernatant is removed and the Liposome pellet is heated at 65° C. for 5 minutes. A solution of Nucleic Acid Ligand (20 µg in 100 µl water) is preheated for 5 minutes at 65° C. and added to the Liposome pellet. Heating is continued for 30 minutes and the sample is then slowly cooled to room temperature and diluted with 1 ml PBS. Unentrapped Nucleic Acid Ligand is removed by centrifugation of the MLVs followed by supernatant removal. The pellet is resuspended in fresh PBS and re-pelleted by centrifugation.

Example 14

Covalent Conjugation of Nucleic Acid Ligands to Liposomes

In scheme 1 provided below, a heterobifunctional PEG-2000 (PEG with molecular weight 2000 Da) containing a N-hydroxysuccinimide ester and vinyl sulfone functionalities was first conjugated to a Liposome containing 2 mole % distearylphosphatidylethanolamine (DSPE) via the N-hydroxysuccinimide ester moiety. The product was purified from the free PEG by size exclusion chromatography. The vinyl sulfone product was then allowed to react with reduced NX 256 (FIG. 1D; SEQ ID NO:9). A DSPE-PEG-2000-vinyl sulfone is commercially available and can be used to manufacture Liposomes that contain the vinyl sulfone functionality, thus eliminating a conjugation step from Scheme 1.

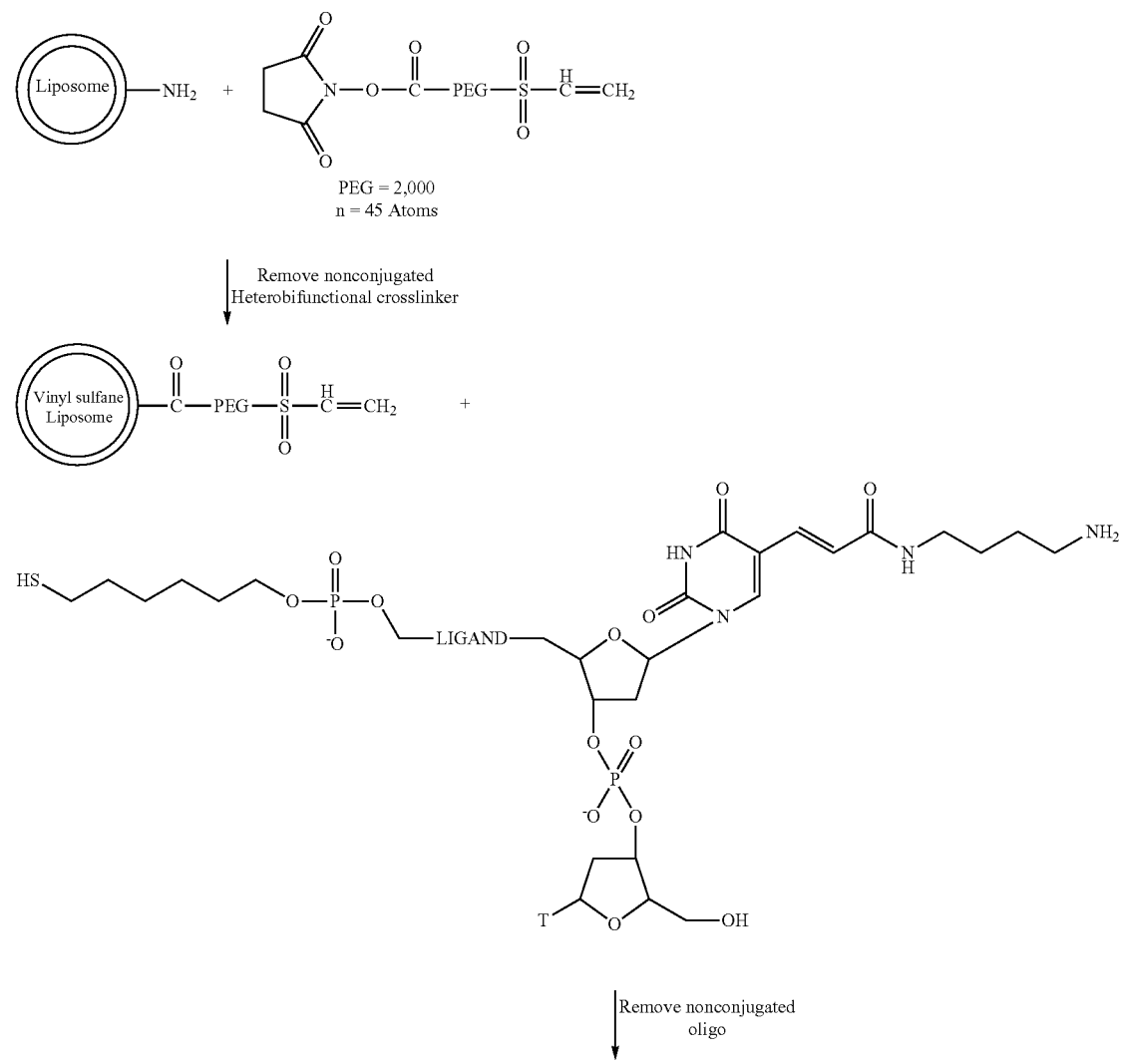

-continued

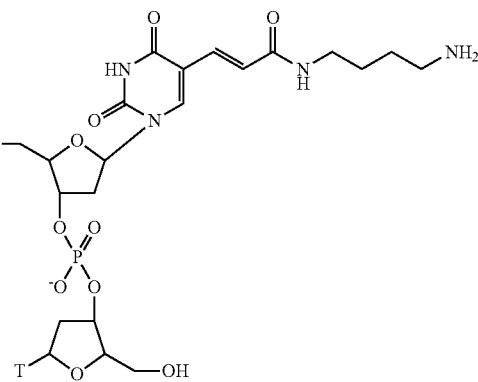

The second reaction, shown below as scheme 2, has been completed. The starting material was a distearylphosphatidylcholine (DSPC) Liposome containing 2 mole % DSPE maleimide. Using a value of 50,000 lipids per Liposome, the Liposome should have approximately 1000 maleimide molecules per Liposome, about 600 of which are available on the outside. The Nucleic Acid Ligand-Liposome Complex was separated from the free Nucleic Acid Ligand via size exclusion chromatography (vide supra). From the absorbance at 260 nm, it was estimated that approximately 200 molecules of the Nucleic Acid Ligand were conjugated to each Liposome.

Example 15

In Vitro and In Vivo Efficacy of Nucleic Acid Ligand-Liposome Complex. Dialkylglycerol (DAG)-Modified VEGF Ligand (NX278) Embedded in Liposome Bilayer NX278-Liposome Complex was prepared by incubating NX-278 (1 mg) (FIG. 1N; SEQ ID NO:19) with of a mixture of DSPC:cholesterol (50 mg) in 10 mM phosphate (pH 7.4) buffer containing 9% sucrose and sonicated for 15-30 min

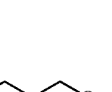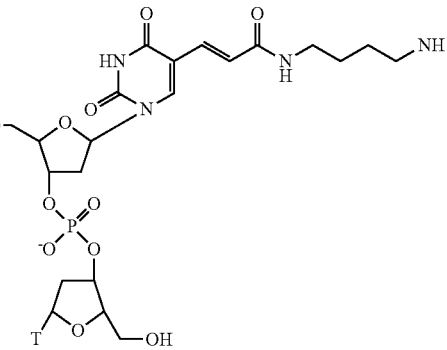

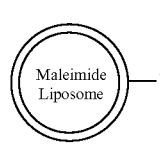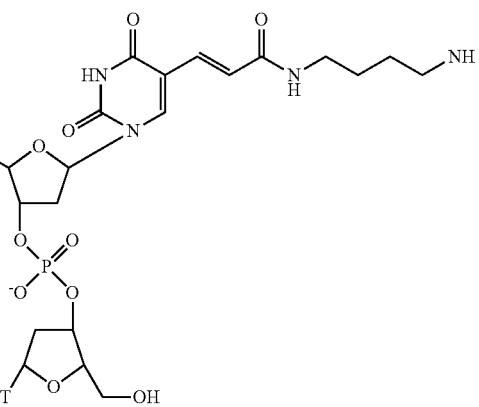

using a probe-type sonicator until opalescent solution was obtained. The control Nucleic Acid Ligand-Liposome Complex containing a sequence scrambled analog of ligand NX-278 (scNX278) (FIG. 1W; SEQ ID NO:28) was prepared in the same manner. The size of Liposome particles (typically 50-100 nM), determined in a particle analyzer (Leeds & Northrup Model Microtrack UPA 150, Horsham, Pa.) was similar to those obtained in the absence of the Nucleic Acid Ligand. NX278-Liposome Complex competed with a biotin-labeled Nucleic Acid Ligand to VEGF for binding to polystyrene-immobilized VEGF in a competition ELISA assay with an apparent ED50 of $=10^{-7}$ M. In the same assay, scNX278-Liposome Complex was not an effective competitor up to 2 µM Nucleic Acid Ligand. For comparison, free Nucleic Acid Ligand to VEGF with the same sequence as NX278 but lacking the DAG moiety at the 5' end, NX213 (FIG. 1P; SEQ ID NO:21), exhibited a competition ED50 value of $=10^{-9}$ M. The reduced ability of NX278-Liposome compared to NX213 to bind to immobilized VEGF may be due to a simple geometric constraint, since only a fraction of the Nucleic Acid Ligand displayed on the outer surface of the Liposomes is expected to be available for binding to a planar surface. In addition, the fraction of Nucleic Acid Ligand displayed on the inner surface would obviously not be available for binding in this assay.

The effects of NX278-liposome, scNX278-liposome and NX213 on the proliferation of human umbilical vein endothelial cells (HUVEC) and Kaposi's Sarcoma (KS) cells in tissue culture were examined. HUVECs were grown in the presence of VEGF (10 ng/ml) in IMDM:Ham's F12 (1:1) medium containing 10% fetal calf serum (FCS) and heparin (45 µg/ml). Cells were plated in 24-well gelatin-coated plates at a density of 20,000 cells per well on day zero and treated with the above ligands at concentrations between 0.1 nM to 1 µM on days 1, 2, and 3 (replacing the media along with the ligands). Cell count was performed on day 4. KS cell line KSY-1 was plated in 24-well gelatin coated plates at a density of 7,500-10,000 cells per well on day zero in medium containing RPMI 1640 supplemented with 2% FCS, L-glutamine, penicillin and streptomycin. Nucleic Acid Ligands were added at concentrations between 0.1 nM to 1 µM in fresh medium on day 1, 2, and 3 and the cell count was performed on day 4. NX278-Liposome inhibited the proliferation of HUVECs with an IC50 of $=300$ nM (the concentration refers to the Nucleic Acid Ligand component); the free Nucleic Acid analog, NX213, was significantly less effective (IC50>1 µM). NX278-Liposome also inhibited the proliferation of KS cells with an IC50 of $=100$ nM; at 1 µM NX278-Liposome, the growth of these cells was completely inhibited. scNX278-Liposome and NX213 exhibited IC50 values of >1 µM.

The ability of NX278-liposome to inhibit the vascular permeability activity of VEGF in vivo was examined. The vascular permeability assay (also known as the Miles assay (Miles, A. A. and Miles, E. M. (1952) *J. Physiol.* (London) 118:228) was performed in guinea pigs essentially as described (Senger, R. S. et al., (1983) *Science* 219:983). NX278-Liposome at the concentration of 1 µM significantly inhibited the VEGF-induced vascular permeability increase. The control compound, scNX278-Liposome was not inhibitory at this concentration; in fact the vascular permeability appeared to be enhanced.

The invention claimed is:

1. A method for imaging a site expressing a Target in a patient, the method comprising:
   covalently linking a Nucleic Acid Ligand with magnetite, wherein said Nucleic Acid Ligand has a specific binding affinity for said Target;
   administering said Nucleic Acid Ligand associated with magnetite to a patient; and
   performing nuclear magnetic resonance (NMR) imaging.

\* \* \* \* \*